US012636100B2

(12) United States Patent
Saber et al.

(10) Patent No.: US 12,636,100 B2
(45) Date of Patent: May 26, 2026

(54) LOAD SENSING OF ELONGATED MEDICAL DEVICE IN ROBOTIC ACTUATION

(71) Applicant: Corindus, Inc., Newton, MA (US)

(72) Inventors: Omid Saber, Waltham, MA (US); Andrew Clark, Waltham, MA (US); Cameron Canale, Groton, MA (US); Saeed Sokhanvar, Belmont, MA (US); Eric Klem, Lexington, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 275 days.

(21) Appl. No.: 18/352,332

(22) Filed: Jul. 14, 2023

(65) Prior Publication Data

US 2023/0355331 A1     Nov. 9, 2023

Related U.S. Application Data

(63) Continuation of application No. 17/597,456, filed as application No. PCT/US2020/041904 on Jul. 14, 2020, now Pat. No. 11,744,659.

(Continued)

(51) Int. Cl.
| | |
|---|---|
| *A61B 34/30* | (2016.01) |
| *A61B 34/20* | (2016.01) |
| *A61B 90/00* | (2016.01) |
| *A61B 17/00* | (2006.01) |
| *A61M 25/01* | (2006.01) |

(52) U.S. Cl.
CPC .............. *A61B 34/30* (2016.02); *A61B 34/20* (2016.02); *A61B 90/03* (2016.02); *A61B 2017/00203* (2013.01); *A61B 2017/00725* (2013.01); *A61B 2034/2048* (2016.02); *A61B 2034/2059* (2016.02); *A61B 2034/301* (2016.02); *A61B 2090/034* (2016.02); *A61B 2090/064* (2016.02);

(Continued)

(58) Field of Classification Search
None
See application file for complete search history.

(56) References Cited

U.S. PATENT DOCUMENTS

| | | | |
|---|---|---|---|
| 3,821,525 A | 6/1974 | Eaton et al. | |
| 5,312,338 A | 5/1994 | Nelson et al. | |

(Continued)

FOREIGN PATENT DOCUMENTS

| | | |
|---|---|---|
| CN | 108158656 | 6/2018 |
| EP | 1986563 | 11/2008 |

(Continued)

OTHER PUBLICATIONS

International Search Report Received for Corresponding PCT Application No. PCT/US2020/041904, dated Nov. 20, 2020.

(Continued)

*Primary Examiner* — Aurelie H Tu

(57) ABSTRACT

An apparatus includes a drive module having a drive module base component and a load-sensed component. An elongated medical device (EMD) is removably coupled to an isolated component. The isolated component is isolated from an external load other than an actual load acting on the EMD. The isolated component is removably coupled to the load-sensed component. A load sensor is secured to the drive module base component and the load-sensed component sensing the actual load acting on the EMD.

24 Claims, 29 Drawing Sheets

Related U.S. Application Data

(60) Provisional application No. 63/012,607, filed on Apr. 20, 2020, provisional application No. 62/876,489, filed on Jul. 19, 2019.

(52) U.S. Cl.
CPC .... *A61B 2090/376* (2016.02); *A61M 25/0113* (2013.01)

(56) References Cited

U.S. PATENT DOCUMENTS

| | | | |
|---|---|---|---|
| 5,350,101 | A | 9/1994 | Godlewski |
| 6,283,921 | B1 | 9/2001 | Nix et al. |
| 6,726,675 | B1 | 4/2004 | Beyer |
| 6,817,973 | B2 | 11/2004 | Merril et al. |
| 7,331,967 | B2 | 2/2008 | Lee et al. |
| 7,766,856 | B2 | 8/2010 | Ferry et al. |
| 7,766,894 | B2 | 8/2010 | Weitzner et al. |
| 7,972,298 | B2 | 7/2011 | Wallace et al. |
| 8,004,229 | B2 | 8/2011 | Nowlin et al. |
| 8,048,088 | B2 | 11/2011 | Green et al. |
| 8,052,621 | B2 | 11/2011 | Wallace et al. |
| 8,052,636 | B2 | 11/2011 | Moll et al. |
| 8,092,397 | B2 | 1/2012 | Wallace et al. |
| 8,202,244 | B2 | 6/2012 | Cohen et al. |
| 8,286,510 | B2 | 10/2012 | Meiss et al. |
| 8,343,096 | B2 | 1/2013 | Kirschenman et al. |
| 8,391,957 | B2 | 3/2013 | Carlson et al. |
| 8,617,102 | B2 | 12/2013 | Moll et al. |
| 8,631,713 | B2 | 1/2014 | Fujimoto et al. |
| 8,684,952 | B2 | 4/2014 | Weitzner et al. |
| 8,736,212 | B2 | 5/2014 | Sandhu et al. |
| 8,786,241 | B2 | 7/2014 | Nowlin et al. |
| 8,801,661 | B2 | 8/2014 | Moll et al. |
| 8,823,308 | B2 | 9/2014 | Nowlin et al. |
| 8,944,070 | B2 | 2/2015 | Guthart et al. |
| 9,101,734 | B2 | 8/2015 | Selkee |
| 9,283,046 | B2 | 3/2016 | Walker et al. |
| 9,326,822 | B2 | 5/2016 | Lewis et al. |
| 9,402,555 | B2 | 8/2016 | Kirschenman |
| 9,408,669 | B2 | 8/2016 | Kokish et al. |
| 9,480,820 | B2 | 11/2016 | Goldenberg et al. |
| 9,498,601 | B2 | 11/2016 | Tanner et al. |
| 9,565,990 | B2 | 2/2017 | Lee et al. |
| 9,572,626 | B2 | 2/2017 | Verner et al. |
| 9,603,667 | B2 | 3/2017 | Yang et al. |
| 9,782,564 | B2 | 10/2017 | Zirps et al. |
| 9,814,864 | B2 | 11/2017 | Scarpine et al. |
| 9,825,455 | B2 | 11/2017 | Sandhu et al. |
| 10,046,140 | B2 | 8/2018 | Kokish et al. |
| 10,213,264 | B2 | 2/2019 | Tanner et al. |
| 10,307,214 | B2 | 6/2019 | Lathrop et al. |
| 2002/0169396 | A1 | 11/2002 | Wollschlager |
| 2002/0177789 | A1 | 11/2002 | Ferry et al. |
| 2004/0254566 | A1 | 12/2004 | Plicchi et al. |
| 2007/0060879 | A1 | 3/2007 | Weitzner et al. |
| 2008/0009791 | A1 | 1/2008 | Cohen et al. |
| 2008/0243064 | A1 | 10/2008 | Stahler et al. |
| 2009/0082722 | A1 | 3/2009 | Munger et al. |
| 2010/0204646 | A1 | 8/2010 | Plicchi et al. |
| 2010/0268031 | A1* | 10/2010 | Koyama ............. A61B 1/0051 |
| | | | 600/146 |
| 2012/0022405 | A1 | 1/2012 | Wallace et al. |
| 2012/0071752 | A1 | 3/2012 | Sewell et al. |
| 2012/0071821 | A1 | 3/2012 | Yu |
| 2012/0172891 | A1 | 7/2012 | Lee |
| 2012/0179167 | A1 | 7/2012 | Wenderow et al. |
| 2012/0209293 | A1 | 8/2012 | Carlson et al. |
| 2013/0281897 | A1 | 10/2013 | Hoffmann et al. |
| 2014/0222021 | A1 | 8/2014 | Diolaiti et al. |
| 2014/0276389 | A1 | 9/2014 | Walker |
| 2014/0276948 | A1 | 9/2014 | Zirps |
| 2015/0005757 | A1 | 1/2015 | Wang et al. |
| 2015/0142013 | A1 | 5/2015 | Tanner et al. |
| 2016/0310222 | A1 | 10/2016 | Kottenstette |
| 2017/0007343 | A1 | 1/2017 | Yu |
| 2017/0348060 | A1 | 12/2017 | Blacker |
| 2018/0250078 | A1 | 9/2018 | Shocat et al. |
| 2018/0311468 | A1 | 11/2018 | Clayman et al. |
| 2018/0353250 | A1 | 12/2018 | Fournier et al. |
| 2018/0361055 | A1 | 12/2018 | Pereira et al. |
| 2019/0175887 | A1 | 6/2019 | Shameli |
| 2019/0175888 | A1 | 6/2019 | Abdelwahed et al. |
| 2020/0008893 | A1 | 1/2020 | Janik et al. |
| 2020/0015824 | A1 | 1/2020 | Eisinger et al. |
| 2020/0129246 | A1 | 4/2020 | Govari et al. |

FOREIGN PATENT DOCUMENTS

| | | |
|---|---|---|
| EP | 2038627 | 3/2009 |
| EP | 2218396 | 8/2010 |
| EP | 2124800 | 11/2010 |
| EP | 2332482 | 6/2011 |
| JP | 2009131245 | 6/2009 |
| JP | 2010015164 | 1/2010 |
| JP | 2011028293 | 2/2011 |
| JP | 2011519678 | 7/2011 |
| JP | 2014004310 | 1/2014 |
| JP | 2016120313 | 7/2016 |
| JP | 2018118096 | 8/2018 |
| WO | 2013101269 | 7/2013 |
| WO | 2018176458 | 10/2018 |
| WO | 2020055427 | 3/2020 |
| WO | 2021011518 | 1/2021 |
| WO | 2021011533 | 1/2021 |
| WO | 2021011551 | 1/2021 |
| WO | 2021011554 | 1/2021 |
| WO | 2021011571 | 1/2021 |

OTHER PUBLICATIONS

European Search Report for Corresponding EP Application No. EP 20844974.1, dated Jan. 16, 2023.
European Search Report for Corresponding EP Application No. EP 22198309.1, dated Jan. 13, 2023.

* cited by examiner

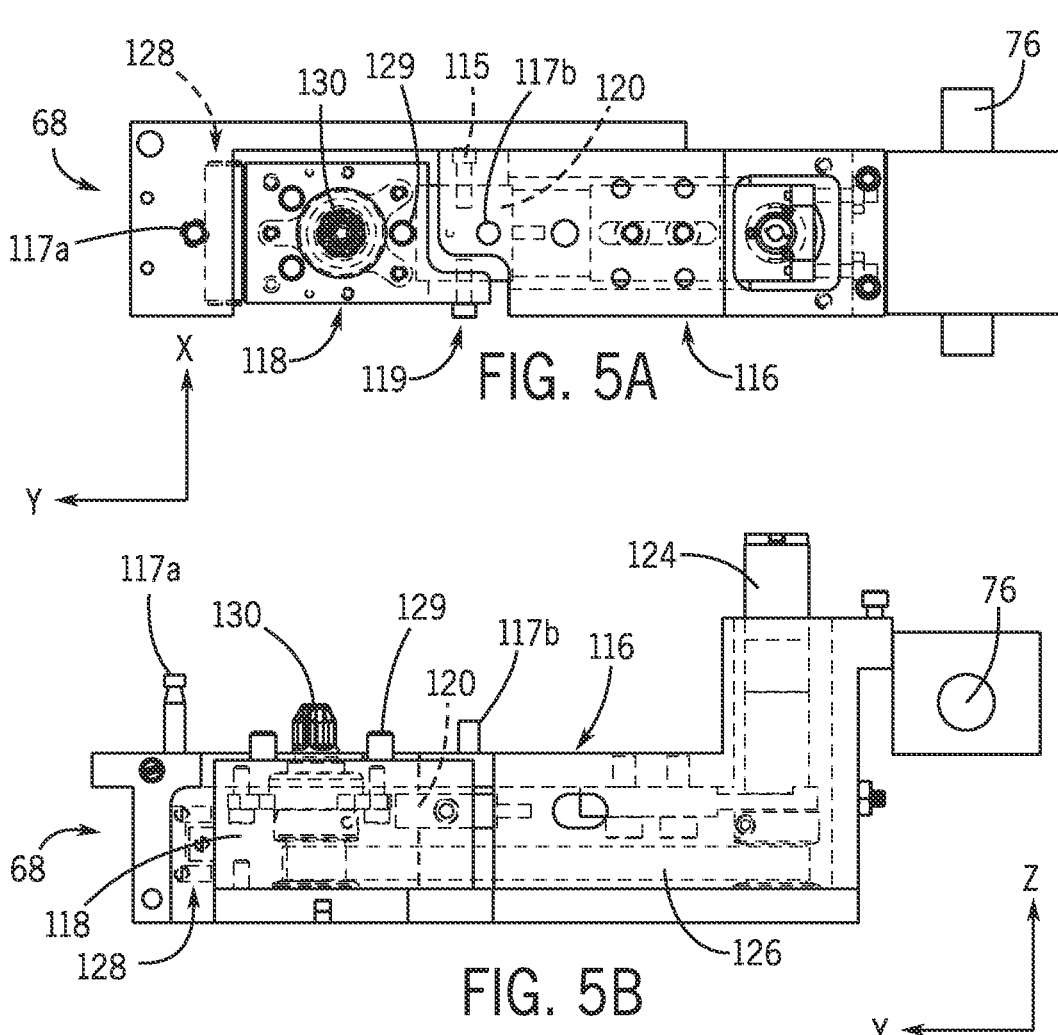
FIG. 5A
FIG. 5B
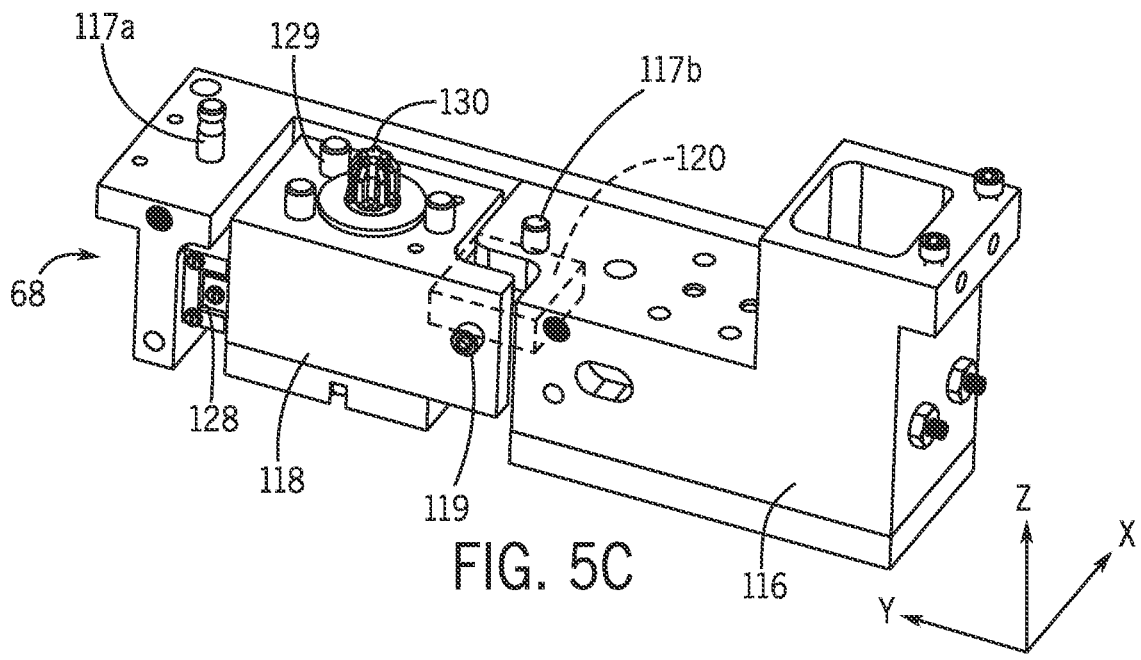
FIG. 5C

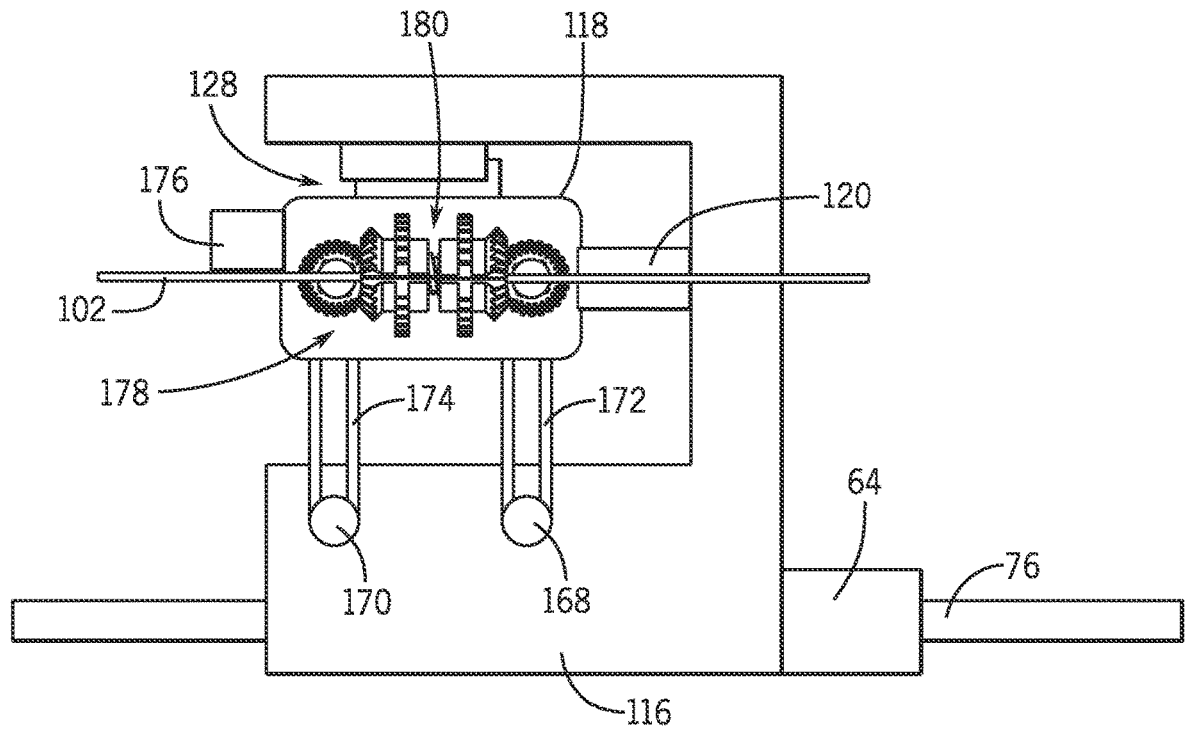
FIG. 8
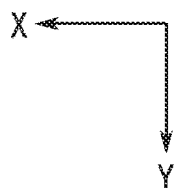

LOAD SENSING OF ELONGATED MEDICAL DEVICE IN ROBOTIC ACTUATION

CROSS-REFERENCE TO RELATED PATENT APPLICATIONS

This application is a continuation of U.S. application Ser. No. 17/597,456, filed Jan. 6, 2022, which is a 371 National Phase Application of PCT Application No. PCT/US2020/041904, filed Jul. 14, 2020, which claims the benefit of U.S. provisional application No. 62/876,489 filed Jul. 19, 2019 and claims the benefit of U.S. provisional application No. 63/012,607 filed Apr. 20, 2020, all of which are incorporated herein by their reference in their entirety.

FIELD

The present invention relates generally to the field of robotic medical procedure systems and, in particular, to apparatuses and methods for sensing a load applied to an elongated medical device in robotic actuation.

BACKGROUND

Catheters and other elongated medical devices (EMDs) may be used for minimally invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters. The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

SUMMARY

An apparatus includes a drive module having a drive module base component and a load-sensed component. An elongated medical device (EMD) is removably coupled to an isolated component. The isolated component is isolated from an external load other than an actual load acting on the EMD. The isolated component is removably coupled to the load-sensed component. A load sensor is secured to the drive module base component and the load-sensed component sensing the actual load acting on the EMD.

In one embodiment an apparatus includes a drive module including a drive module base component and a load-sensed component and a cassette removably secured to the drive module. The cassette includes a housing and a floating member movable within the housing. An EMD is manipulated by the floating member. The floating member is isolated from extremal loads other than an actual load acting on the EMD. The floating member is operatively connected to the load-sensed component and a load sensor is secured to the drive module base component and the load-sensed component sensing the actual load acting on the EMD.

In one embodiment an apparatus includes a collet having a first portion having a first collet coupler connected thereto and a second portion having a second collet coupler connected thereto. An EMD is removably located within a pathway defined by the collet. A drive module includes a first actuator operatively coupled to the first collet coupler to operatively pinch and unpinch the EMD in the pathway and to rotate the EMD and a second actuator operatively engaging the second collet coupler. A first load sensor determines the torque acting on the first collet coupler and a processor determines a torque acting on the EMD as a function of a first signal from the first load sensor.

In one embodiment an apparatus for calibrating a load sensor includes a drive module including a drive module base component, a load-sensed component, a load sensor and an elastic member having a known stiffness, the elastic member is intermediate the load sensor and the drive module base component. A cassette is removably secured to the drive module, the cassette includes a housing and a floating member movable within the housing; the cassette is configured to receive an elongated medical device.

In one embodiment a catheter-based procedure system includes a robotic drive through which extends an elongated medical device (EMD) that is removably located and manipulated within a pathway of the robotic drive. The system includes one or more sensors for determining loads acting on the proximal end of the EMD as the system advances, retracts, rotates, and fixes the EMD in intervention procedures. The loads include forces and torques that act on the EMD. A processor determines the loads acting on the EMD as a function of signals from one or more sensors in the system. In one embodiment the processor determines the loads acting on the EMD in a robotic drive with reset motion of the EMD.

In one embodiment the system includes auto-calibration of one or more sensors by known deflections of an elastic member. In one embodiment the system protects the sensor from overload. In one embodiment the system includes a processor that determines the loads acting on the EMD in a robotic drive with reset motion of the EMD, auto-calibration of one or more sensors by known deflections of elastic members, and protection of one or more sensors from overload.

In one embodiment an apparatus includes a first drive module having a first on-device adapter operatively engaging an elongated medical device (EMD) to manipulate the EMD. The drive module includes a first load sensor to measure a load applied by the first drive module to the EMD. A second drive module having a second on-device adapter releasably engages the EMD. A reset state includes moving the first on-device adapter relative to the second drive module between an extended position and a reset position. A second load sensor is operatively connected to the second on-device adapter and second drive module. A processor receives a first signal from the first load sensor and a second signal from the second load sensor and determines the actual load on the EMD as a function of the first signal, second signal and the state of the first on-device adapter and the state of the second on-device adapter.

BRIEF DESCRIPTION OF THE DRAWINGS

FIG. 5A is a top view of a drive module with a load sensing system including an actuator to rotate and/or pinch/unpinch an EMD located outside the load-sensed component and bearing support of load-sensed component in at least one off-axis (non-measured) direction.

FIG. 5B is a side view of a drive module with a load sensing system including an actuator to rotate and/or pinch/unpinch an EMD located outside the load-sensed component and bearing support of load-sensed component in at least one off-axis (non-measured) direction.

FIG. 5C is an isometric view of a drive module including a load-sensed component and a drive module base component.

FIG. 8 is a schematic top view of a load sensing system that includes a double bevel gear drive mechanism.

DETAILED DESCRIPTION OF THE EXAMPLE EMBODIMENTS

Figure 1:
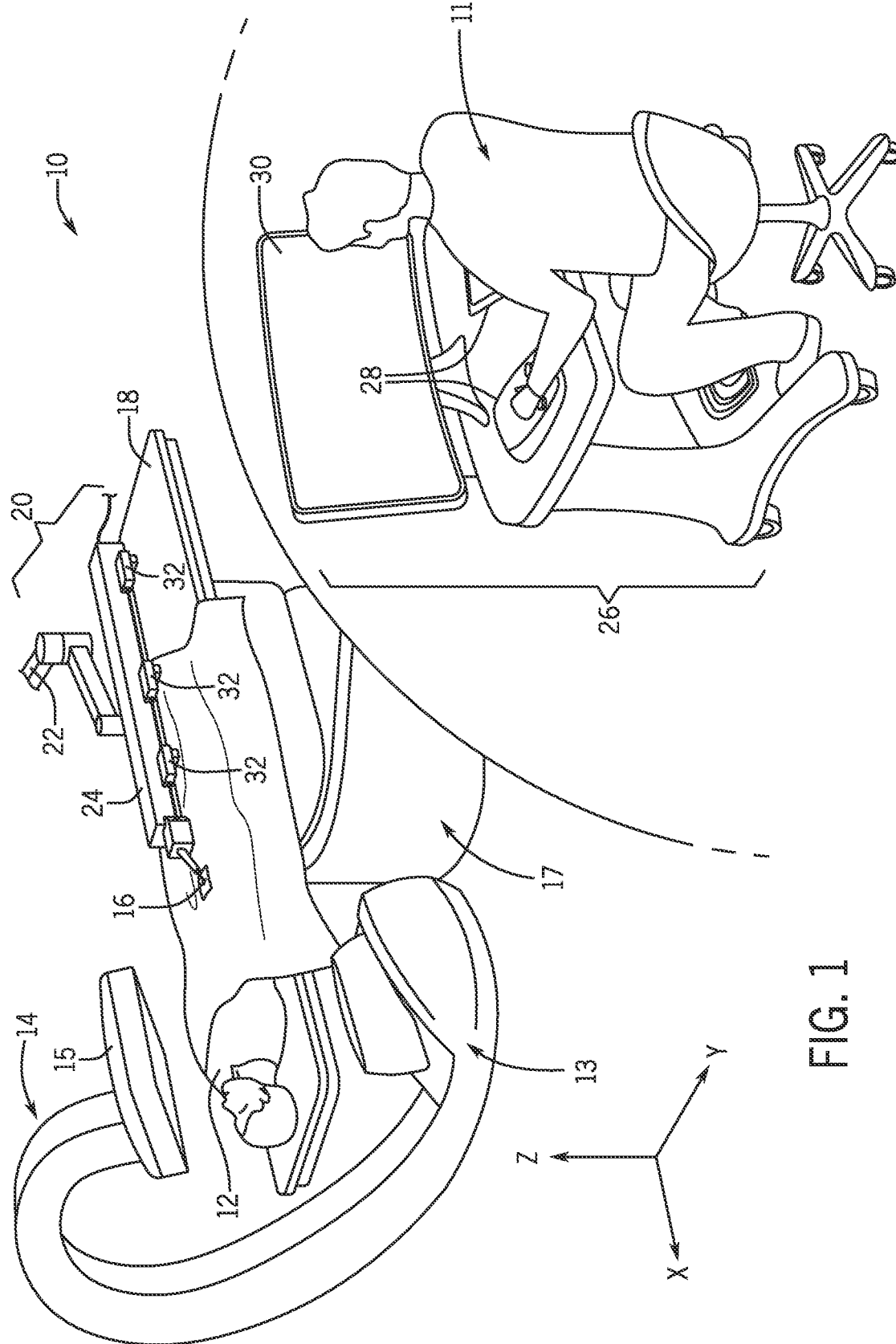
FIG. 1 is a schematic view of an exemplary catheter-based procedure system in accordance with an embodiment.

FIG. 1 is a perspective view of an exemplary catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station 26. Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, a rail on the patient table 18, a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow the user or operator 11 to perform a catheter-based medical procedure via a robotic system by operating various controls such as the controls and inputs located at the control station 26. Bedside unit 20, and in particular robotic drive 24, may include any number and/or combination of components to provide bedside unit 20 with the functionality described herein. A user or operator 11 at control station 26 is referred to as the control station user or control station operator and referred to herein as user or operator. A user or operator at bedside unit 20 is referred to as bedside unit user or bedside unit operator. The robotic drive 24 includes a plurality of device modules 32a-d mounted to a rail or linear member 60 (shown in FIG. 3). The rail or linear member 60 guides and supports the device modules. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with control station 26, allowing signals generated by the user inputs of control station 26 to be transmitted wirelessly or via hardwire to bedside unit 20 to control various functions of bedside unit 20. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. Control station 26 or other similar control system may be located either at a local site (e.g., local control station 38 shown in FIG. 2) or at a remote site (e.g., remote control station and computer system 42 shown in FIG. 2). Catheter procedure system 10 may be operated by a control station at the local site, a control station at a remote site, or both the local control station and the remote control station at the same time. At a local site, user or operator 11 and control station 26 are located in the same room or an adjacent room to the patient 12 and bedside unit 20. As used herein, a local site is the location of the bedside unit 20 and a patient 12 or subject (e.g., animal or cadaver) and the remote site is the location of a user or operator 11 and a control station 26 used to control the bedside unit 20 remotely. A control station 26 (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

Control station 26 generally includes one or more input modules 28 configured to receive user inputs to operate various components or systems of catheter-based procedure system 10. In the embodiment shown, control station 26 allows the user or operator 11 to control bedside unit 20 to perform a catheter-based medical procedure. For example, input modules 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include one or more touch screens, joysticks, scroll wheels, and/or buttons.

In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance. Device selection buttons allow the user or operator 11 to select which of the percutaneous intervention devices loaded into the robotic drive 24 are controlled by input modules 28. Automated move buttons are used to enable algorithmic movements that the catheter-based procedure system 10 may perform on a percutaneous intervention device without direct command from the user or operator 11. In one embodiment, input modules 28 may include one or more controls or icons (not shown) displayed on a touch screen (that may or may not be part of a display 30), that, when activated, causes operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Control station 26 may include a display 30. In other embodiments, the control station 26 may include two or more displays 30. Display 30 may be configured to display information or patient specific data to the user or operator 11 located at control station 26. For example, display 30 may be configured to display image data (e.g., X-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with control station 26. In one embodiment, imaging system 14 may include a C-arm (shown in FIG. 1) that allows imaging system 14 to partially or completely rotate around patient 12 in order to obtain images at different angular positions relative to patient 12

(e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure. The image or images may be displayed on display 30. For example, images may be displayed on display 30 to allow the user or operator 11 to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
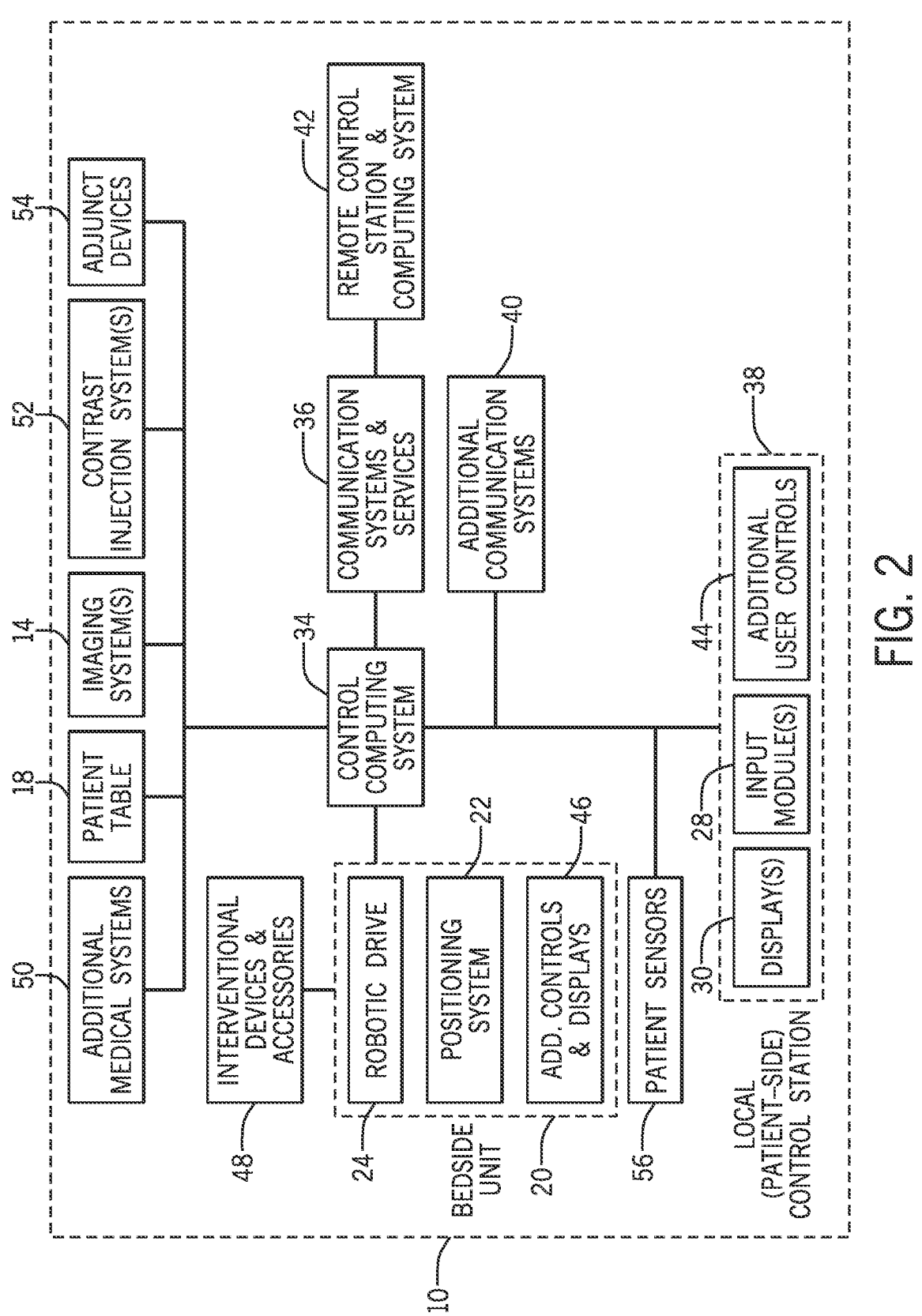
FIG. 2 is a schematic block diagram of an exemplary catheter-based procedure system in accordance with an embodiment.

FIG. 2 is a block diagram of catheter-based procedure system 10 in accordance with an exemplary embodiment. Catheter-procedure system 10 may include a control computing system 34. Control computing system 34 may physically be, for example, part of control station 26 (shown in FIG. 1). Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input modules 28 (e.g., of a control station 26 (shown in FIG. 1) such as a local control station 38 or a remote control station 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images. In another embodiment, a foot input device may be config-ured to allow the user to select which devices are mapped to scroll wheels included in input modules 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption sys-tems, systems to restrict access or use of catheter-based procedure system 10, etc.

Figure 3:
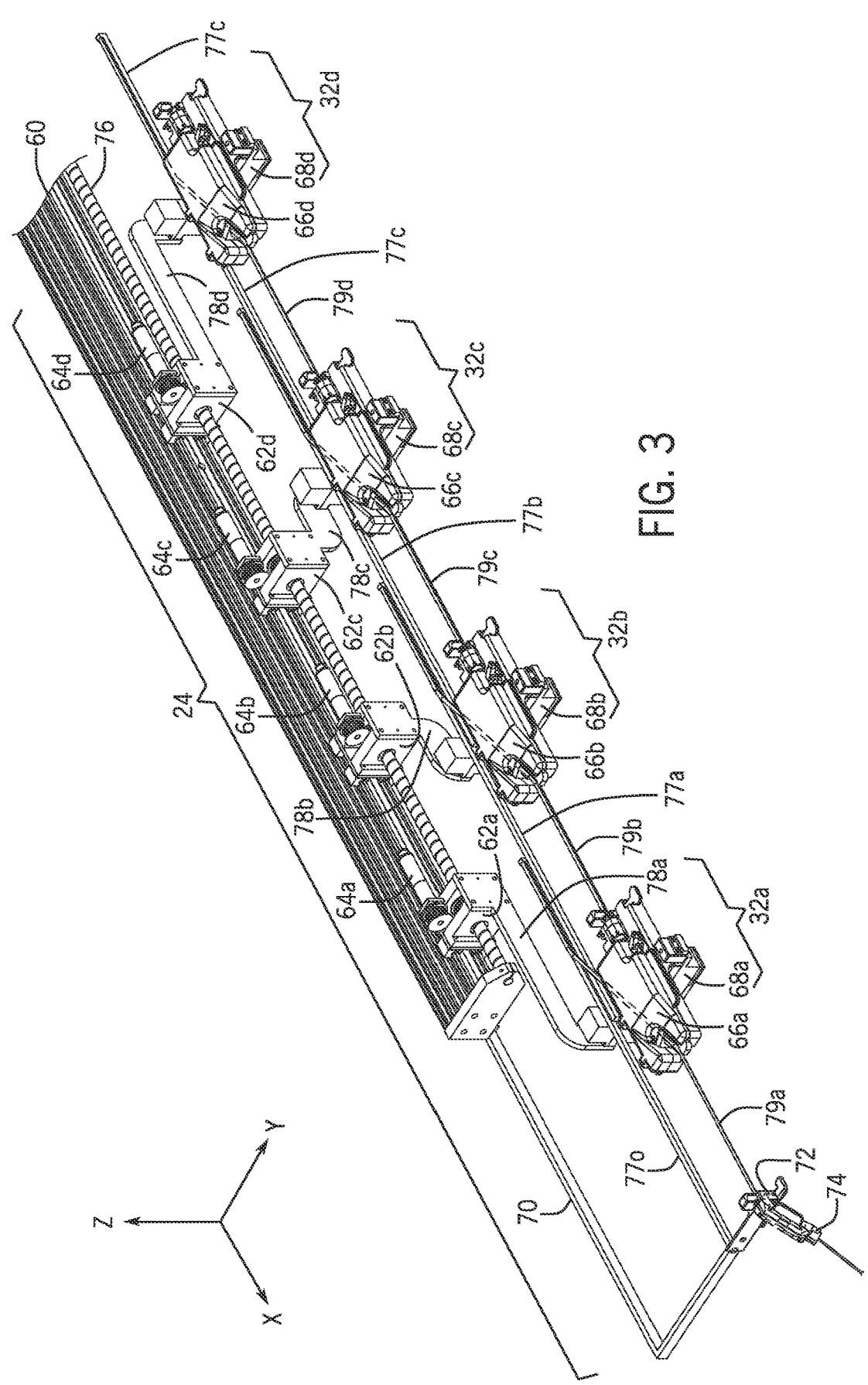
FIG. 3 is an isometric view of an exemplary bedside system of a catheter-based procedure system in accordance with an embodiment.

As mentioned, control computing system 34 is in com-munication with bedside unit 20 which includes a robotic drive 24, a positioning system 22 and may include additional controls and displays 46, and may provide control signals to the bedside unit 20 to control the operation of the motors and drive mechanisms used to drive the percutaneous interven-tion devices (e.g., guidewire, catheter, etc.). The various drive mechanisms may be provided as part of a robotic drive 24. FIG. 3 is a perspective view of a robotic drive for a catheter-based procedure system 10 in accordance with an embodiment. In FIG. 3, a robotic drive 24 includes multiple device modules 32*a-d* coupled to a linear member 60. Each device module 32*a-d* is coupled to the linear member 60 via a stage 62*a-d* moveably mounted to the linear member 60. A device module 32*a-d* may be connected to a stage 62*a-d* using a connector such as an offset bracket 78*a-d*. In another embodiment, the device module 32*a-d* is directly mounted to the stage 62*a-d*. Each stage 62*a-d* may be independently actuated to move linearly along the linear member 60. Accordingly, each stage 62*a-d* (and the corresponding device module 32*a-d* coupled to the stage 62*a-d*) may independently move relative to each other and the linear member 60. A drive mechanism is used to actuate each stage 62*a-d*. In the embodiment shown in FIG. 3, the drive mechanism includes independent stage translation motors 64*a-d* coupled to each stage 62*a-d* and a stage drive mecha-nism 76, for example, a lead screw via a rotating nut, a rack via a pinion, a belt via a pinion or pulley, a chain via a sprocket, or the stage translation motors 64*a-d* may be linear motors themselves. In some embodiments, the stage drive mechanism 76 may be a combination of these mechanisms, for example, each stage 62*a-d* could employ a different type of stage drive mechanism. In an embodiment where the stage drive mechanism is a lead screw and rotating nut, the lead screw may be rotated and each stage 62*a-d* may engage and disengage from the lead screw to move, e.g., to advance or retract. In the embodiment shown in FIG. 3, the stages 62*a-d* and device modules 32*a-d* are in a serial drive configuration.

Each device module 32*a-d* includes a drive module 68*a-d* and a cassette 66*a-d* mounted on and coupled to the drive module 68*a-d*. In the embodiment shown in FIG. 3, each cassette 66*a-d* is mounted to the drive module 68*a-d* in a vertical orientation. In other embodiments, each cassette 66*a-d* may be mounted to the drive module 68*a-d* in other mounting orientations. Each cassette 66*a-d* is configured to interface with and support a proximal portion of an EMD (not shown). In addition, each cassette 66*a-d* may include elements to provide one or more degrees of freedom in addition to the linear motion provided by the actuation of the corresponding stage 62*a-d* to move linearly along the linear member 60. For example, the cassette 66*a-d* may include elements that may be used to rotate the EMD when the cassette is coupled to the drive module 68*a-d*. Each drive module 68*a-d* includes at least one coupler to provide a drive interface to the mechanisms in each cassette 66*a-d* to provide the additional degree of freedom. Each cassette 66*a-d* also includes a channel in which a device support 79*a-d* is positioned, and each device support 79*a-d* is used to prevent an EMD from buckling. A support arm 77*a*, 77*b*, and 77*c* is attached to each device module 32*a*, 32*b*, and 32*c*, respectively, to provide a fixed point for support of a proximal end of the device supports 79*b*, 79*c*, and 79*d*, respectively. The robotic drive 24 may also include a device support connection 72 connected to a device support 79, a distal support arm 70 and a support arm 77*o*. Support arm 77*o* is used to provide a fixed point for support of the proximal end of the distal most device support 79*a* housed in the distal most device module 32*a*. In addition, an introducer interface support (redirector) 74 may be con-nected to the device support connection 72 and an EMD (e.g., an introducer sheath). The configuration of robotic drive 24 has the benefit of reducing volume and weight of the drive robotic drive 24 by using actuators on a single linear member.

To prevent contaminating the patient with pathogens, healthcare staff use aseptic technique in a room housing the bedside unit 20 and the patient 12 or subject (shown in FIG. 1). A room housing the bedside unit 20 and patient 12 may be, for example, a cath lab or an angio suite. Aseptic technique consists of using sterile barriers, sterile equip-ment, proper patient preparation, environmental controls and contact guidelines. Accordingly, all EMDs and inter-ventional accessories are sterilized and can only be in contact with either sterile barriers or sterile equipment. In an embodiment, a sterile drape (not shown) is placed over the non-sterile robotic drive 24. Each cassette 66*a-d* is sterilized and acts as a sterile interface between the draped robotic drive 24 and at least one EMD. Each cassette 66*a-d* can be designed to be sterile for single use or to be re-sterilized in whole or part so that the cassette 66*a-d* or its components can be used in multiple procedures.

Definitions & Terminology

EMD: The term elongated medical device (EMD) refers to, but is not limited to, catheters (e.g., guide catheters, microcatheters, balloon/stent catheters), wire-based devices (e.g., guidewires, embolization coils, stent retrievers, etc.), and medical devices comprising any combination of these.

Load: The term load refers to forces, torques, or combi-nation of forces and torques. The load may include a single component of force (a force along a single axis) or multiple components of forces (multi-axial forces) and/or a single component of torque (a torque around a single axis) or multiple components of torque (multi-axial torque). The load may be static (not change with time) or dynamic (change with time).

Force: The term force refers to an agent which causes or tends to cause motion of a body. A force acting on a body may change the motion of the body, retard the motion of the body, balance the forces already acting on the body, and give rise to internal stresses in the body. Characteristics of a force include the magnitude of the force, the line of action of the force (the axis along which the force acts), the direction of the force (corresponding to compressive or tensile force), and the point at which the force is acting.

Torque: The term torque refers to an agent which causes or tends to cause rotational motion of a physical body. A torque acting on a body may change the rotational motion of the body, retard the rotational motion of the body, balance the torques already acting on the body, and give rise to internal stresses in the body. Characteristics of a torque include the magnitude of the torque, the line of action of the torque, the direction of the torque (clockwise or counterclockwise about the line of action), and the point at which the torque is acting. The term torque is also referred to as moment, moment of force, rotational force, twisting force, and "turning effect". Torque is the rotational equivalent of force. The magnitude of the torque can also be determined as the product of the magnitude of the force and the perpendicular distance of the line of action of force from the axis of rotation.

Control Computing System: The term control computing system includes a processor having a processing circuit. The processor includes a central purpose processor, application specific processors (ASICs), circuits containing one or more processing components, groups of distributed processing components, groups of distributed computers configured for processing, etc. configured to provide the functionality of module or subsystem components discussed herein. Memory units (e.g., memory device, storage device, etc.) are devices for storing data and/or computer code for completing and/or facilitating the various processes described in the present disclosure. Memory units may include volatile memory and/or non-volatile memory. Memory units may include database components, object code components, script components, and/or any other type of information structure for supporting the various activities described in the present disclosure. According to an exemplary embodiment, any distributed and/or local memory device of the past, present, or future may be utilized with the systems and methods of this disclosure. According to an exemplary embodiment, memory units are communicably connected to one or more associated processing circuit. This connection may be via a circuit or any other wired, wireless, or network connection and includes computer code for executing one or more processes described herein. A single memory unit may include a variety of individual memory devices, chips, disks, and/or other storage structures or systems. Module or subsystem components may be computer code (e.g., object code, program code, compiled code, script code, executable code, or any combination thereof) for conducting each module's respective functions.

Distal and Proximal: The terms distal and proximal define relative locations of two different features. With respect to a robotic drive the terms distal and proximal are defined by the position of the robotic drive in its intended use relative to a patient.

When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient. Similarly, the proximal feature is the feature that is farther from the patient than the distal feature when the robotic drive in its intended in-use position.

When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction. Referring to FIG. 1, a robotic device is shown from the viewpoint of an operator facing a patient. In this arrangement, the distal direction is along the positive X coordinate axis and the proximal direction is along the negative X coordinate axis. Referring to FIG. 3, the EMD is moved in a distal direction on a path toward a patient through the introducer interface support 74 which defines the distal end of the robotic drive 24. The proximal end of the robotic drive 24 is the point furthest from the distal end along the negative X axis.

Longitudinal Axis: The term longitudinal axis of a member (for example, an EMD or other element in the catheter-based procedure system) is the line or axis along the length of the member that passes through the center of the transverse cross section of the member in the direction from a proximal portion of the member to a distal portion of the member. For example, the longitudinal axis of a guidewire is the central axis in the direction from a proximal portion of the guidewire toward a distal portion of the guidewire even though the guidewire may be non-linear in the relevant portion.

Axial and Rotational Movement: The term axial movement of a member refers to translation of the member along the longitudinal axis of the member. When the distal end of an EMD is axially moved in a distal direction along its longitudinal axis into or further into the patient, the EMD is being advanced. When the distal end of an EMD is axially moved in a proximal direction along its longitudinal axis out of or further out of the patient, the EMD is being withdrawn. The term rotational movement of a member refers to the change in angular orientation of the member about the local longitudinal axis of the member. Rotational movement of an EMD corresponds to clockwise or counterclockwise rotation of the EMD about its longitudinal axis due to an applied torque.

Axial and Lateral Insertion: The term axial insertion refers to inserting a first member into a second member along the longitudinal axis of the second member. The term lateral insertion refers to inserting a first member into a second member along a direction in a plane perpendicular to the longitudinal axis of the second member. This can also be referred to as radial loading or side loading.

Pinch/Unpinch: The term pinch refers to releasably fixing an EMD to a member such that the EMD and member move together when the member moves. The term unpinch refers to releasing the EMD from a member such that the EMD and member move independently when the member moves.

Clamp/Unclamp: The term clamp refers to releasably fixing an EMD to a member such that the EMD's movement is constrained with respect to the member. The member can be fixed with respect to a global coordinate system or with respect to a local coordinate system. The term unclamp refers to releasing the EMD from the member such that the EMD can move independently.

Grip/Ungrip: The term grip refers to the application of a force or torque to an EMD by a drive mechanism that causes motion of the EMD without slip in at least one degree of freedom. The term ungrip refers to the release of the application of the force or torque to the EMD by a drive mechanism such that the position of the EMD is no longer constrained. An EMD gripped between two tires rotates about its longitudinal axis when the tires move longitudinally relative to one another. The rotational movement of the EMD is different than the movement of the two tires. The position of an EMD that is gripped is constrained by the drive mechanism.

Buckling: The term buckling refers to the tendency of a flexible EMD when under axial compression to bend away from the longitudinal axis or intended path along which it is being advanced. In one embodiment axial compression occurs in response to resistance from being navigated in the vasculature. The distance an EMD may be driven along its longitudinal axis without support before the EMD buckles is referred to herein as the device buckling distance. The device buckling distance is a function of the device's stiffness, geometry (including but not limited to diameter), and force being applied to the EMD. Buckling may cause the EMD to form an arcuate portion different than the intended path. Kinking is a case of buckling in which deformation of the EMD is non-elastic resulting in a permanent set.

Homing: The term homing refers to moving a member to a defined position. An example of a defined position is a reference position. Another example of a defined position is an initial position. The term home refers to the defined position. It is normally used as a reference for subsequent linear or rotational positions.

Top/Bottom, Up/Down, Front/Rear, Inwardly/Outwardly: The terms top, up, and upper refer to the general direction away from the direction of gravity and the terms bottom, down, and lower refer to the general direction in the direction of gravity. The term front refers to the side of the robotic drive that faces a bedside user and away from the positioning system, such as the articulating arm. The term rear refers to the side of the robotic drive that is closest to the positioning system, such as the articulating arm. The term inwardly refers to the inner portion of a feature. The term outwardly refers to the outer portion of a feature.

Stage: The term stage refers to a member, feature, or device that is used to couple a device module to the robotic drive. For example, the stage may be used to couple the device module to a rail or linear member of the robotic drive.

Drive Module: The term drive module generally refers to the part (e.g., the capital part) of the robotic drive system that normally contains one or more motors with drive couplers that interface with the cassette.

Device Module: The term device module refers to the combination of a drive module and a cassette.

Cassette: The term cassette generally refers to the part (non-capital, consumable or sterilizable unit) of the robotic drive system that normally is the sterile interface between a drive module and at least one EMD (directly) or through a device adapter (indirectly).

Collet: The term collet refers to a device that can releasably fix a portion of an EMD. The term fixed here means no intentional relative movement of the collet and EMD during operation. In one embodiment the collet includes at least two members that move rotationally relative to each other to releasably fix the EMD to at least one of the two members.

In one embodiment the collet includes at least two members that move axially (along a longitudinal axis) relative to each other to releasably fix the EMD to at least one of the two members. In one embodiment the collet includes at least two members that move rotationally and axially relative to each other to releasably fix the EMD to at least one of the two members.

Fixed: The term fixed means no intentional relative movement of a first member with respect to a second member during operation.

On-Device Adapter: The term on-device adapter refers to a sterile apparatus capable of releasably pinching an EMD to provide a driving interface. The on-device adapter is also known as an end-effector or EMD capturing device. In one non-limiting embodiment the on-device adapter is a collet that is operatively controlled robotically to rotate the EMD about its longitudinal axis, to pinch and/or unpinch the EMD to the collet, and/or to translate the EMD along its longitudinal axis. In one embodiment the on-device adapter is a hub-drive mechanism such as a driven gear located on the hub of an EMD.

Tandem Drive: The term tandem drive refers to a drive unit or subsystem within the robotic drive containing two or more EMD drive modules, capable of manipulating one or more EMDs.

Hub (Proximal) Driving: The term hub driving or proximal driving refers to holding on to and manipulating an EMD from a proximal position (e.g., a geared adapter on a catheter hub). In one embodiment, hub driving refers to imparting a force or torque to the hub of a catheter to translate and/or rotate the catheter. Hub driving may cause the EMD to buckle and thus hub driving often requires anti-buckling features. For devices that do not have hubs or other interfaces (e.g., a guidewire), device adapters may be added to the device to act as an interface for the device module. In one embodiment, an EMD does not include any mechanism to manipulate features within the catheter such as wires that extend from the handle to the distal end of the catheter to deflect the distal end of the catheter.

Shaft (Distal) Driving: The term shaft (distal) driving refers to holding on to and manipulating an EMD along its shaft. The on-device adapter is normally placed just proximal of the hub or Y-connector the device is inserted into. If the location of the on-device adapter is at the proximity of an insertion point (to the body or another catheter or valve), shaft driving does not typically require anti-buckling features. (It may include anti-buckling features to improve drive capability.)

Sterilizable Unit: The term sterilizable unit refers to an apparatus that is capable of being sterilized (free from pathogenic microorganisms). This includes, but is not limited to, a cassette, consumable unit, drape, device adapter, and sterilizable drive modules/units (which may include electromechanical components). Sterilizable Units may come into contact with the patient, other sterile devices, or anything else placed within the sterile field of a medical procedure.

Sterile Interface: The term sterile interface refers to an interface or boundary between a sterile and non-sterile unit. For example, a cassette may be a sterile interface between the robotic drive and at least one EMD.

Reset (drive mechanism reset): The term reset means repositioning a drive mechanism from a first position to a second position to allow for continued rotational and/or axial movement of an EMD. During reset, the EMD is not actively being moved by the drive mechanism. In one embodiment the EMD is released by the drive mechanism prior to repositioning the drive mechanism. In one embodiment a clamp fixes the location of the EMD during repositioning of the drive mechanism.

Continuous Motion: The term continuous motion refers to motion that does not require a reset and is uninterrupted. Tire drive linear motion is continuous motion.

Discrete Motion: The term discrete motion refers to motion that requires a reset and is interrupted. Paddle drive linear motion is discrete motion.

Consumable: The term consumable refers to a sterilizable unit that normally has a single use in a medical procedure. The unit could be a reusable consumable through a re-sterilization process for use in another medical procedure.

Device Support: The term device support refers to a member, feature, or device that prevents an EMD from buckling.

Double-Gear: The term double-gear refers to two independently driven gears operatively connected to two different portions of a device. Each of the two gears may be identical or different design. The term gear may be a bevel gear, spiral bevel gear, spur gear, miter gear, worm gear, helical gear, rack and pinon, screw gear, internal gear such as a sun gear, involute spline shafts and bushing, or any other type of gears known in the art. In one embodiment, double-gear also includes devices in which any drive connection is maintained by two different portions of a device, including but not limited to a belt, friction engagement or other couplers known in the art.

Load Sensor: The term load sensor refers to a sensor that measures one or more components of force and/or torque. For example, a uniaxial load sensor measures force along one axis or torque about one axis. A multiaxial load sensor measures force and/or torque in multiple mutually orthogonal axes. A load sensor generally generates electrical signals in response to load (for example, a strain gauge based load sensor generates charge in response to load) and generally requires signal conditioning circuitry to convert the signals to force and/or torque. As such, a load sensor is a transducer that converts one or more components of compressive and/or tensile force and/or clockwise and/or counterclockwise torque into a measurable electrical output (for example, voltage or current).

Motion Sensor: The term motion sensor refers a sensor that detects motion parameters. Contact motion sensors include, but are not limited to, accelerometers, LVDTs, encoders. Contactless motion sensors include but are not limited to CMOS sensors, optical encoders, ultrasonic sensors, standard or high-speed cameras.

Zero-Offset: The term zero-offset refers to the bias in the measured load of a load sensing system indicating an apparent load when no load is applied. The process of sensor calibration corrects for the zero-offset such that when no load is applied the load sensing system indicates zero load.

Overload Protection: The term overload protection refers to any means of protecting a load sensor from being overloaded, that is, being exposed to forces beyond the operating range of the sensor or causing damage due to loads that exceed the upper limits of the sensor measurement specifications.

Automatic Calibration: The term automatic calibration, or automated calibration, or auto-calibration, refers to any means of calibration of a sensor or sensor system that occurs without manual intervention. In automatic calibration, a load sensor or load sensing system may be acted upon by known loads (that is, by loads accurately known by another method)

by non-manual means (such as driven motors displacing an elastic member of known stiffness) and a processor is used to correct for any errors.

Load Sensing

To sense force and torque acting on a mechanical component with an elongated cylindrical portion, a sensor is placed in-line with the elongated cylindrical portion or a strain gauge is attached on the elongated cylindrical portion. In interventional catheter and guidewire systems where the elongated cylindrical device is an elongated medical device (EMD), it may be desirable to measure forces and torques (hereafter referred to as loads) outside of the patient where the sensor is not in line with or attached to the EMD. Measuring loads outside of the patient removes the requirement for placing the sensor and related electronics (e.g. cables) inside the blood vessels. While placement of load sensors inside the blood vessels is possible, such as for larger diameter EMDs (e.g. some EP (electrophysiology) catheters with >2 mm diameter), it may be desirable to measure loads when smaller diameter EMDs with diameters between 0.2 mm and 2 mm are used without sensors that would be required to be placed within the blood vessels. In manual procedures, the physician relies on his/her fingers to estimate loads. However, for the low range of forces and torques that EMDs carry it is very difficult for the physician to estimate the loads accurately given the small diameter of the devices.

In a robotic system, the forces and torques acting on the EMD can be measured using a load sensor inside the robotic drive mechanism. By placing the sensor inside the drive mechanism, parasitic forces and torques due to frictional and inertial effects may corrupt (e.g., be added to) the actual values and thereby may reduce the accuracy of measurement of force and torque in the EMD. Herein, methods and designs are presented to implement load-sensing in robotic vascular intervention systems while the parasitic loads acting on the load sensor are reduced. In other words, the load-sensed component is isolated from parasitic loads so that the difference between the measured load and actual load is minimal.

The load sensing system described herein can be used in connection with the system described in pending application entitled: SYSTEMS, APPARATUS AND METHODS FOR SUPPORTING AND DRIVING ELONGATED MEDICAL DEVICES IN A ROBOTIC CATHETER-BASED PROCEDURE SYSTEM (U.S. Provisional Application No. 62/874,222, filed Jul. 15, 2019. The floating cassette member is described therein. The anti-buckling support systems (telescopic-type supports, accordion-type supports, fixed sheaths, etc.) used in collet driving as well as tubing may apply an unintentional force (parasitic force) on the disposable component which can be mixed with (or added to) the actual force acting on EMD in load-sensing measurements.

Referring to FIGS. 3 and 4A-4D a device module 32 of a robotic drive 24 includes a drive module 68 and a cassette 66 which are separated by a sterile barrier 100. In one embodiment sterile barrier 100 is a flexible drape. In one embodiment sterile barrier 100 is a rigid sterile barrier such as a box. In one embodiment drive module 68 is the capital portion of device module 32 and cassette 66 and sterile barrier 100 are disposable portions of device module 32. The robotic drive system can move an EMD 102 linearly along a longitudinal axis of the EMD and/or rotationally about a longitudinal axis of the EMD. Linear (advance, retract) motion and rotational (clockwise, counterclockwise) motion are the main degrees of freedom (DOFs) of EMD 102. There may be additional DOFs, for example, to pinch/unpinch an EMD 102 in a collet or unsheathe a self-expanding stent.

Cassette 66 includes a cassette housing 104 and a floating component 106 that is moveable within and/or relative to cassette housing 104. In one embodiment floating component 106 is isolated from the housing 104 such that the floating component 106 is not fixed to the housing 104. In one embodiment floating component 106 is connected to a tube 110 that can be used to introduce saline, contrast, etc. In one embodiment tube 110 is connected to a Y-connector or to a hub of a catheter, where tube 110 is anchored to cassette housing 104. In one embodiment cassette 66 is a disposable unit where cassette housing 104, floating component 106, and tube 110 are disposable components.

EMD 102 is manipulated by a mechanism (described below) within floating component 106. Floating component 106 is isolated from external loads other than the actual load acting on EMD 102. In one embodiment, floating component 106 of cassette 66 is connected to housing 104 of cassette 66, for example, by using a flexible membrane 108. In another example, floating component 106 of cassette 66 stays together with housing 104 of cassette 66 using a guide and slider interface. (See FIG. 6B reference numerals 150-151 and 156-157.)

In one embodiment, flexible membrane 108 does not apply a significant load on floating component 106 in load measurement directions. For example, the load applied by the flexible membrane 108 to floating component 106 is below 10% of the range of the load being measured.

In one embodiment, floating component 106 is captive, that is, contained, in housing 104 of cassette 66 so that the two components (cassette housing 104 and isolated component 106) of cassette 66 can be moved together and be mounted together on drive module 68. Once mounted on drive module 68, floating component 106 becomes contactless relative to housing 104 of cassette 66 so that no load is applied to floating component 106 from housing 104 of cassette 66. This feature is described in detail in application entitled: SYSTEMS, APPARATUS AND METHODS FOR SUPPORTING AND DRIVING ELONGATED MEDICAL DEVICES IN A ROBOTIC CATHETER-BASED PROCEDURE SYSTEM (U.S. Provisional Application No. 62/874,222, filed Jul. 15, 2019.

Referring to FIG. 3, FIGS. 4A-4D, and FIG. 5D, in one embodiment the linear DOF motion of EMD 102 is achieved by moving device module 32 along a stage drive mechanism 76 while EMD 102 is captured by an EMD on-device adapter 112 integrally connected to floating component 106 of cassette 66. EMD on-device adapter 112 is also known as an end-effector or an EMD capturing device. In one embodiment EMD on-device adapter 112 is a collet. In one embodiment EMD on-device adapter 112 is a hub drive. In one embodiment stage drive mechanism 76 is a lead screw and drive module 68 includes a stage translation motor 64 that rotates a nut on the lead screw by use of a belt 114. The nut is in contact with drive module 68 through two thrust bearings and as the nut rotates on the lead screw it translates device module 32. Drive module 68 is constrained by a guide to move only linearly with respect to stage drive mechanism 76.

Drive module 68 includes a drive module base component 116 and a load-sensed component 118. Load-sensed component 118 supports floating component 106 at least in one load measurement direction, and load-sensed component 118 is supported in at least one load measurement direction by a load sensor 120 connected to drive module base component 116. In one embodiment drive module 68 is a capital unit making drive module base component 116, load-sensed component 118, and load sensor 120 capital components.

Figure 4A:
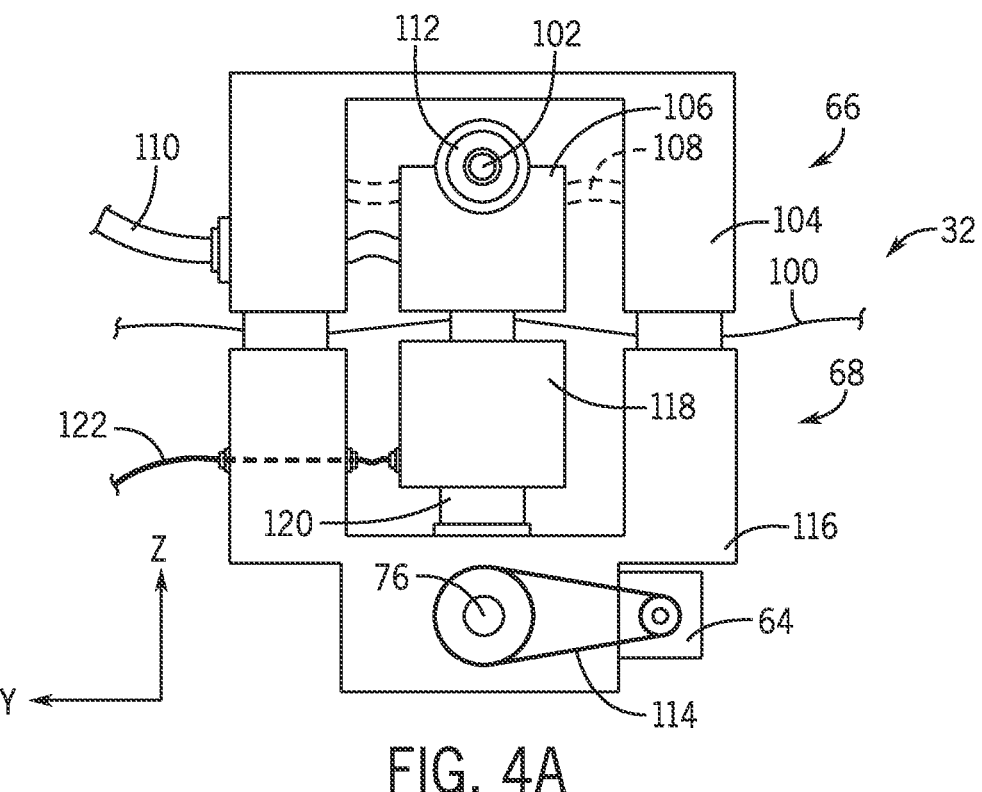
FIG. 4A is schematic end view of a device module with a load sensing system including an isolated component and a load-sensed component.
Figure 4B:
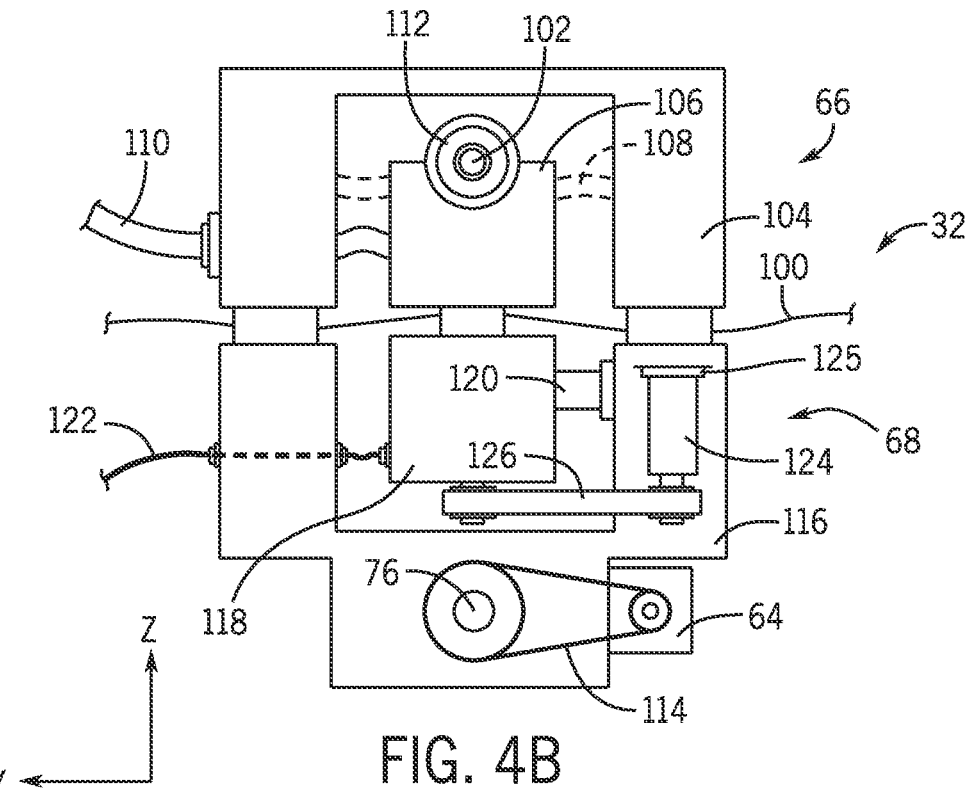
FIG. 4B is a schematic end view of another embodiment of FIG. 4A including an actuator to rotate and/or pinch/unpinch an EMD located outside the load-sensed component.
Figure 4C:
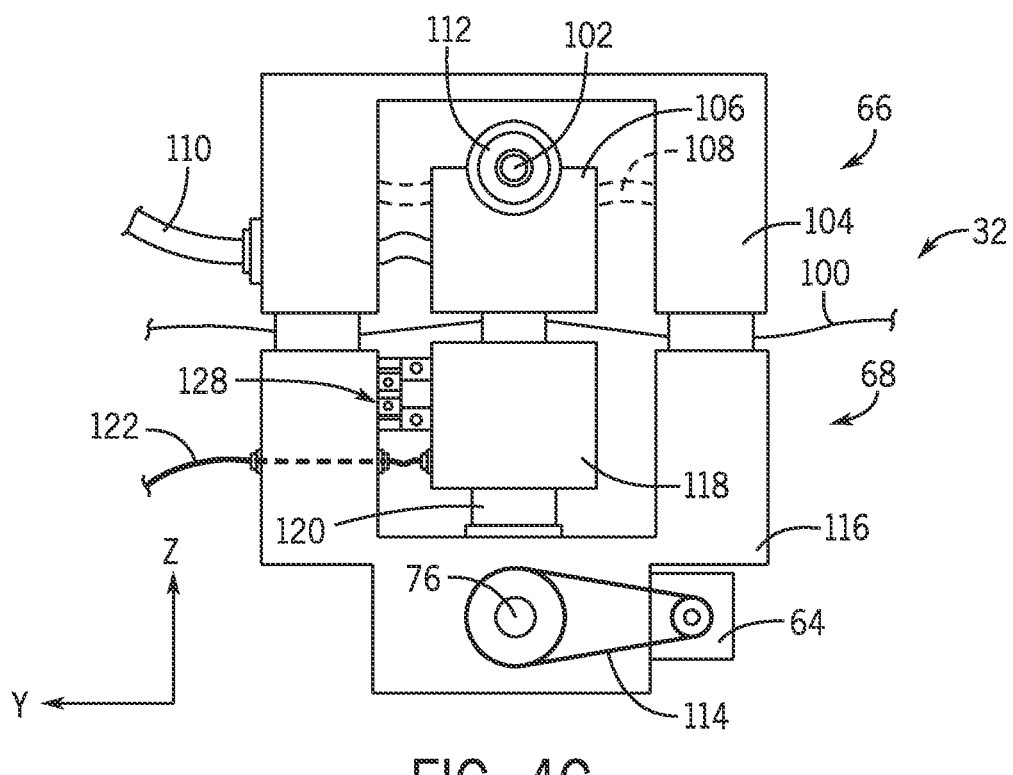
FIG. 4C is a schematic end view of another embodiment of FIG. 4A including bearing support of load-sensed component in at least one off-axis (non-measured) direction.

In one embodiment a cable 122 is connected to load-sensed component 118 where, for example, cable 122 contains wires to power actuators or to convey signals to/from encoders (e.g. FIG. 4A and FIG. 4C). In one embodiment cable 122 connected to load-sensed component 118 is anchored on drive module base component 116 to prevent cable 122 from dragging on load-sensed component 118. In one embodiment a cable 122 is connected to load-sensed component 118 through a lumen in drive module base component 116. In one embodiment cable 122 includes separate connected cables, for example, a first part being a cable connected to a connector on drive module base component 116 and a second part being a separate cable that connects a connector on drive module base component 116 to load-sensed component 118 where the second cable does not impart a significant load on load-sensed component 118 in load measurement directions. In one example, the load applied by the second cable is not considered significant if it is below 10% of the full range of load being measured.

In one embodiment load-sensed component 118 can be fully supported by load sensor 120. However, the load capacity of load sensor 120 for off-axis loads (e.g., a force component acting along an axis other than the measurement axis which is shown in the figures as the X-axis) may not be adequate to withstand loads such as the weight or inertia forces of load-sensed component 118. Normally, the structural strength of a load sensor is proportional to the load measurement range of the sensor. Since the range of loads acting on EMD 102 may be significantly lower than the weight or inertia forces of load-sensed component 118, load sensor 120 may be overloaded and damaged if the weight and/or inertia forces are fully supported by the sensor. One approach for supporting off-axis loads includes the use of a load sensor 120 having higher structural strengths in off-axis directions that can support high off-axis loads. For example, in one embodiment load sensor 120 is a bending beam sensor with these characteristics.

In one embodiment, the off-axis loads are supported by an additional component such as a bearing support. The bearing support may be used to support only off-axis loads without imparting a load in the measurement direction.

In one embodiment load-sensing can be accomplished indirectly, that is, without explicit use of load sensor 120. For example, in one embodiment load-sensing can be accomplished by measuring the electrical current of electrical actuators, which can be related to the applied force and/or torque by the actuator. In one embodiment load-sensing can be accomplished by measuring a physical property, such as pressure, of the actuators, which can be related to the applied force and/or torque. In one embodiment the relationship between a physical property and the load may be determined by experimental calibration. In one embodiment the relationship between a physical property and the load may be determined by a mathematical model or equation.

In one embodiment, the entire drive module 68 is load-sensed. As an example, the entire drive module 68 may be connected to stage 62 through a load sensor 120 and load sensor 120 supports drive module 68 in at least one direction (load measurement direction). In one embodiment, load sensor 120 is located inside drive module 68 to eliminate sources of parasitic loads from load-sensed component 118, and reduce parasitic loads such as frictional loads, inertia loads, gravity loads which corrupt the measurement of the actual loads acting on EMD 102 during the measurements.

The load-sensing system includes a processor (processing unit) that receives a signal or signals from the load sensor that is representative of the measured load.

The load-sensing system includes a method to correct for parasitic loads acting on load-sensed component 118 corrupting actual loads due to parasitic load sources in the drive system such as parasitic loads from drive module 68, cassette 66, cable 122, tube 110, and sterile barrier 100. In one embodiment sterile barrier 100 includes a drape. The method includes characterization and/or measurement of parasitic loads such as inertia loads, gravity loads, frictional loads, and drag loads. Drag loads refer to loads caused by cables and/or tubing and/or other components imparting a resistive load to load-sensed component 118. Frictional loads include, but are not limited to, frictional loads in the drive train such as frictional losses in the gears, belts, sliding components, sealings. The actual force, $F_{actual}$, and the actual torque, $T_{actual}$, acting on the EMD may be determined, respectively, as follows:

$$F_{actual}=F_{sensed}-F_{inertia}-F_{gravity}-F_{friction}-F_{drag} \qquad (1)$$

$$T_{actual}=T_{sensed}-T_{inertia}-T_{gravity}-T_{friction}-T_{drag} \qquad (2)$$

where $F_{inertia}$, $F_{gravity}$, $F_{friction}$, and $F_{drag}$ represent, respectively, parasitic inertia, gravity, friction and drag forces, and $T_{inertia}$, $T_{gravity}$, $T_{friction}$, and $T_{drag}$ represent, respectively, parasitic inertia, gravity, friction and drag torques. $F_{sensed}$ and $T_{sensed}$ refer, respectively, to the force and torque measured by the load-sensor connected to the load-sensed component.

Referring to FIGS. 4A-4D discussed herein above, in the load sensing concept indicated device module 32 includes a drive module 68 including a drive module base component 116 and a load-sensed component 118. An EMD 102 is removably coupled to an isolated component 106. The isolated component 106 is also referred to as the isolated interface component because it provides an interface between the load-sensed component 118 and EMD 102. As used herein the isolated component is also referred to as a floating member or floating component. The isolated component 106 is isolated from a load other than an actual load acting on the EMD 102. The isolated component 106 is removably coupled to the load-sensed component 118. A load sensor 120 that is secured to the drive module base component 116 and the load-sensed component 118 senses the actual load acting on the EMD 102.

In one embodiment load sensor 120 is the sole support of the load-sensed component 118 in at least one direction of load measurement. In one embodiment cassette housing 104 and isolated component 106 are internally connected so they form one component. In one embodiment a flexible membrane 108 connects cassette housing 104 and isolated component 106, where flexible membrane 108 applies negligible forces in the X-direction (device direction) to the isolated component 106. In one embodiment, flexible membrane 108 is not a physical membrane and represents the cassette interface.

Referring to FIG. 4A, device module 32 includes load-sensed component 118 that is fully supported by load sensor 120. In one embodiment load sensor 120 is a single-axis sensor measuring the reaction force to determine the actual force on EMD 102. In one embodiment load sensor 120 is a multi-axis sensor measuring components of the reaction load to determine the corresponding actual force and torque acting on EMD 102. In one embodiment there is no actuator for rotation of EMD 102 or pinching/unpinching of EMD 102. In one embodiment there is at least one actuator (not shown) for rotation of EMD 102 and/or pinching/unpinching of EMD 102 located inside or integrally connected to load-sensed component 118.

Referring to FIG. 4B, another embodiment of FIG. 4A of a device module 32 with a load-sensing system is indicated with an additional feature, that is, locating at least one actuator used to rotate EMD 102 and/or to pinch/unpinch outside the load-sensed component 118. In one embodiment said actuator 124 is moved from inside load-sensed component 118 to outside load-sensed component 118 to reduce parasitic loads (such as inertial loads) that may be imparted by the actuator on load-sensed component 118.

In one embodiment power is transferred from actuator 124 located outside of load-sensed component 118 to the drive components inside load-sensed component (for example, pulleys and/or capstans used to drive the disposable on-device adapters in the cassette) through a power train that does not impart a load in the load measurement direction on load sensor 120. In one embodiment power is transferred from actuator 124 located outside of load-sensed component 118 to the drive components inside load-sensed component 118 by using a belt 126 perpendicular to the load-measurement direction. In one embodiment power is transferred from actuator 124 located outside of load-sensed component 118 to the drive components inside load-sensed component 118 by other means, such as using a chain or cables or wires perpendicular to the load-measurement direction. In one embodiment power is transferred from actuator 124 to the EMD on-device adapter 112 through a drive train that imparts a load in the load measurement direction on load sensor 120, where this load can be corrected for in determination of actual load on EMD 102. In one embodiment actuator 124 includes a second load sensor such as a torque sensor 125 to measure reaction torque between actuator 124 and drive module base component 116. In one embodiment actuator 124 includes an encoder for device angular position feedback.

In one embodiment load sensor 120 is a force sensor such as a bending beam force sensor to measure the force acting on EMD 102. In one embodiment load sensor 120 is a multi-axis sensor used to measure the force and the torque acting on EMD 102. In one embodiment, the center line of the power train (e.g., belt, cable, chain, etc.) used to transmit power from actuator 124 for rotation or pinching/unpinching of EMD 102 to load-sensed component 118 coincides with the axis of load sensor 120 so that no torque is applied by pretension in the power train to the torque sensor in the torque measurement direction. In another embodiment, the power train is parallel to the EMD proximal portion engaged in floating component 106 so that no torque is created by pretension in the power train in a torque measurement direction.

In one embodiment a load sensor 120 is used in the powertrain between actuator 124 for rotation or pinching/unpinching of EMD 102 and EMD on-device adapter 112 to determine the torque acting on EMD 102 and/or the torque applied to pinch/unpinch a collet. In one embodiment, load sensor 120 is located between actuator 124 and drive module base component 116 to determine the torque acting on EMD 102 and/or the torque applied to pinch/unpinch a collet.

Referring to FIG. 4C, another embodiment of FIG. 4A of a device module 32 with a load-sensing system is indicated with an additional feature, that is, including a bearing 128 to support load-sensed component 118 in at least one non-measurement direction. In other words, bearing support 128 does not impart a load in the measurement direction. Referring to FIG. 4C, in one embodiment bearing support 128 is a linear bearing (directed into the plane) that supports load-sensed component 118 in all directions other than the force measurement direction.

Figure 4D:
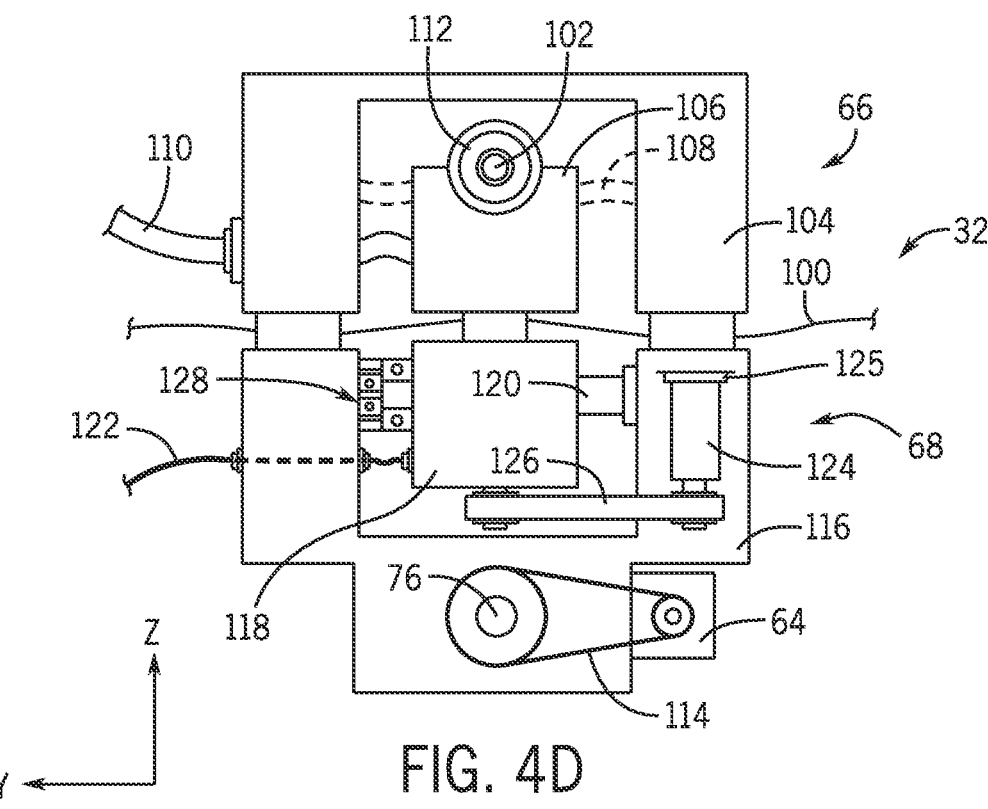
FIG. 4D is a schematic end view of another embodiment of FIG. 4A including an actuator to rotate and/or pinch/unpinch an EMD located outside the load-sensed component and bearing support of load-sensed component in at least one off-axis (non-measured) direction.

Referring to FIG. 4D, another embodiment of FIG. 4A of a device module 32 with a load-sensing system is indicated that includes the combined features of FIGS. 4B and 4C described above, that is, locating an actuator 124 for rotation of and/or pinching/unpinching of an EMD 102 outside load-sensed component 118 and including bearing support 128 of load-sensed component 118 in at least one off-axis (non-measurement) direction. Bearing support 128 does not impart a load in the measurement direction. Referring to FIG. 4D, in one embodiment bearing support 128 is a linear bearing (directed into the plane) that supports load-sensed component 118 in all directions other than the force measurement direction.

Referring to FIGS. 5A, 5B, and 5C, a drive module 68 with a load sensing system is indicated. Drive module 68 includes drive module base component 116 and load-sensed component 118 as separate parts that are connected by load sensor 120 that is located between drive module base component 116 and load-sensed component 118. Bearing 128 of load-sensed component 118 supports the load-sensed component in at least one off-axis (non-measured) direction.

Referring to FIG. 5B, drive module 68 with a load sensing system includes actuator 124 (used to rotate and/or pinch/unpinch an EMD 102) that is located outside load-sensed component 118. In one embodiment actuator 124 rotates a first pulley that drives belt 126 that rotates a second pulley that rotates a coupler 130 that can engage and disengage from cassette 66.

Referring to FIGS. 5A, 5B, 5C, 5G, and 5H, in one embodiment the drive module base component 116 includes the load-sensed component 118 and load sensor 120. As discussed herein above drive module 68 includes drive module base component 116 and load-sensed component 118 as separate parts that are connected by load sensor 120 that is located between drive module base component 116 and load-sensed component 118. Bearing 128 of load-sensed component 118 supports the load-sensed component in at least one off-axis (non-load-measured) direction. Load-sensed component 118 is located within the drive module base component 116 and secured to the drive module base component 116 with a load sensor 120. In one embodiment load sensor 120 includes a first portion secured to drive module base component 116 with a first fastener 115 and a second portion secured to load-sensed component 118 with a second fastener 119. In one embodiment the first portion of the load sensor 120 is different and distinct from the second portion of the load sensor 120. In one embodiment first fastener 115 and second fastener 119 are bolts. In one embodiment first fastener 115 and second fastener 119 are mechanical fastening components known in the art for ensuring mechanical connection. In one embodiment first fastener 115 and second fastener 119 are replaced with adhesive means for ensuring mechanical connection. In one embodiment first fastener 115 and second fastener 119 are magnets.

Figure 5D:
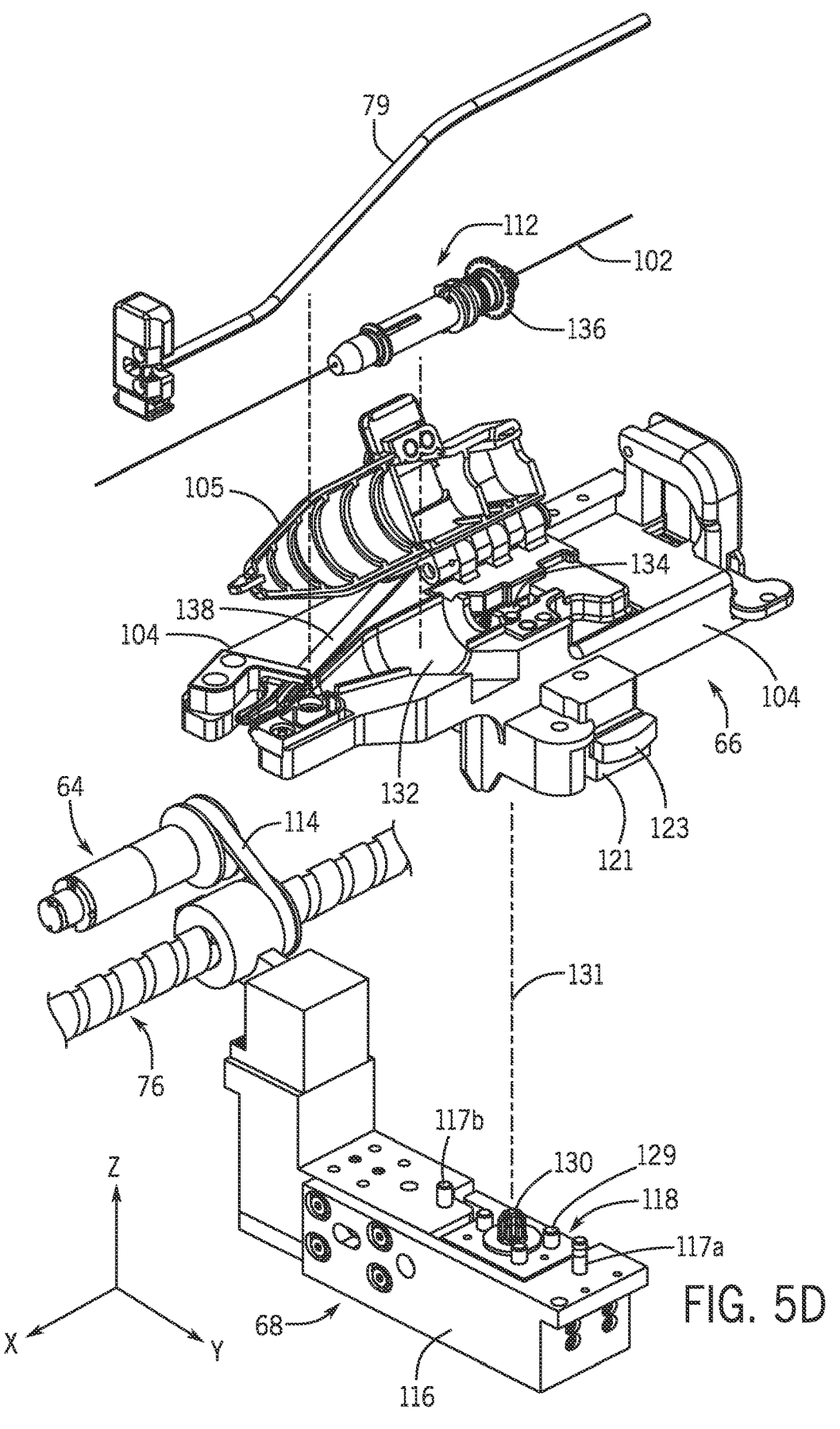
FIG. 5D is an exploded isometric view of a device module with a load sensing system and of a cassette that can receive an on-device adapter with an EMD in accordance with an embodiment.

Referring to FIG. 5D, a drive module 68 with a load sensing system is indicated with its connection to cassette 66 and EMD 102. Rotation of coupler 130 rotates EMD on-device adapter 112 to rotate and/or pinch/unpinch EMD 102, as described below.

Cassette 66 includes a cassette housing 104. Cassette housing 104 includes a cradle 132 configured to receive EMD on-device adapter 112 with EMD 102. A cassette bevel gear 134 in cassette housing 104 can freely rotate with respect to cassette housing 104 about an axis aligned with a coupler axis 131 about which coupler 130 of drive module 68 rotates. In the assembled device module 32, cassette 66 is positioned on mounting surface of drive module 68 such that cassette bevel gear 134 receives coupler 130 along coupler axis 131 in such a way that it is free to engage and disengage along coupler axis 131 and integrally connected (not free) about coupler axis 131 such that rotation of coupler 130 corresponds equally to rotation of cassette bevel gear 134. In other words, if coupler 130 rotates clockwise at a given speed, then cassette bevel gear 134 rotates clockwise at the same given speed, and if coupler 130 rotates counterclockwise at a given speed, then cassette bevel gear 134 rotates counterclockwise at the same given speed.

Cassette bevel gear 134 meshes with a driven bevel gear 136 that is integrally connected to EMD on-device adapter 112 when EMD on-device adapter 112 is seated in cradle 132 of cassette housing 104. In one embodiment, the embodiment of FIG. 5D, EMD 102 is a guidewire and EMD on-device adapter 112 is a collet. When power is transferred from coupler 130 of drive module 68 to cassette bevel gear 134, cassette bevel gear 134 meshes with driven bevel gear 136 on the collet to rotate the guidewire.

Referring to FIG. 5D, a device support 79 is positioned in a channel 138 in cassette housing 104. Device support 79 and cassette 66 are configured to move relative to one another. Details are provided in Patent Application 62/874, 247 entitled: SYSTEMS, APPARATUS AND METHODS FOR ROBOTIC INTERVENTIONAL PROCEDURES USING A PLURALITY OF ELONGATED MEDICAL DEVICES (U.S. Provisional Application 62/874,247, filed Jul. 15, 2019) incorporated herein by reference.

Referring to FIG. 5D, in one embodiment the drive module 68 moves the EMD 102 in a first direction, the isolated component 106 being separate from the cassette housing 104 in the first direction. In one embodiment the first direction is along the longitudinal axis of EMD 102. In this embodiment first direction corresponds to the X-axis. In one embodiment the drive module 68 moves the EMD 102 in a second direction, the isolated component 106 being separate from the cassette housing 104 in the first direction and the second direction. In one embodiment the second direction is rotation about the longitudinal axis of the EMD in the clockwise and counterclockwise direction.

Figure 5E:
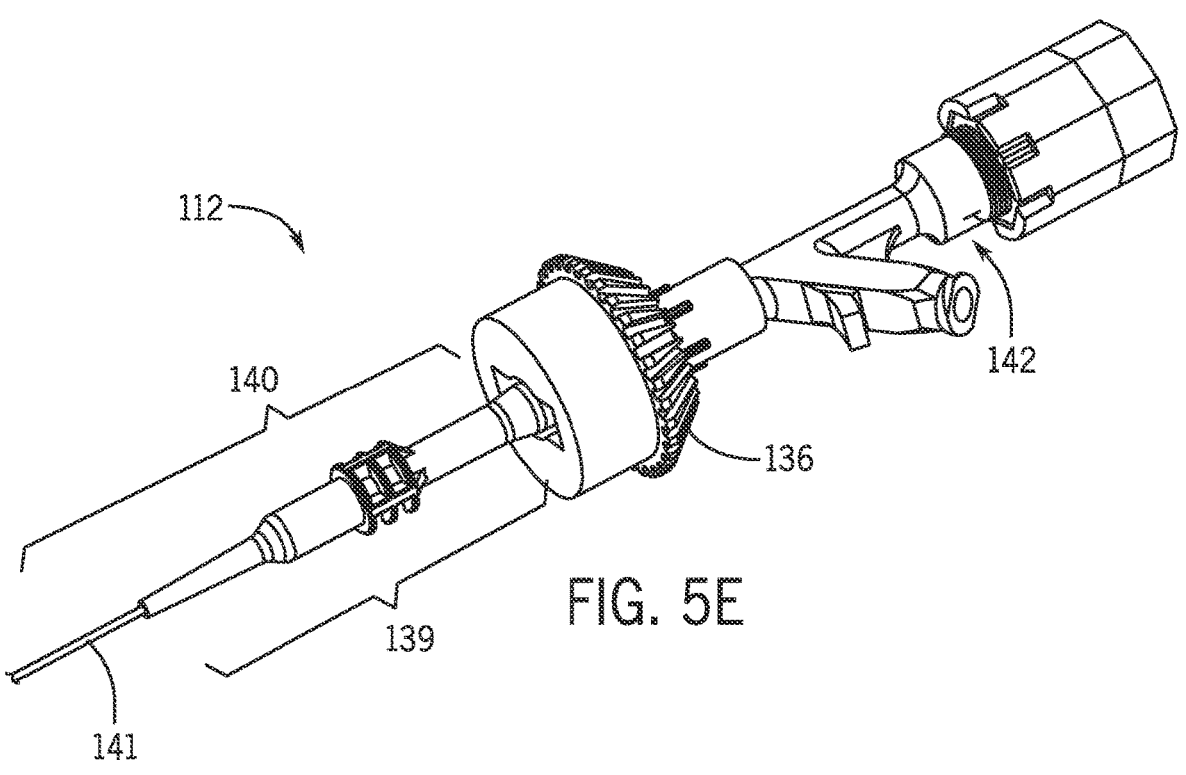
FIG. 5E is an isometric view of a catheter with an EMD on-device adapter in accordance with an embodiment.
Figure 5F:
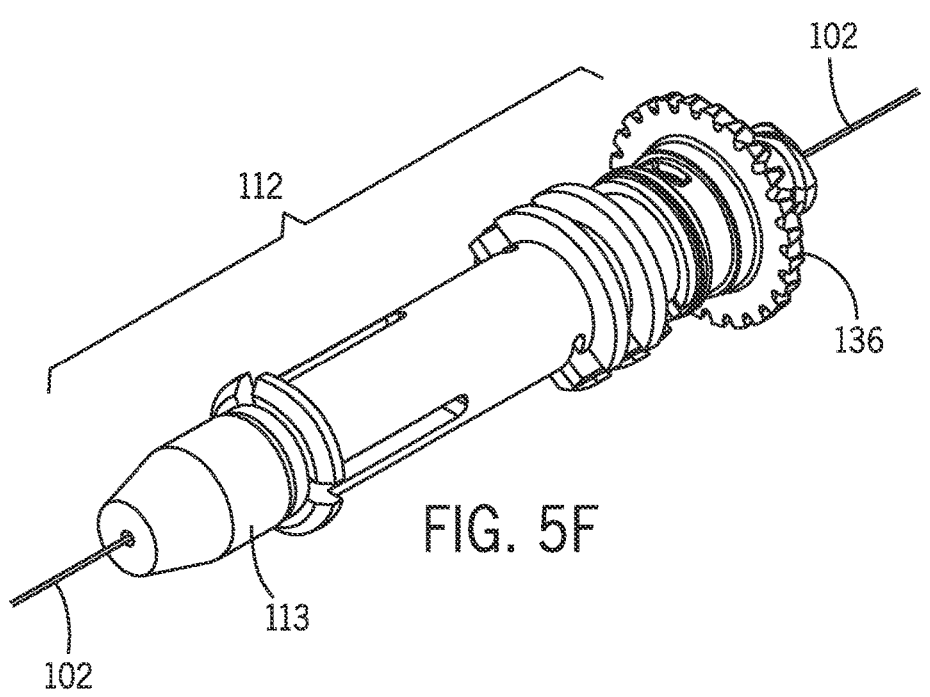
FIG. 5F is an isometric view of a guidewire with an EMD on-device adapter in accordance with an embodiment.
Figure 5G:
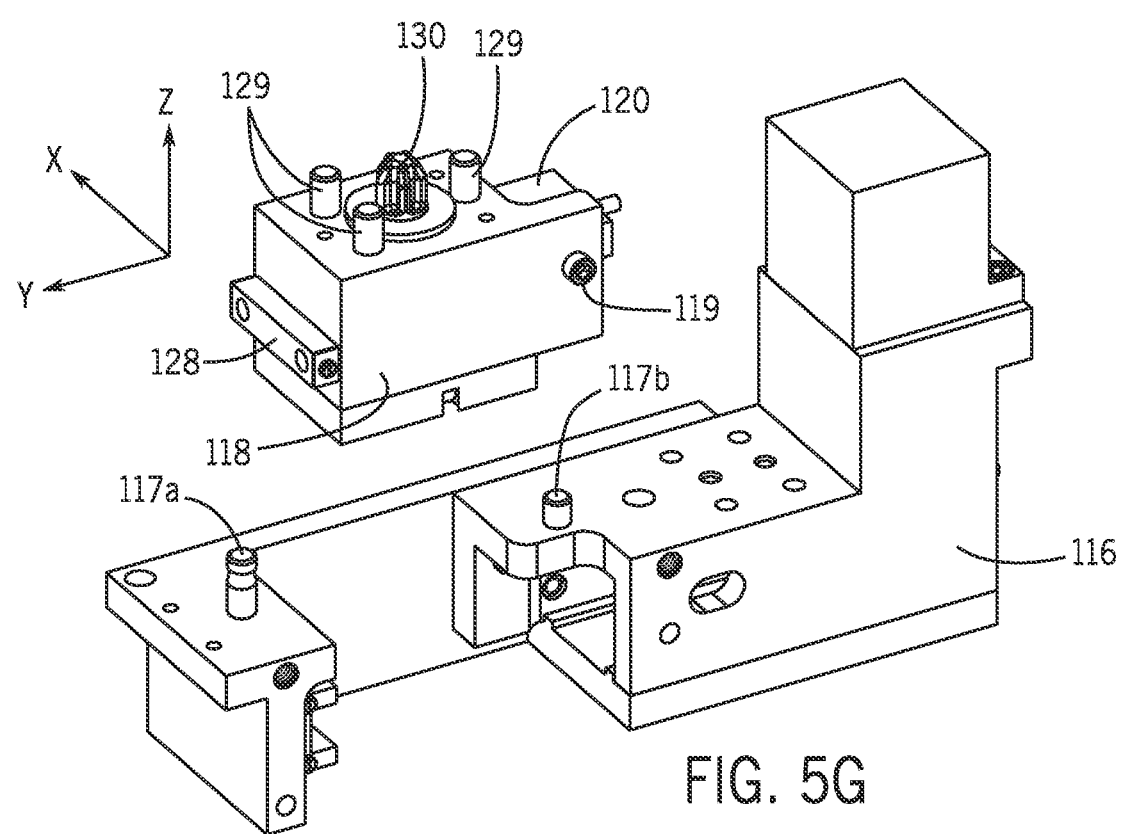
FIG. 5G is an exploded isometric view of a drive module with drive module base component and load-sensed component.
Figure 5H:
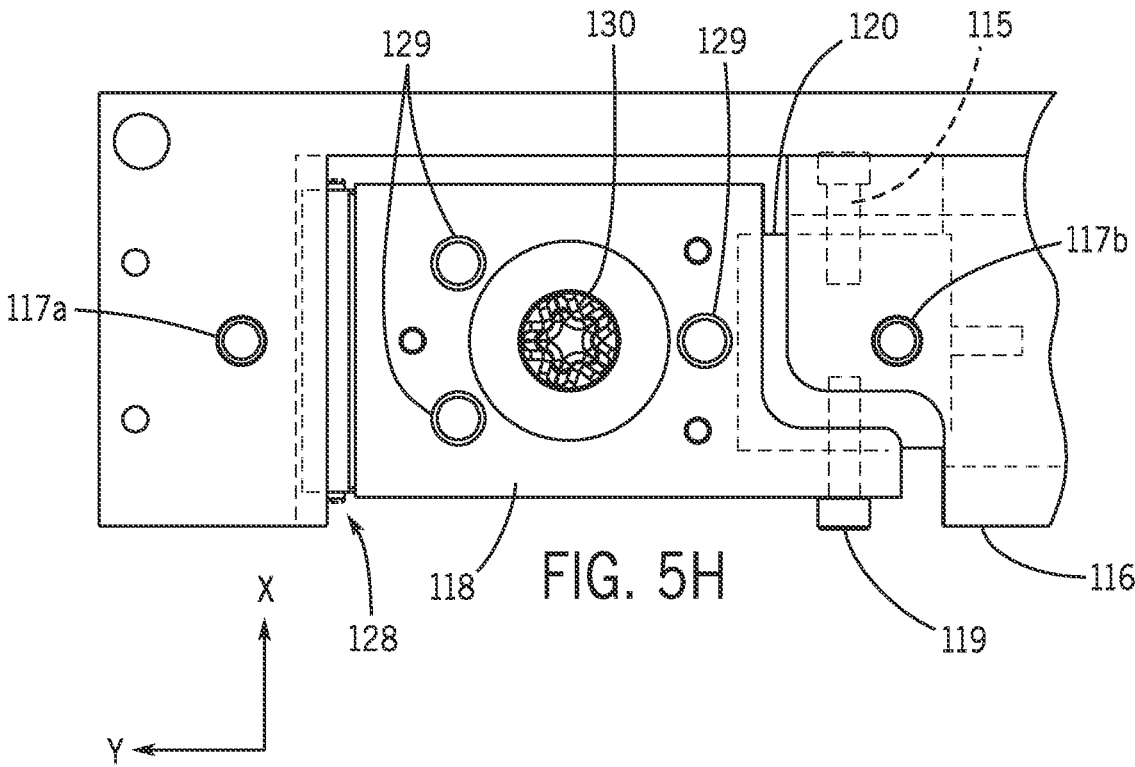
FIG. 5H is a close-up top view of FIG. 5A showing the load-sensed component connected to a load sensor within the drive module base component.
Figure 5I:
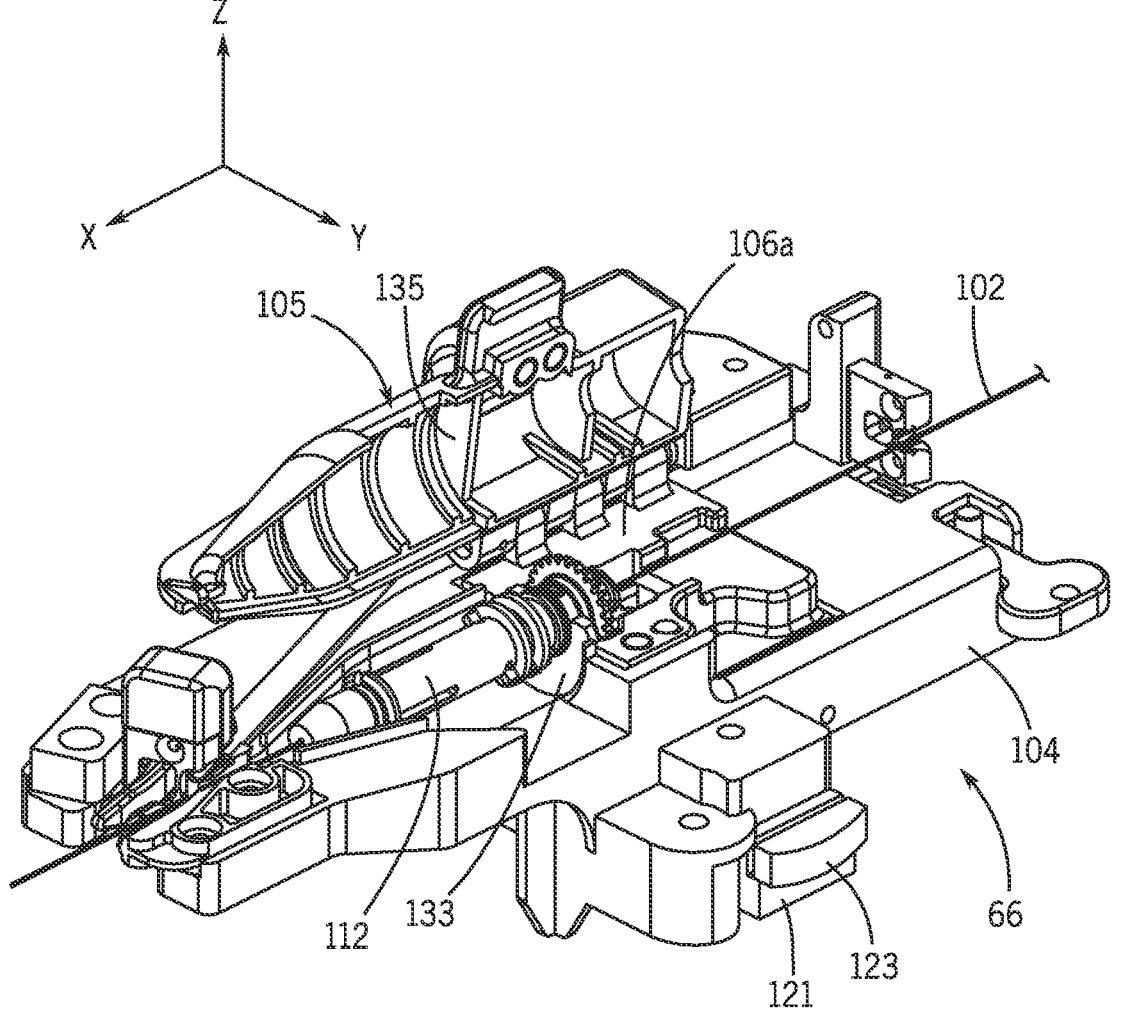
FIG. 5I is an isometric view of a cassette with an on-device adapter with an EMD in accordance with an embodiment.

Referring to FIGS. 5D and 5I in one embodiment the apparatus includes a cassette 66 that is comprised of a cassette housing 104 removably attached to the drive module base component 116 and a cassette cover 105 attached to the isolated component 106.

Referring to FIGS. 4A-4D, 5D, and 5I, in one embodiment the on-device adapter 112 is spaced from and in non-contact relationship with the cassette housing 104 when the on-device adapter 112 is coupled to the load-sensed component 118 through the isolated component 106. In one embodiment the isolated component 106 is separate from the cassette housing 104 in all directions. In one embodiment the isolated component 106 is separate from and in a non-contact relationship with the cassette housing 104.

Figure 5J:
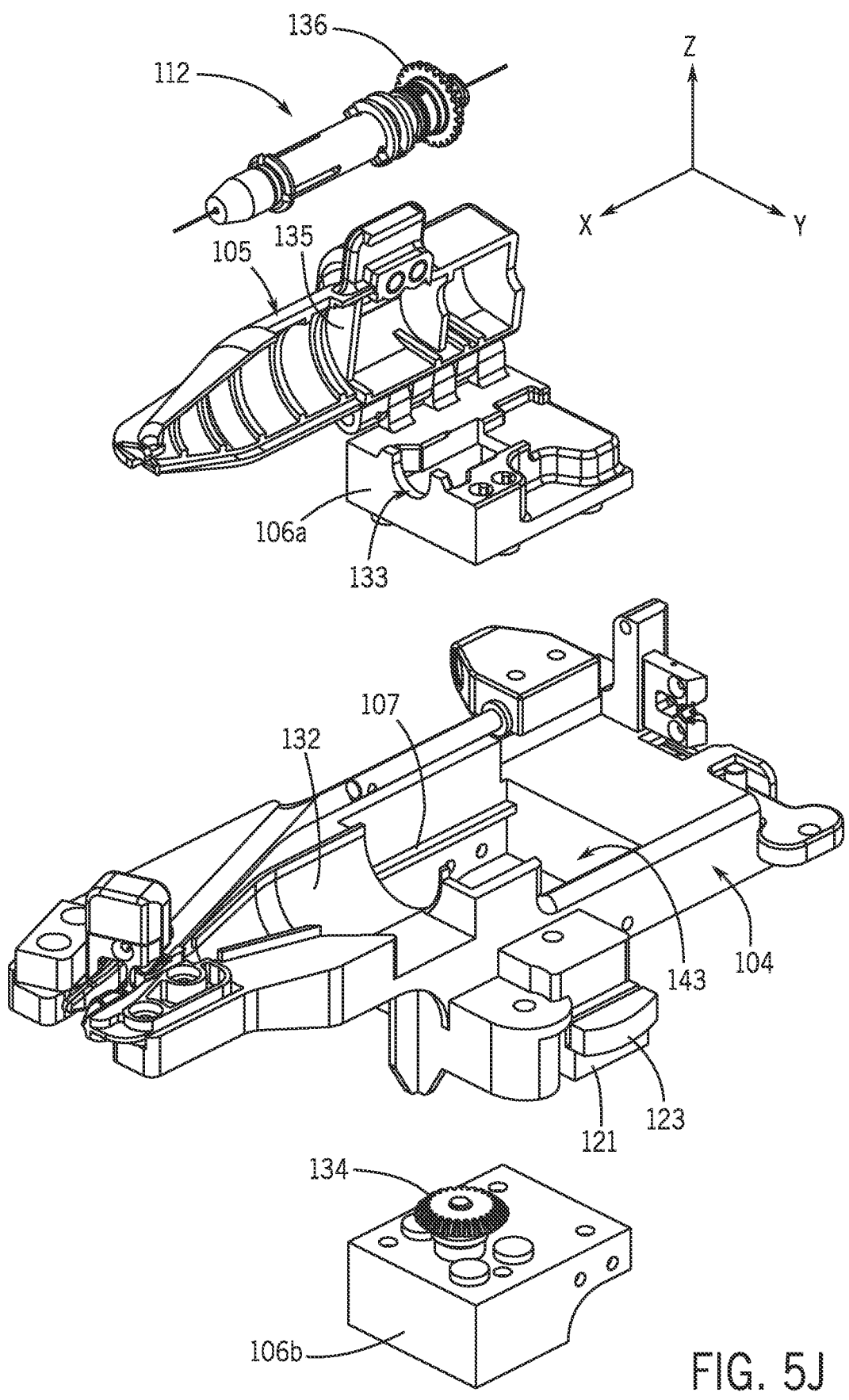
FIG. 5J is an exploded isometric view of a cassette showing first component and second component of an isolated component.

Referring to FIGS. 5D, 5I and 5J, isolated component 106 includes a first component 106a and a second component 106b attached thereto. The first component 106a is placed within a recess 143 of the cassette housing 104 in a direction toward the drive module 68 when the cassette 66 is in the in-use position secured to the drive module 68. The second component 106b is placed within the recess 143 from a direction away from the load-sensed component 118 toward the first component 106a. The isolated component 106 is positioned within and separate from the cassette housing 104 in at least one direction when the isolated component 106 is connected to the load-sensed component 118.

Referring to FIG. 5G, in one embodiment drive module base component 116 includes a recess that receives load-sensed component 118. In one embodiment drive module base component 116 further defines a cavity extending from recess that receives a portion of load sensor 120.

Referring to FIGS. 5I and 5J, cassette 66 includes a cassette housing 104 and a cassette cover 105 that is connected to the first component 106a of isolated component 106. Cassette housing 104 includes a cavity 132 configured to receive EMD on-device adapter 112 with EMD 102. Cavity 132 is also referred to herein as cradle 132.

Figure 5K:
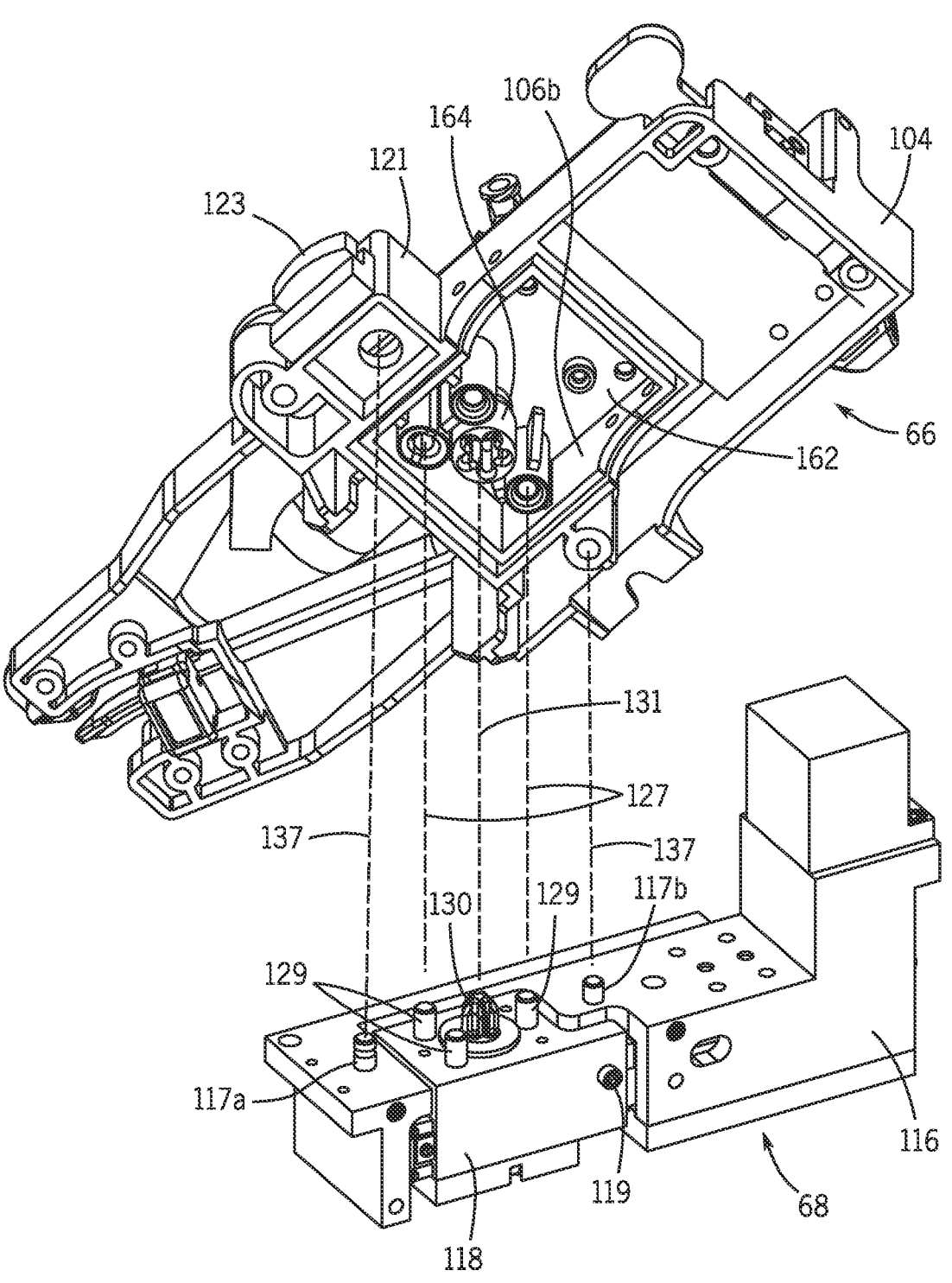
FIG. 5K is an exploded isometric view of the underside of a cassette and its connection to the drive module.
Figure 5L:
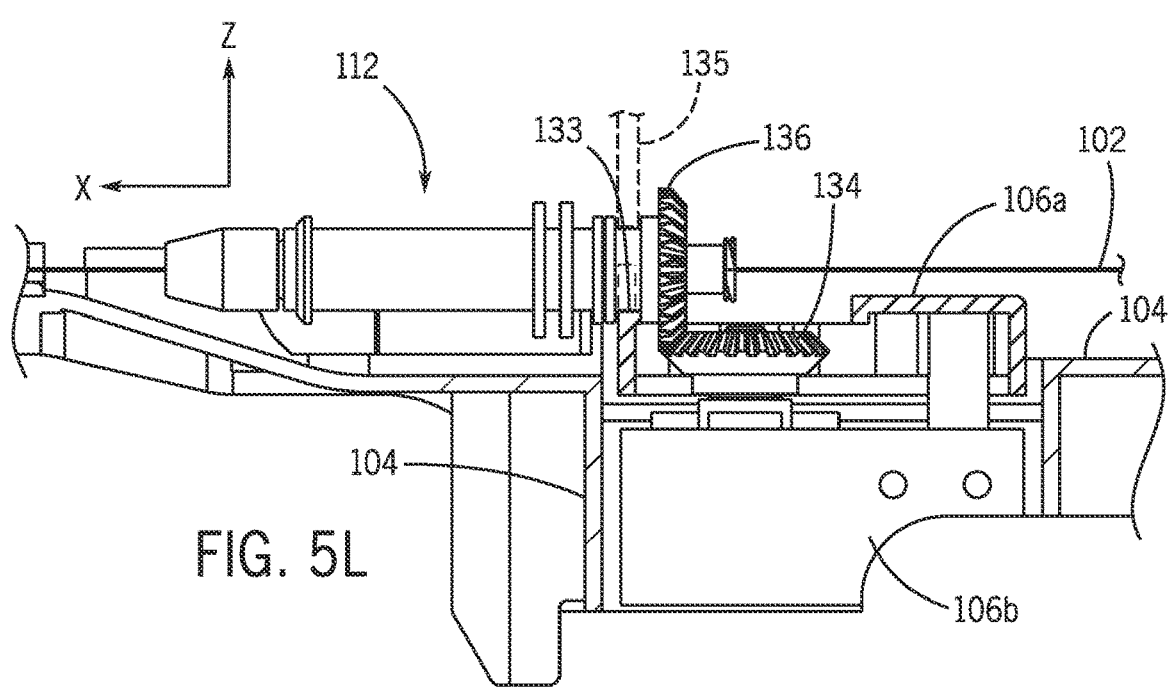
FIG. 5L is a partial side view of FIG. 5I showing an on-device adapter with an EMD supported in an isolated component as part of a cassette.

Referring to FIGS. 5J, 5K, and 5L, cassette bevel gear 134 in second component 106b of isolated component 106, where isolated component 106 is contained within cassette housing 104, can rotate freely with respect to the isolated component 106 about an axis aligned with a coupler axis 131 about which coupler 130 of load-sensed component 118 rotates, where load-sensed component 118 is contained within drive module 68.

Referring to FIGS. 5I and 5K, in one embodiment cassette housing 104 is releasably connected to drive module base component 116 via a quick-release mechanism 121. In one embodiment quick-release mechanism 121 includes a spring-biased member in the cassette housing 104 that is activated by a latch release 123 that releasably engages with a quick release locking pin 117a secured to the drive module base component 116. In one embodiment an alignment pin 117b secured to the drive module base component 116 aligns the cassette housing 104 relative to the drive module base component 116.

Referring to FIGS. 5I and 5L, in one embodiment in the in-use position the on-device adapter 112 is supported in a cylindrical groove located longitudinally toward the proximal end of the on-device adapter 112. In the in-use position the support of the on-device adapter 112 is provided by a bottom support 133 on the distal face of the first component 106a of isolated component 106 and a top support 135 on the interior of closed cassette cover 105. In one embodiment the groove in the on-device adapter 112 supporting the on-device adapter 112 is located on the on-device adapter 112 longitudinally toward the proximal end of the on-device adapter 112 and distal to driven bevel gear 136. In one embodiment the on-device adapter 112 includes features such as flanges on either side of the groove supporting the on-device adapter 112. In one embodiment the support provided by bottom support 133 and top support 135 at the groove of the on-device adapter 112 act as a thrust bearing for the on-device adapter 112 allowing the on-device adapter 112 to rotate freely and constraining longitudinal motion of the on-device adapter 112 to the translational motion of the first component 106a of the isolated component 106 and the cassette cover 105, which are connected at hinge 103. Bottom support 133 is also referred to as rotational drive element cradle.

Figure 5M:
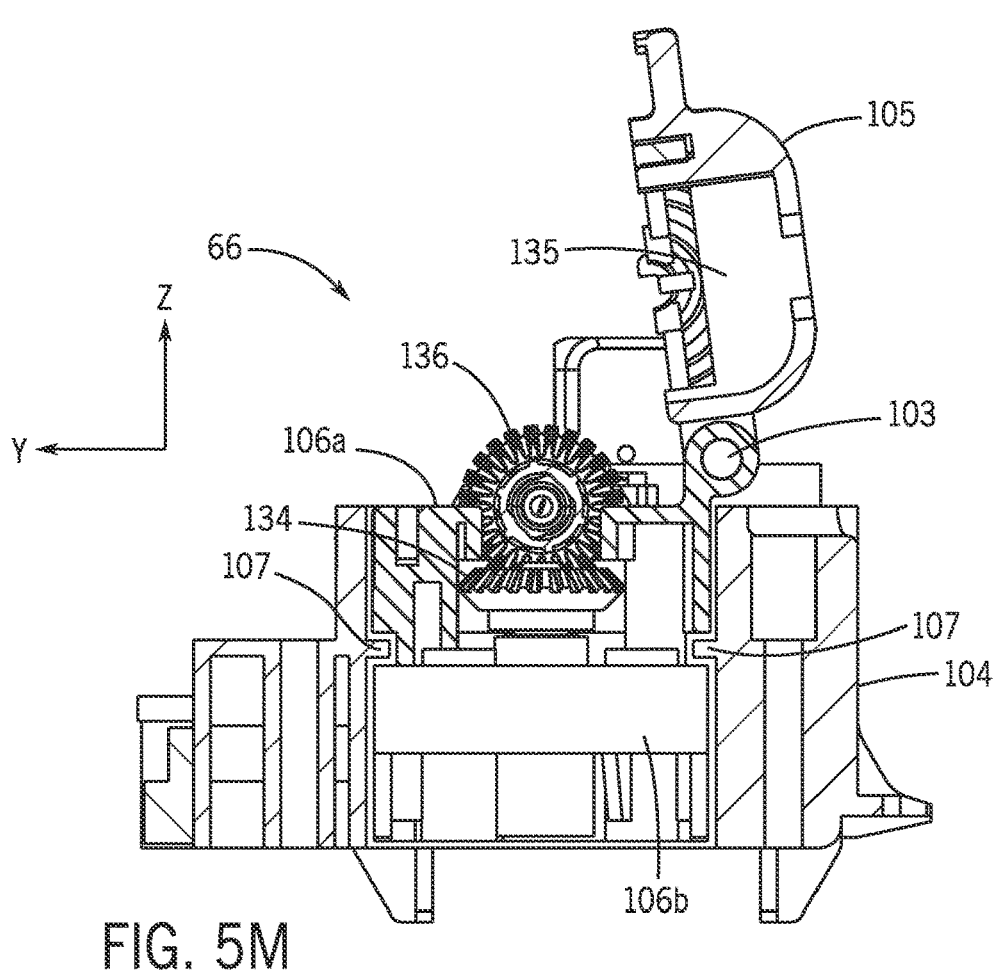
FIG. 5M is an end cross-sectional view of FIG. 5I showing meshing of bevel gears in a cassette.

Referring to FIGS. 5I, 5J, and 5M, in one embodiment the cassette 66 includes a cassette cover 105 pivotably coupled by hinge 103 to the isolated component 106 separate and in non-contact with the cassette housing 104. In one embodiment the cassette cover 105 is pivotably coupled by hinge 103 to the first component 106a of the isolated component 106. In one embodiment the cassette cover 105 is connected to the first component 106a of the isolated component 106 by other means, such as snap fits. In one embodiment the EMD 102 is spaced from and in non-contact with the cassette housing 104 when the on-device adapter 112 is coupled to the load-sensed component 118.

Referring to FIG. 5E, a catheter 140 embodiment of EMD 102 with EMD on-device adapter 112 and driven bevel gear 136 is indicated. Catheter 140 includes a hub that can be connected to, for example, a rotating hemostasis valve, on the proximal end of catheter 140. In one embodiment hub of catheter 140 is free of controls used to manipulate features within catheter 140 such as a wire extending to the distal end of the catheter to deflect the tip. In one embodiment catheter 140 does not include any controls used to manipulate features within the catheter 140 such as a wire extending to the distal end of the catheter 140 to deflect the tip.

In one embodiment EMD on-device adapter 112 includes a catheter 140 integrally connected to a driven bevel gear 136 that can be removably connected to a Y-connector shown with hub 142 that can be removably connected to a hemostasis valve on the proximal end. One embodiment of EMD on-device adapter 112 includes a catheter 140 removably connected to a driven bevel gear 136. Catheter 140 includes a catheter hub 139 and a catheter shaft 141 that are integrally connected.

Referring to FIG. 5F, a guidewire embodiment of EMD 102 with EMD on-device adapter 112 and driven bevel gear 136 is indicated. In the embodiment of FIG. 5F EMD on-device adapter 112 is a collet 113 with driven bevel gear 136 on the proximal end of the collet.

In one embodiment on-device adapter 112 includes a collet 113 with a collet jaw (or collet nut) at the distal end of on-device adapter 112 and a collet body captured within an open cylindrical housing to which a driven bevel gear 136 is integrally connected at the proximal end of the on-device adapter 112. A lumen through the central longitudinal axis of on-device adapter 112 is coaxial with the central longitudinal axis of the collet 113 allowing for a guidewire EMD 102 to pass through. In one embodiment the open cylindrical housing of on-device adapter 112 includes features, such as longitudinal slits, enabling the collet body to be press-fit within the cylindrical housing. In one embodiment the cylindrical housing of on-device adapter 112 includes external flanges that can be used to ensure kinematic engagement with actuated members for translation of on-device adapter 112. In one embodiment rotation of driven bevel gear 136 corresponds to rotation of on-device adapter 112 and hence is used to rotate and/or pinch/unpinch an EMD 102.

Referring to FIGS. 5J and 5M, isolated component 106 is contained inside cassette housing 104 by attaching first component 106a to second component 106b of isolated component 106 about rails 107 in cassette housing 104. In the in-use position, isolated component 106 is not in contact with rails 107.

In one embodiment the load sensor 120 measures a reaction force applied by the EMD 102 to the isolated component 106 of the cassette 66. In one embodiment, the load sensor 120 measures a torque applied by the EMD 102 to the isolated component 106 of the cassette 66. In one embodiment the load sensor 120 measures both a reaction force and reaction torque applied by the EMD to the isolated component 106 of the cassette 66. In one embodiment the actual force acting along a longitudinal axis of the EMD 102 and a torque about the longitudinal axis of the EMD 102 are determined based on the load sensor measurements.

Referring to FIGS. 5J and 5M, the first component 106a and second component 106b of isolated component 106 are secured to one another. Cassette housing 104 includes two longitudinally oriented rails 107 located within the recess 143. Rails 107 are also referred to as linear guides herein. Prior to the cassette 66 being attached to the drive module 68, the first component 106a is located on the top surface of rails 107 closest to the top surface of the cassette housing 104 and the second component 106b is located below and spaced from the bottom surface of rails 107 closest to the load-sensed component 118. Note that although the direction of assembly of first component 106a and second component 106b of the isolated component 106 is described in relation to the in-use position, the first and second components of the isolated component 106 are installed away from the drive module 68. Stated another way, the first component 106a of the isolated component 106 is inserted into the recess 143 in a direction from a top surface of the cassette 66 toward the bottom surface of the cassette 66 in a direction generally perpendicular to the longitudinal axis of the cassette housing 104.

In one embodiment a mechanical fastener or plurality of fasteners secure the first component 106a to the second component 106b of the isolated component 106. In one embodiment the first component 106a and second component 106b are secured together using magnets. In one embodiment the first component 106a and second component 106b of the isolate component 106 are secured with an adhesive. In one embodiment the first component 106a and second component 106b are releasably secured to one another without the use of tools. In one embodiment the first component 106a and second component 106b are non-releasably secured to one another.

Referring to FIG. 5K, in one embodiment second component 106b of the isolated component 106 is releasably secured to the load-sensed component 118 with fasteners. In one embodiment the fasteners include a quick release mechanism that can releasably secure the second component 106b of the isolated component 106 to the load-sensed component 118. In one embodiment the fasteners are magnets. In one embodiment second component 106b of the isolated component 106 is releasably secured to the load-sensed component 118 by a separable press fit. In one embodiment, second component 106b of the isolated component 106 is releasably secured to the load-sensed component 118 by a clearance fit. In one embodiment, second component 106b of the isolated component 106 is releasably secured to the load-sensed component 118 by an interference fit.

Referring to FIG. 5M, in an in-use position where the second component 106b of the isolated component 106 is releasably secured to the load-sensed component 118, the first component 106a and second component 106b are spaced from the rails 107 of the cassette housing 104 such that the first component 106a and second component 106b are in a non-contact relationship with cassette housing 104.

Figures 6A, 6B:
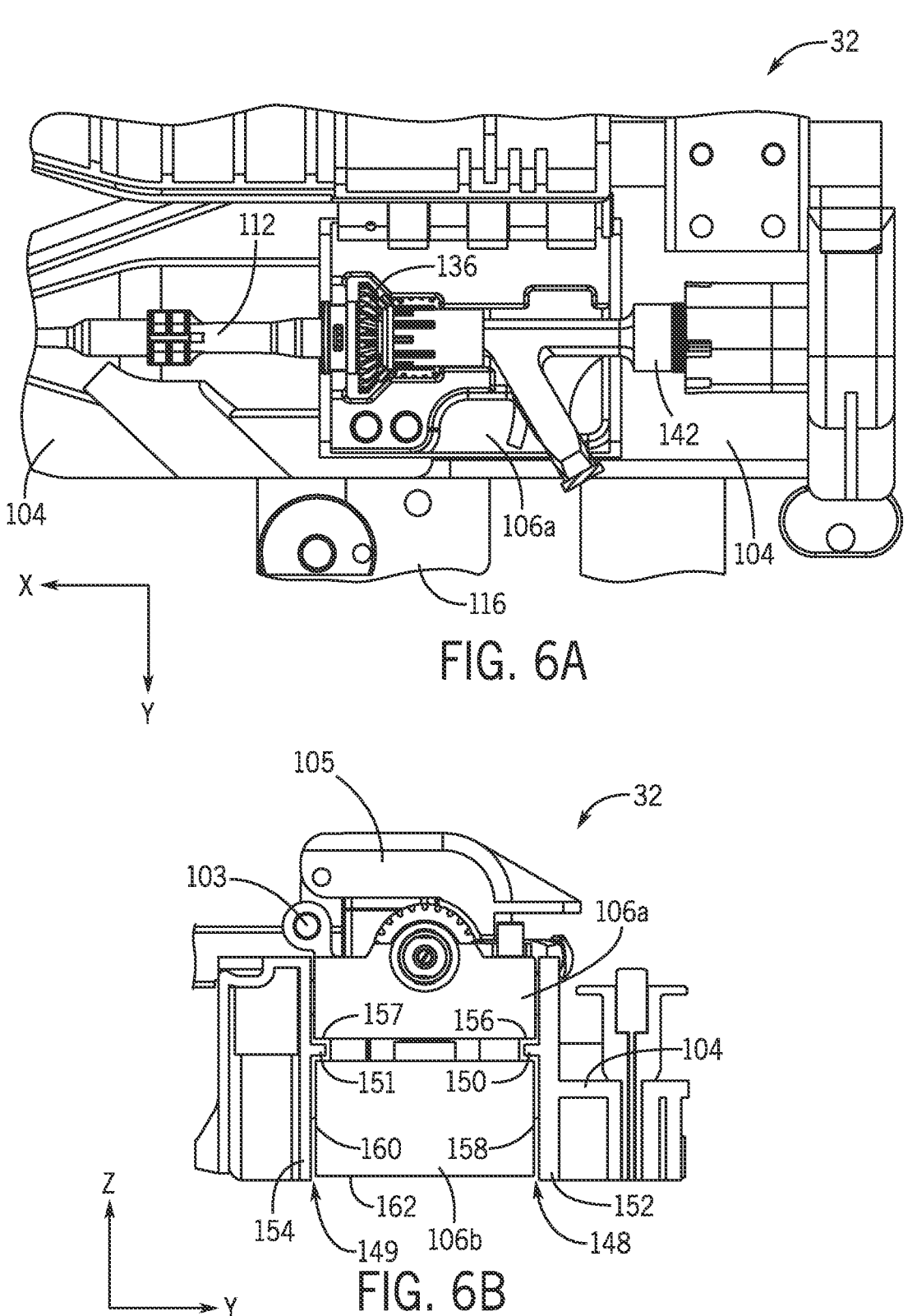
FIG. 6A is a top view of a cassette with an isolated component and a cassette housing in accordance with an embodiment.
FIG. 6B is an end cross-sectional view of an isolated component and a cassette in accordance with an embodiment.

Referring to FIG. 6A, a device module 32 with cassette housing 104 and first component 106a of isolated component 106 is indicated. Drive module base component 116 is also indicated. First component 106a of isolated component 106 is located in cassette housing 104 and provides support for EMD 102 (not shown) captured in EMD on-device adapter 112. In one embodiment, cassette housing 104 is a rigid (relatively stiff) support. EMD on-device adapter 112 includes a driven bevel gear 136 in isolated component 106 configured to interface with a cassette bevel gear 134 (not shown). The on-device adapter 112 with driven bevel gear 136 is supported in a rotational drive element cradle 133 of first component 106a of isolated component 106. In one embodiment EMD on-device adapter 112 with Y-connector includes a Y-connector hub 142. In one embodiment isolated component 106 is floating with respect to cassette housing 104 in the sense that there is no direct contact.

Cassette housing 104 reacts forces such as, for example, forces from a device support 79 connected to the cassette, drag force of fluid tubes, forces applied by support track arms, and loads from other components connecting or interacting with cassette other than EMD 102 To reduce measurement noise for rotational forces, rotational drive element cradle 133 supporting driven bevel gear 136 of an EMD on-device adapter 112 may be formed from low friction static material. In another embodiment, rotational drive element cradle 133 may include bearings in the form of sliding or rolling bearings.

Referring to FIG. 6B, isolated component 106 includes a first component 106a and a second component 106b that are connected and the isolated component 106 is separated from cassette housing 104 by a first slot 148 and a second slot 149. The isolated component 106 is loosely contained within first slot 148 and second slot 149 and confined to a limited range of motion. The range of motion of isolated component 106 allows isolated component 106 to be mounted a load-sensed component 118 of a drive module 68 (not shown) while allowing for tolerances between interfacing components. First slot 148 and second slot 149 are configured to allow limited movement of isolated component 106 in the X and Y directions. Isolated component 106 is also floating but captive in first slot 148 and second slot 149 in the Z direction due a first tab 150 on a first side 152 of cassette housing 104 and a second tab 151 on a second side 154 of cassette housing 104. Isolated component 106 includes a first recess 156 on a first side 158 of isolated component 106 and a second recess 157 on a second side 160 of isolated component 106. First tab 150 is loosely positioned in first recess 156 of isolated component 106, and second tab 151 is loosely positioned in second recess 157 of isolated component 106. In one embodiment isolated component 106 and cassette housing 104 exist as separate components. In one embodiment isolated component 106 and cassette housing 104 exist as a single unit, rather than two completely independent pieces. In one embodiment a contactless frictionless interface is achieved when the isolated component 106 is mounted to a drive module 68 (not shown). In one embodiment isolated component 106 is mounted to drive module 68 by contact.

In one embodiment positioning pins 129 on drive module load-sensed component 118 engage with connection points 166 on floating component 106. Cassette housing 104 is attached to drive module base component 116 when cassette 66 is mounted to drive module 68. The positioning pins on drive module 68 lift floating component 106 to a height relative to the cassette housing 104 where a contactless interface is achieved. In one embodiment the height is 1 mm. In other embodiments the height is less than 1 mm and in other embodiments the heights is greater than 1 mm. The contactless frictionless interface between floating component 106 and cassette housing 104 allows that the actual load acting on the EMD 102 in the measurement direction (X-axis) is solely supported by the load-sensed component 118, and therefore, prevents frictional parasitic loads from being combined into sensed loads by load sensor 120. In other words, floating component 106 of cassette 66 capturing EMD 102 is directly load-sensed and is isolated from sources of parasitic loads.

Figure 6C:
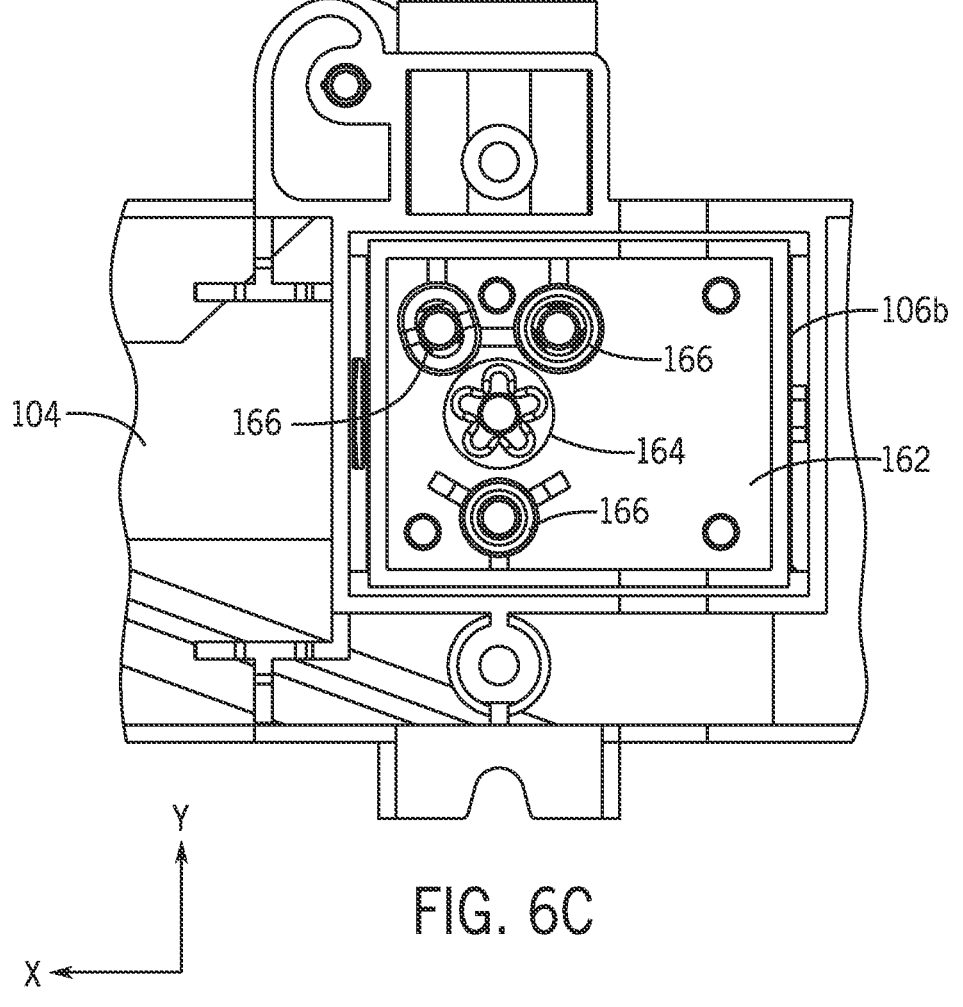
FIG. 6C is a bottom view of an isolated component and a cassette housing in accordance with an embodiment.

Referring to FIG. 6C, a bottom view of floating component 106 of cassette 66 is indicated. Bottom surface 162 of floating component 106 is configured to couple to drive module 68. Bottom surface 162 of floating component 106 includes a connector 164 to receive coupler 130 of drive module 68. Bottom surface 162 of floating component 106 also includes connection points 166 configured to receive connection members of drive module 68. For example, positioning pins 129 in drive module 68 may fit into a series of holes and slots in bottom surface 162 of floating component 106. Positioning pins 129 may be used to fully constrain floating component 106 and drive module 68 in the X, Y and Z directions. In one embodiment floating component 106 is constrained in the Z direction by magnets positioned in one or more connection points 166. In another embodiment floating component 106 is constrained in the Z direction by friction with connection points 166. In one embodiment slots are used to interact with positioning pins 129 of drive module 68 to constrain floating component 106.

Referring to FIGS. 5K and 6C, in one embodiment positioning pins 129 on load-sensed component 118 of drive module 68 seat within pockets in connection points 166 on second component 106b of isolated component 106. Cassette housing 104 is attached to drive module base component 116 when cassette 66 is mounted to drive module 68. The positioning pins 129 of load-sensed component 118 within drive module 68 lift second component 106b of isolated component 106 to a height relative to the cassette housing 104 where a contactless interface is achieved between the isolated component 106 and cassette housing 104. In one embodiment the isolated component 106 does not contact the cassette housing 104 in the three orthogonal X, Y, and Z directions. In one embodiment the clearance height between isolated component 106 and cassette housing 104 is 1 mm. In other embodiments the clearance height is less than 1 mm and in other embodiments the clearance height is greater than 1 mm. The contactless frictionless interface between isolated component 106 and cassette housing 104 allows that the actual load acting on the EMD 102 in the measurement direction (X-axis) is solely supported by the load-sensed component 118, and therefore, prevents frictional parasitic loads from being combined into sensed loads by load sensor 120. In other words, isolated component 106 of cassette 66 capturing EMD 102 is directly load-sensed and is isolated from sources of parasitic loads.

Figure 7:
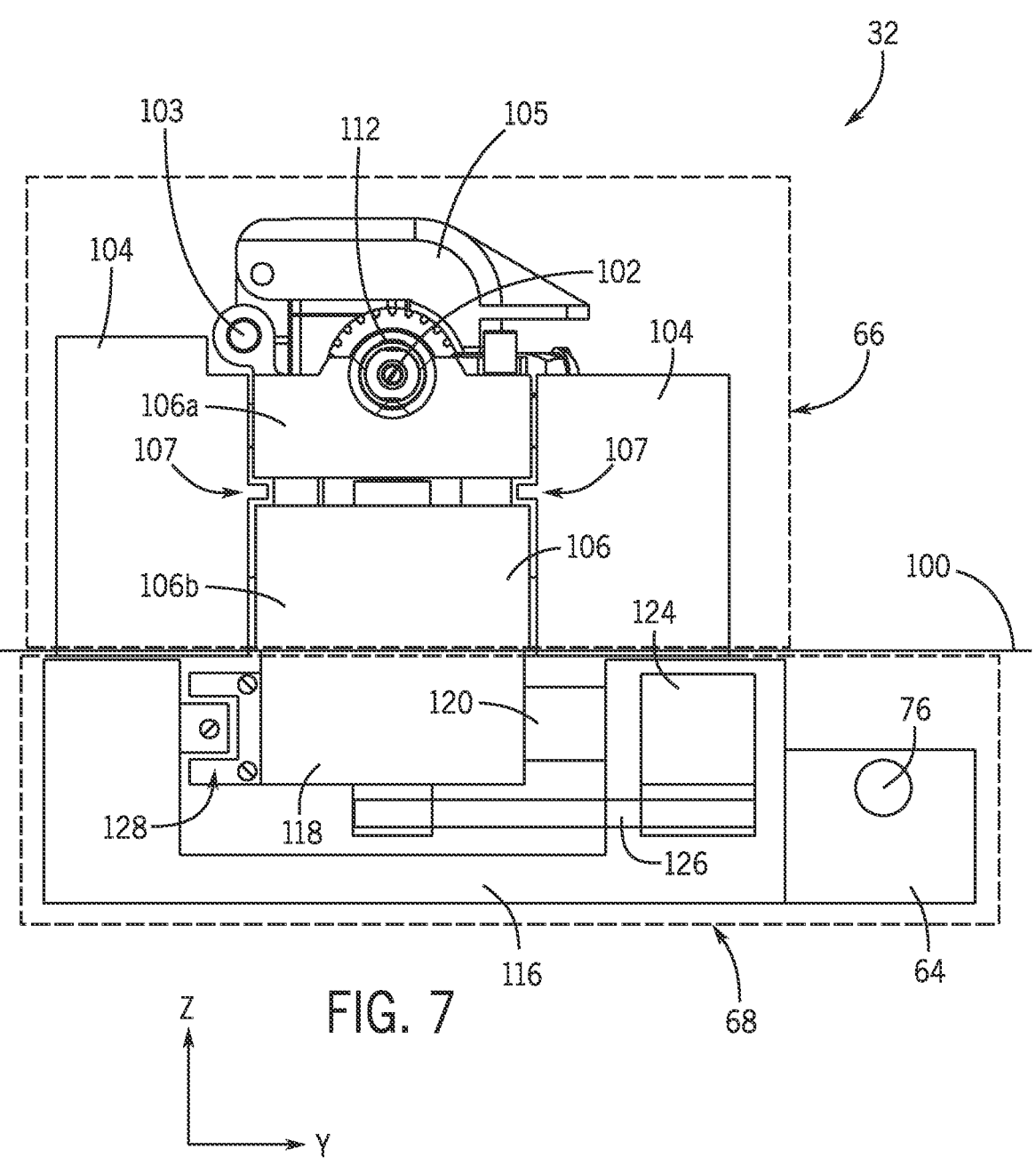
FIG. 7 is a schematic end cross-sectional view of an example embodiment of a load sensing system of FIG. 4D indicating disposable cassette components and capital drive module components.

Referring to FIG. 7, a side view of an example embodiment of a load sensing system, such as that of FIG. 4D, including disposable cassette components and capital drive module components is indicated. Device module 32 includes a cassette 66 and a drive module 68, indicated by dashed lines. In one embodiment, cassette 66 and its components are disposable and drive module 68 and its components are capital, that is, reusable and not disposable. Cassette 66 includes cassette housing 104 and an isolated component 106 connected to cassette cover 105.

In one embodiment the linear DOF motion of EMD 102 is achieved by moving device module 32 along a stage drive mechanism 76 while EMD 102 is captured by an EMD on-device adapter 112 integrally connected to floating component 106 of cassette 66. EMD on-device adapter 112 is also known as an end-effector or an on-device adapter. In one embodiment EMD on-device adapter 112 is a collet. In one embodiment EMD on-device adapter 112 is a hub drive. In one embodiment stage drive mechanism 76 is a lead screw and drive module 68 includes a stage translation motor 64 that rotates a nut on the lead screw.

Drive module 68 includes load-sensed component 118 and load sensor 120. In one embodiment load sensor 120 is a single-axis sensor measuring the reaction force to determine the actual force on EMD 102 captured by EMD on-device adapter 112. In one embodiment load sensor 120 is a multi-axis sensor measuring components of the reaction load to determine the corresponding actual force and torque acting on EMD 102 captured by EMD on-device adapter 112. In one embodiment at least one actuator 124 used to rotate EMD 102 and/or to pinch/unpinch EMD 102 is located outside load-sensed component 118. As indicated earlier, this reduces parasitic loads (such as inertial loads) that may be imparted by the actuator on load-sensed component 118.

In one embodiment power is transferred from actuator 124 located outside of load-sensed component 118 to the drive components inside load-sensed component 118 by using a belt 126 perpendicular to the load-measurement direction. In one embodiment power is transferred from actuator 124 located outside of load-sensed component 118 to the drive components inside load-sensed component 118 by other means, such as using a chain or cables or wires perpendicular to the load-measurement direction. In one embodiment power is transferred from actuator 124 to the EMD on-device adapter 112 through a drive train that imparts a load in the load measurement direction on load sensor 120, where this load can be corrected for in determination of actual load on EMD 102. In one embodiment actuator 124 includes an encoder for device angular position feedback.

In one embodiment power is transferred from actuator 124 located outside of load-sensed component 118 to the drive components inside load-sensed component (for example, pulleys and/or capstans used to drive the disposable on-device adapters in the cassette) through a power train that does not impart a load in the load measurement direction on load sensor 120.

In one embodiment load sensor 120 is a force sensor such as a bending beam force sensor to measure the force acting on EMD 102. In one embodiment load sensor 120 is a multi-axis sensor used to measure the force and the torque acting on EMD 102. In one embodiment, the center line of the power train (e.g., belt, cable, chain, etc.) used to transmit power from actuator 124 for rotation or pinching/unpinching of EMD 102 to load-sensed component 118 coincides with the axis of load sensor 120 so that no torque is applied by pretension in the power train to the torque sensor in the torque measurement direction. In another embodiment, the power train is parallel to the EMD proximal portion engaged in floating component 106 so that no torque is created by pretension in the power train in a torque measurement direction.

In one embodiment a load sensor 120 is used in the powertrain between actuator 124 for rotation or pinching/unpinching of EMD 102 and EMD on-device adapter 112 to determine the torque acting on EMD 102 and/or the torque applied to pinch/unpinch a collet. In one embodiment, load sensor 120 is located between actuator 124 and drive module base component 116 to determine the torque acting on EMD 102 and/or the torque applied to pinch/unpinch a collet.

In one embodiment a bearing 128 is used to support load-sensed component 118 in at least one of non-measurement direction. In other words, bearing support 128 does not impart a load in the measurement direction. In one embodiment bearing support 128 is a linear bearing (directed into the plane) that supports load-sensed component 118 in all directions other than the force measurement direction.

Referring to FIG. 7 in one embodiment an actuator that rotates the EMD 102 about its longitudinal axis is located outside of the load-sensed component 118. In one embodiment an actuator that pinches/unpinches the EMD 102 within the drive module is located outside of the load-sensed component 118. In one embodiment the drive module 68 includes a power transmission device driven by the actuators for rotation and/or pinching/unpinching of the EMD 102, where said actuators are located outside the load-sensed component 118 which is used to actuate the parts inside the load-sensed component 118 in order to manipulate the EMD 102. In one embodiment the power transmission device does not impart a load on the load-sensed component 118 at least in one load measurement direction. In one embodiment the power transmission device is a flexible device that does not withstand a shear force such as belt, cable, chain. In one embodiment the power transmission device is perpendicular to the load measurement direction so that it does not impart a load on the load-sensed component 118 in the load measurement direction. In one embodiment the drive module 68 includes a bearing supporting the load-sensed component 118 at least in one non-measurement direction to support off-axis loads in that direction. In one embodiment the load sensor 120 is spaced from the longitudinal axis of the EMD 102. Additionally, in one embodiment the load-sensed component 118 is spaced from and not colinear with the EMD. In other words, the load sensor is spaced from a longitudinal axis of the EMD.

Referring to FIG. 8, a top view of a load sensing system that incorporates a double bevel gear drive mechanism 178 is indicated. Double bevel gear drive mechanism 178 is also referred to as double gear collet drive. The system includes a stage translation motor 64, a stage drive mechanism 76, an EMD 102, a drive module base component 116, a load-sensed component 118, a load sensor 120, a bearing 128 to support the load-sensed component 118, a first actuator 168 to rotate EMD 102 and/or pinch/unpinch EMD 102, a second actuator 170 to rotate EMD 102 and/or pinch/unpinch EMD 102, a first belt 172 used to rotate EMD 102 and/or pinch/unpinch EMD 102, and a second belt 174 used to rotate EMD 102 and/or pinch/unpinch EMD 102. In one embodiment load sensor 120 is secured to drive module base component 116 and to the load-sensed component 118. In one embodiment all sensors described herein are secured to the respective relevant adjacent components as disclosed in the figures as is known in the art.

In the embodiment shown, the load-sensed component 118 is a double bevel gear drive mechanism 178 driven by two actuators (168 and 170) through belts (172 and 174) to accomplish rotation and/or pinching/unpinching of EMD 102 via a double portion collet 180. Mechanism 178 and collet 180 are described in detail in pending application US Application entitled MANIPULATION OF AN ELONGATED MEDICAL DEVICE (U.S. Provisional Application No. 62/874,173, filed Jul. 15, 2019). The '173 application describes a double-bevel collet drive mechanism.

In one embodiment an accelerometer 176 determines the acceleration of load-sensed component 118. In one embodiment accelerometer 176 is a single-axis accelerometer measuring the acceleration component in the longitudinal direction (that is, in the X direction). In one embodiment accelerometer 176 is a multi-axis accelerometer measuring acceleration components in the X, Y, and Z directions.

In one embodiment another type of sensor (e.g., a velocity transducer, a displacement transducer, etc.) is used to determine the acceleration of load-sensed component 118. In one embodiment more than one sensor is used to determine acceleration of different parts including the entire load-sensed component and an internal part of the load-sensed component with motion relative to the load-sensed component. In one embodiment the acceleration of the load-sensed component is determined from the actuator's parameters, for example, actuator's parameters of stage translation motor 64. Actuator's parameters include but are not limited to the actuator's encoder signal, electrical current of the actuator, and electrical voltage of the actuator.

Referring to FIG. 8, in one embodiment acceleration of the load-sensed component 118 is determined using a sensor such as an accelerometer 176 to correct for parasitic inertia loads. In one embodiment acceleration of the load-sensed component 118 is determined using a sensor such as a velocity transducer, from which the acceleration of the load-sensed component is determined to correct for parasitic inertia loads. In one embodiment acceleration of the load-sensed component 118 is determined using a sensor such as a displacement transducer, from which the acceleration of the load-sensed component is determined to correct for parasitic inertia loads.

The measured or determined acceleration may be used to correct the load measurements for parasitic loads caused by inertia of the load-sensed component and its internal parts, and to determine the actual loads acting on the EMD. Inertia force, $F_{inertia}$, may be calculated for each component as the product of mass and acceleration of the component in a given direction. The actual force can be determined from the sensed force ($F_{sensed}$) using equation (1).

Gravity loads on the load-sensed component may be determined based on the mass and orientation of the component as the product of mass and the component of gravity in a given direction.

Friction and drag parasitic loads may be measured and characterized to determine their values. In one embodiment, the measurement and characterization may be accomplished by conducting offline tests. In one embodiment, the values of friction and drag parasitic loads may be tabulated and/or formulated as a function of different parameters such as displacement and velocity.

In one embodiment at least one or more of the actuators are moved from the load-sensed component 118 to the drive module base component 116 in order to reduce parasitic inertia loads. In such a case, actuation power may be transferred from the actuator to the on-device adapters through a drive train that does not impart a load in the load measurement direction on the sensor (e.g., by using belts/chains/cables perpendicular to load-measurement direction, or by magnetic coupling). If the drive train imparts a parasitic load in the load measurement direction on the sensor, the load measurements need to be further corrected for the parasitic load in order to determine the actual load on the EMD.

In the system described herein, EMD 102 is manipulated by a mechanism within the floating component of the cassette. The floating component of the cassette is attached to the load-sensed component of the capital equipment, and the reaction loads applied by the EMD to the floating component of the cassette are measured using a sensor inside the capital equipment. A sterile barrier may be used between the capital unit (drive module) and the cassette so that no sterilization is required for the sensor or the drive module. Any component that can create parasitic loads (e.g. anti-buckling supports, tubing, cables, etc.) is connected to the base sub-component (cassette housing) of the disposable to isolate the load-sensed component from parasitic loads.

In one embodiment at least two loads are measured, such as force along a longitudinal axis of the EMD and torque about the longitudinal axis of the EMD.

In the embodiment shown in FIG. 8 the driving mechanism is a differential collet (containing two portions). In one embodiment the driving mechanism is a hub-drive module with 2 DOFs such as linear and rotation.

Figure 9A:
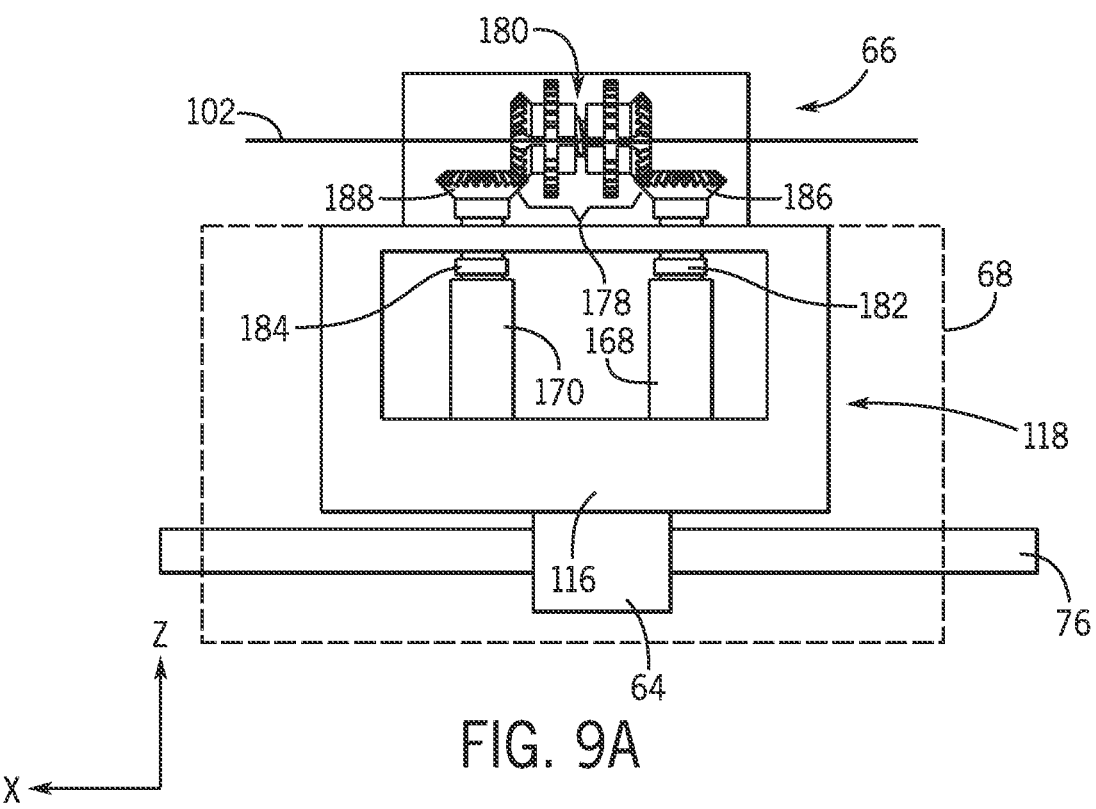
FIG. 9A is a schematic side view of an example embodiment of a load sensing system of FIG. 8 for a collet mechanism actuated by a double bevel drive with torque sensors at actuator capstans.
Figure 9B:
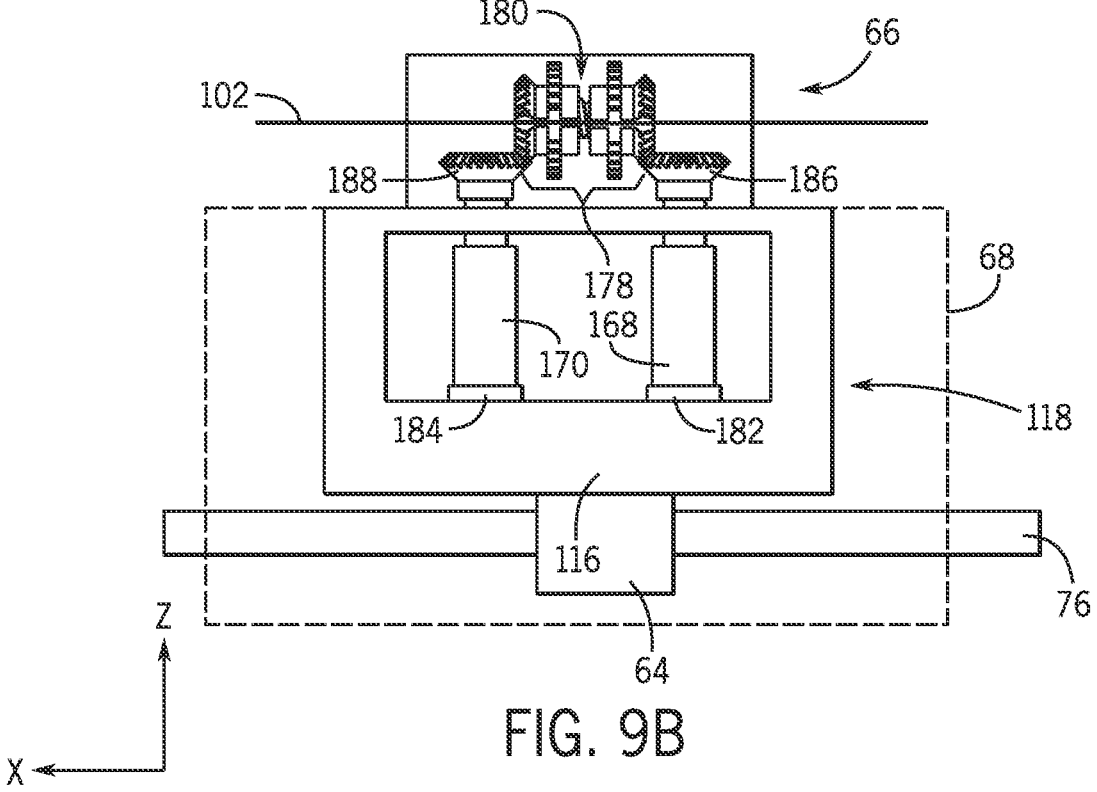
FIG. 9B is a schematic side view of another embodiment of a load sensing system of FIG. 9A.

Referring to FIG. 9A and FIG. 9B, a cassette 66 includes a collet 180 that is actuated by a double bevel gear drive mechanism 178 and through which EMD 102 is removably captured. Cassette 66 includes load-sensed component 118. The system also incorporates a drive module 68 that includes a stage translation motor 64, a stage drive mechanism 76, a drive module base component 116, a load sensor (not shown), a bearing (not shown) to support the load-sensed component 118, a first actuator 168, and a second actuator 170. The housings of actuators 168 and 170 are integrally mounted to drive module base component 116. The capstans (shafts) of actuators 168 and 170 are used to rotate EMD 102 and/or pinch/unpinch EMD 102. A first torque sensor 182 is located on the capstan of first actuator 168 that drives a first driver gear 186. First torque sensor 182 measures the reaction torque between first actuator 168 and first driver gear 186. A second torque sensor 184 is located on the capstan of second actuator 170 that drives a second driver gear 188. Second torque sensor 184 measures the reaction torque between second actuator 170 and second driver gear 188.

EMD 102 is removably located within a pathway defined by collet 180. Collet 180 has a first portion connected to a first collet coupler and a second portion connected to a second collet coupler. In one embodiment the capstan of first actuator 168 is operatively coupled to the first collet coupler through a pair of bevel gears and the capstan of second actuator 170 is operatively coupled to the second collet coupler through a pair of bevel gears. Rotation of first collet coupler and rotation of second collet coupler can be used independently and/or in combination to operatively pinch and unpinch EMD 102 in the pathway and/or to rotate EMD 102 clockwise and counterclockwise.

The double bevel gear drive mechanism 178 with collet 180 is described in pending U.S. Application entitled MANIPULATION OF AN ELONGATED MEDICAL DEVICE (U.S. Provisional Application No. 62/874,173, filed Jul. 15, 2019) incorporated herein by reference. (In particular, see the description related to figures F4.1-F4.6 of the application.)

First torque sensor 182 determines the torque acting on the first collet coupler and second torque sensor 184 determines the torque acting on the second collet coupler. A processor determines the torque acting on the EMD as a function of a first signal from first torque sensor 182 and a second signal from second torque sensor 184. Also, a processor determines the differential torque applied to the two ends of double bevel gear drive mechanism 178 to pinch the EMD 102 as a function of a first signal from first torque sensor 182 and a second signal from second torque sensor 184. In one embodiment the pinch force applied to the EMD is calculated by using the differential torque used to fasten double bevel gear drive mechanism 178 and pinch the EMD 102. In one embodiment the relationship between the pinch force on EMD 102 and differential torque applied to the two ends of double bevel gear drive mechanism 178 is determined by experimental tests. In one embodiment such relationship is determined by a mathematical model or equation.

Drive module 68 includes a first actuator 168 operatively coupled to the first collet coupler to operatively pinch and unpinch the EMD 102 in the pathway and to rotate the EMD 102 and a second actuator 170 operatively engaging the second collet coupler. A first torque sensor 182 (or more generally a first load sensor) determines a first collet coupler torque acting on the first collet coupler and a processor determines an EMD torque acting on EMD 102 as a function of a first signal from the first torque sensor 182 (or more generally a first load sensor).

In one embodiment the second actuator 170 operatively engages and disengages the second collet coupler to prevent and allow rotation of the second collet coupler. In one embodiment the second collet coupler operatively pinches and unpinches the EMD 102 in the pathway to rotate the EMD 102 and a second torque sensor 184 (or more generally a second load sensor) determines a second collet coupler torque acting on the second collet coupler. A processor determines the EMD torque acting on the EMD 102 as a function of the first signal from the first torque sensor 182 (or more generally a first load sensor) and a second signal from the second torque sensor 184 (or more generally a second load sensor).

In one embodiment the processor determines a net collet torque applied to the collet for pinch and/or unpinching the EMD 102, where the net collet torque is the relative torque between the torque acting on the first collet coupler due to the first actuator 168 and the torque acting on the second collet coupler due to the second actuator 170.

In the embodiment shown in FIG. 9A first torque sensor 182 is mounted on the capstan of first actuator 168 and located above first actuator 168 and second torque sensor 184 is mounted on the capstan of second actuator 170 and located above second actuator 170. In one embodiment the first torque sensor 182 includes two parts, a first torque sensor rotating part that is mounted on the capstan of first actuator 168 and a first torque sensor housing that is mounted to the housing of first actuator 168 which is fixed to drive module base component 116. In one embodiment the second torque sensor 184 includes two parts, a second torque sensor rotating part that is mounted on the capstan of second actuator 170 and a second torque sensor housing that is mounted to the housing of second actuator 170 which is fixed to drive module base component 116. In an alternate embodiment at least one of the two torque sensors is placed in line with the capstan shaft driven by one of the actuators where the sensor rotates with the actuator shaft.

In the embodiment shown in FIG. 9B first torque sensor 182 is mounted between the housing of first actuator 168 and drive module base component 116 and located below first actuator 168 and second torque sensor 184 is mounted between the housing of second actuator 170 and drive module base component 116 and located below second actuator 170. In one embodiment at least one of the torque sensors is placed between the actuator and the drive module base component 116 of drive module 68 where the torque sensor supports the actuator in at least one direction.

Figure 9C:
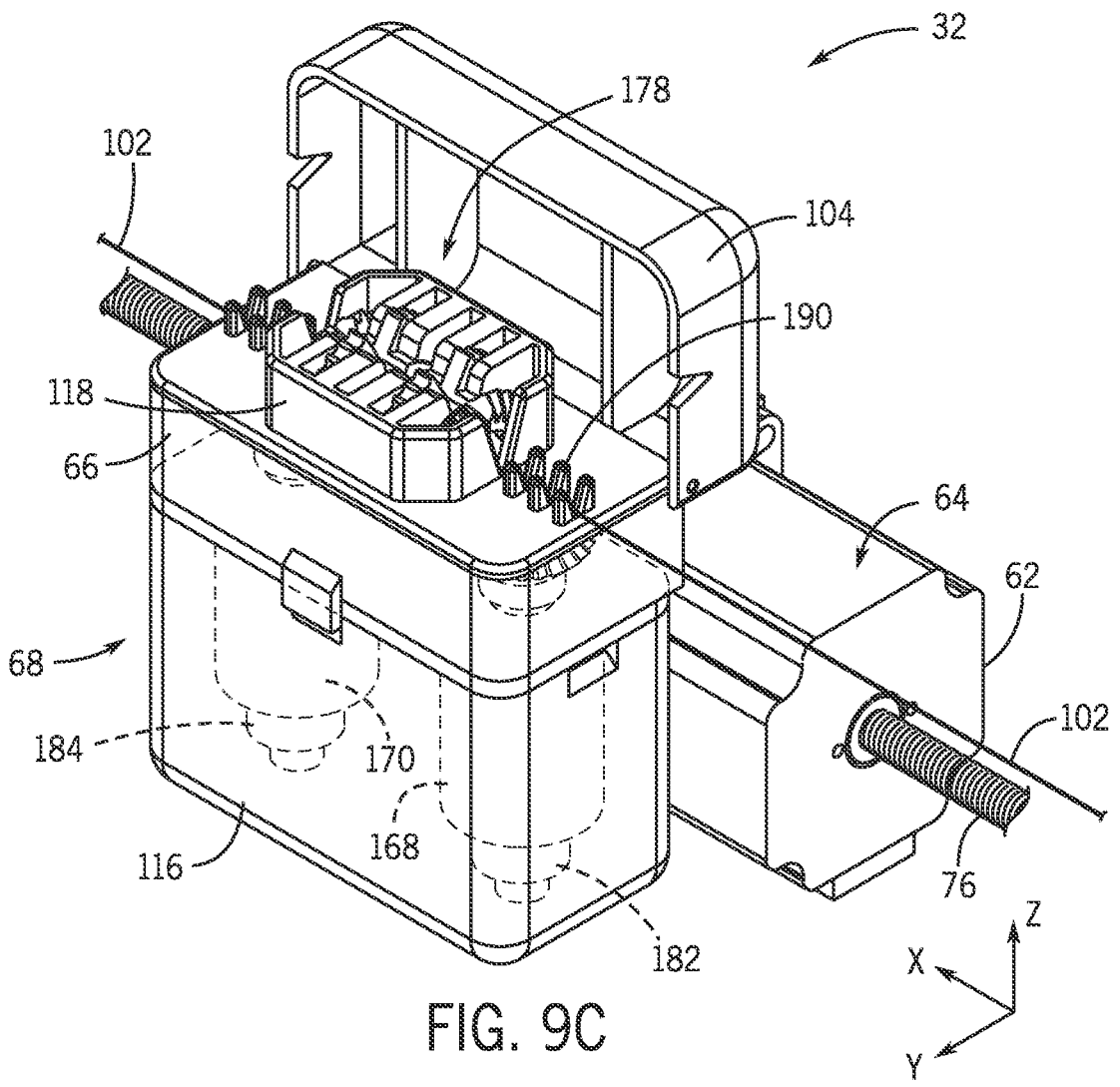
FIG. 9C is a schematic isometric view of a load sensing system of FIG. 9B.

Referring to FIG. 9C, an isometric view of the load sensing system of FIG. 9B is indicated. In the embodiment shown first torque sensor 182 is mounted on the capstan of first actuator 168 and located below first actuator 168 and second torque sensor 184 is mounted on the capstan of second actuator 170 and located below second actuator 170. In one embodiment at least one of the torque sensors is placed between the actuator and the drive module base component 116 of drive module 68 where the torque sensor supports the actuator in at least one direction.

Device module 32 includes a drive module 68 that translates along an axial direction of EMD 102 by actuation of a stage translation motor 64 that drives a stage drive mechanism 76 (such as a lead screw) relative to stage 62. Alternatively, the stage drive mechanism 76 (such as a lead screw) may be stationary and a stage translation motor 64 may rotate a nut on the lead screw directly or by use of a belt 114 (as shown in FIG. 4). The nut is in contact with drive module 68 through two thrust bearings and as the nut rotates on the lead screw it translates device module 32. Drive module 68 is constrained by a guide to move only linearly with respect to stage drive mechanism 76. Drive module 68 includes a drive module base component 116, a cassette 66, and a cassette housing 104. The cassette 66 includes a double bevel gear drive mechanism 178 that includes a collet 180 (not shown) and EMD guides 190. The EMD guides 190 include multiple pairs of guides that act as v-shaped notches and serve as an open channel for guiding EMD 102 through the drive system. Note that in operation the cassette housing 104 is rotated down to be in a closed position. The guides act as anti-buckling features. In one embodiment EMD guides 190 include multiple pairs of v-shaped notches or u-shaped channels that act as guides. The tops of the v-shaped or u-shaped channels may be chamfered to assist in loading the EMD 102. In one embodiment one pair of EMD guides 102 is used on the proximal side of the double bevel gear drive mechanism 178 and one pair of EMD guides 190 is used on the distal side of the double bevel gear drive mechanism 178. In one embodiment multiple pairs of EMD guides 190 are used on the proximal side of the double bevel gear drive mechanism 178 and multiple pairs of EMD guides 190 are used on the distal side of the double bevel gear drive mechanism 178.

Figure 9D:
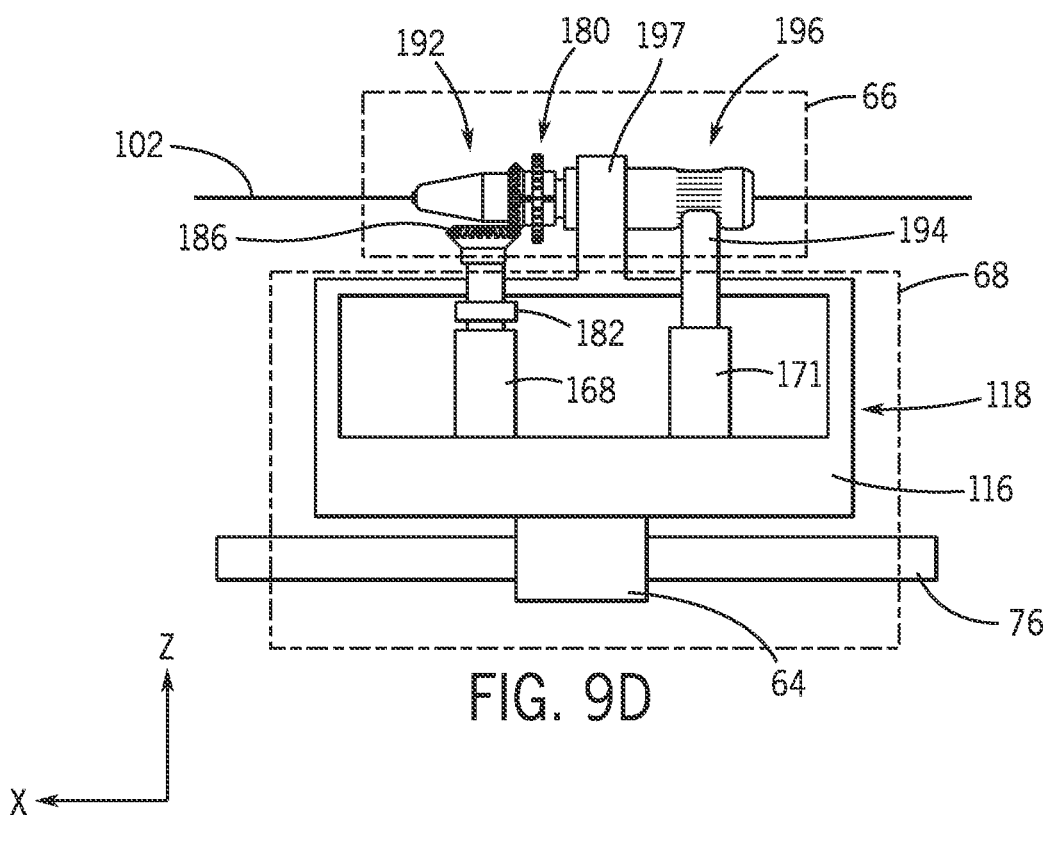
FIG. 9D is a schematic side view of an example embodiment of a load sensing system for a collet mechanism with a single torque sensor.

Referring to FIG. 9D, an embodiment of a torque sensing system using a first torque sensor 182 between a first actuator 168 and its capstan for locking/unlocking a collet 180 during operation is indicated. The capstan of first actuator 168 drives first driver gear 186 which is continuously engaged with a first portion 192 of the collet drive mechanism which is used to rotate the entire collet 180 with EMD 102 when the EMD is pinched in the collet. For unpinching EMD 102 a locking actuator 171 engages a locking/unlocking mechanism 194 to lock a second portion 196 of the collet drive mechanism preventing rotation of that portion to allow application of a differential torque on the two portions of collet 180 for pinching/unpinching EMD 102. In one embodiment locking/unlocking mechanism 194 is actuated by linear motion of locking actuator 171. In one embodiment locking/unlocking mechanism 194 is actuated by rotational motion of locking actuator 171. In one embodiment locking/unlocking mechanism 194 of collet 180 is accomplished by other methods such as engagement/disengagement of gear teeth or keys, frictional interfaces, etc.

Second portion 196 of the collet drive mechanism is held in position by a holding mount 197 integrally connected to drive module base component 116. Holding mount 197 allows second portion 196 of the collet drive mechanism to rotate freely about its longitudinal axis and constrains second portion 196 from motion in the longitudinal (axial) direction X and transverse directions Y and Z. In one embodiment holding mount 197 incorporates a rotational bearing to allow second portion 196 of the collet drive mechanism to rotate freely.

With locking actuator 171 having locking/unlocking mechanism 194 disengaged from second portion 196 of collet 180 during operation, the torque on EMD 102 can be determined by using one load sensor, namely first torque sensor 182, measuring the reaction torque on the continuously engaged first actuator 168. The measured reaction torque is used to determine the torque on EMD 102 when it is pinched in collet 180 and is used to determine the tightening torque of collet 180 during a reset state when the locking/unlocking mechanism 194 is engaged with the second portion 196 of collet 180.

The system includes a method of correction of parasitic loads that may corrupt the measurement of the actual torque acting on EMD 102. The system includes a method of correction for the measured reaction torque due to friction, including friction from gearing, that may corrupt the measurement of the actual torque acting on EMD 102 during the measurements (see equation (2)).

In one embodiment the cables of first actuator 168 and of locking actuator 171 and of first torque sensor 182 connecting to the load-sensed component are anchored on drive module base component 116 of the capital unit to isolate the load-sensed component from drag loads imparted by the cables.

Figure 9E:
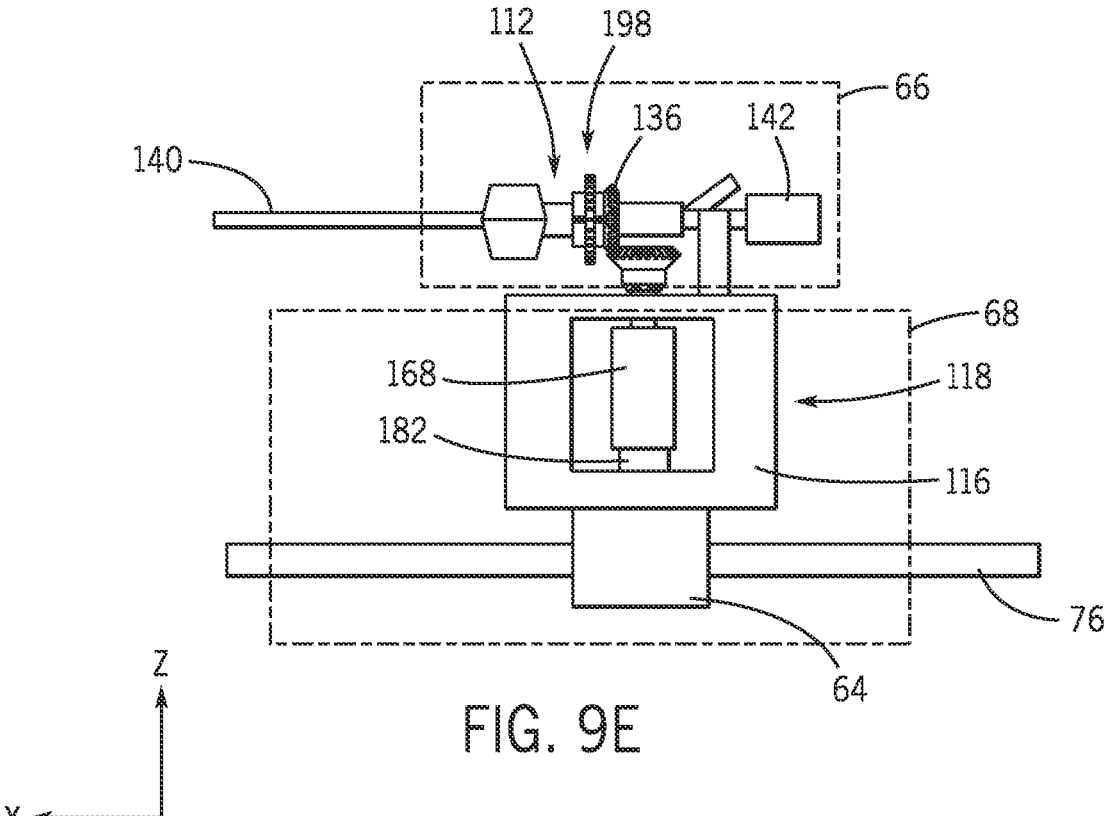
FIG. 9E is a schematic side view of an example embodiment of a load sensing system for a hub drive mechanism with a single torque sensor.

Referring to FIG. 9E, an embodiment of a torque sensing system using a first torque sensor 182 below a first actuator 168 on an EMD hub-drive mechanism 198 is indicated. In the embodiment of EMD hub-drive mechanism 198 shown a driven bevel gear 136 is connected to a hub 142 of EMD on-device adapter 112 and the torque acting on the EMD is determined using torque sensor 182 measuring the reaction torque of first actuator 168. In one embodiment torque-sensing can be accomplished indirectly, that is, without explicit use of torque sensor 182. For example, in one embodiment torque-sensing can be accomplished by measuring the electrical current of actuator 168, which can be related to the applied torque by the actuator. In one embodiment, the torque sensor 182 includes one or multiple force sensors that measure reaction forces and a processing unit that determines torque based on the measured reaction forces. Torque about an axis may be calculated as the cross product of the position vector for the point of application of the force (relative to axis of torque measurement) and the reaction force vector.

Figure 9F:
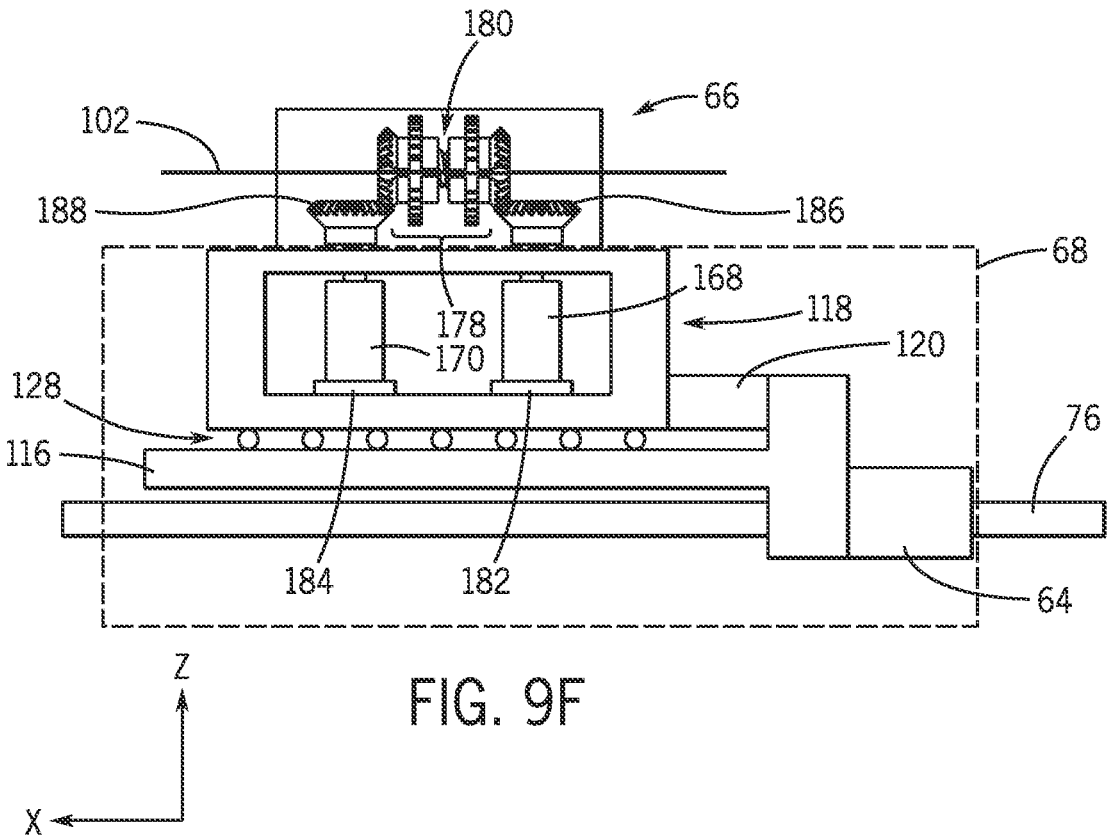
FIG. 9F is a schematic side view of another embodiment of a load sensing system of FIG. 9B for measuring force and torque on an EMD.

Referring to FIG. 9F, an embodiment of FIG. 9B is indicated in which a load sensor 120 is used between drive module base component 116 and load-sensed component 118 to measure the force applied to EMD 102. A first torque sensor 182 at the lower end of first actuator 168 and a second torque sensor 184 at the lower end of second actuator 170 are used to determine the torque applied to EMD 102. In one embodiment first torque sensor 182 and second torque sensor 184 are located in line with the capstan shafts of first actuator 168 and second actuator 170, respectively, as indicated in FIG. 9A.

In one embodiment a linear bearing support 128 is used to support the load-sensed component 118 in directions other than the load-measurement directions.

Figures 10A, 10B:
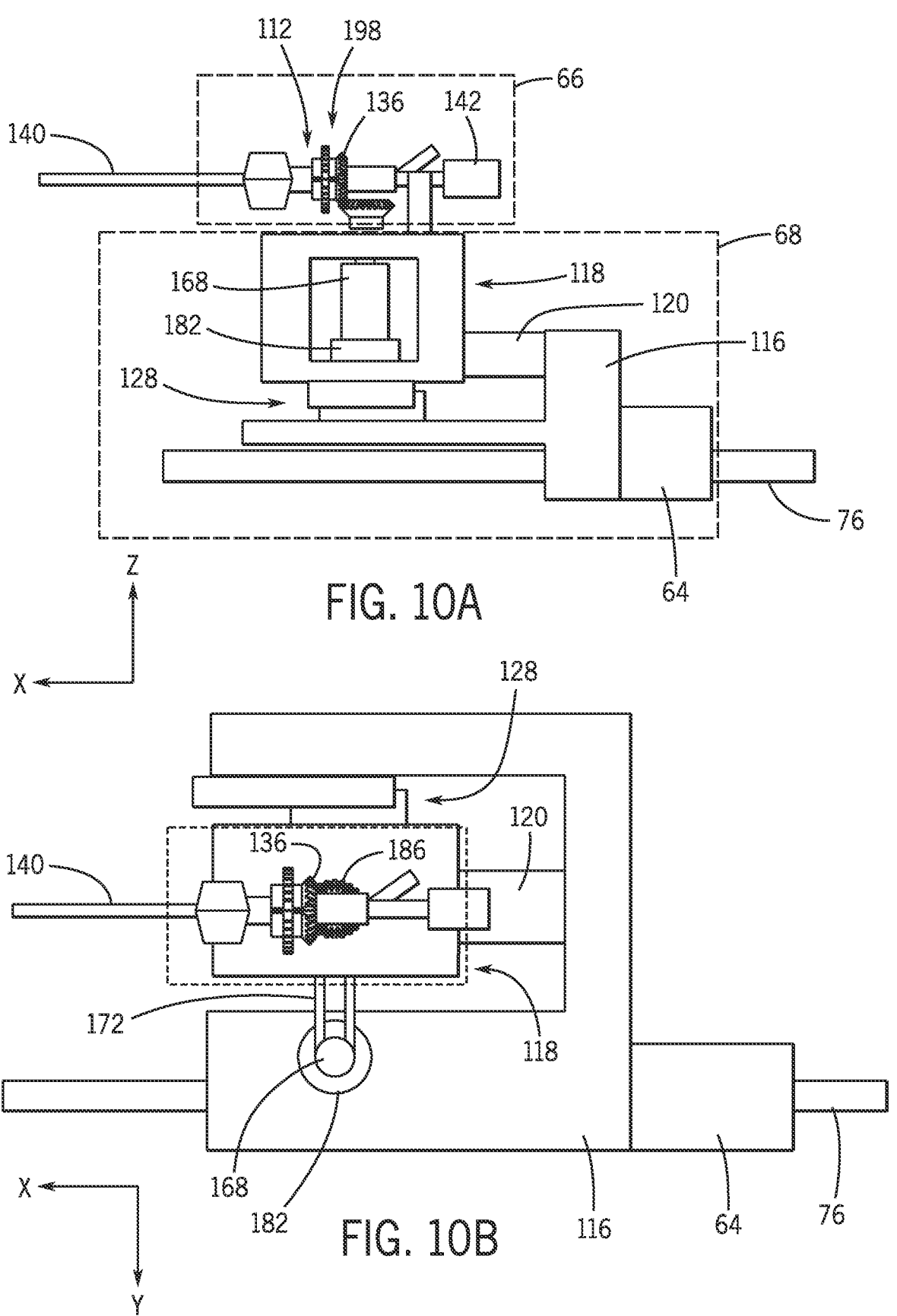
FIG. 10A is a schematic side view of another embodiment of a load sensing system for measuring force and torque on an EMD.
FIG. 10B is a schematic top view of another embodiment of a load sensing system for measuring force and torque on an EMD.

Referring to FIG. 10A, an embodiment of a load sensing system for an EMD hub-drive mechanism is indicated in which force, torque, or force and torque components acting on an EMD are determined by a load sensor 120 between the drive module base component 116 and the load-sensed component 118 and a first torque sensor 182 at the bottom of first actuator 168. In one embodiment load sensor 120 is a multi-axis sensor measuring at least a force component and a torque. In one embodiment load-sensed component 118 is fully supported by load sensor 120 and no bearing is used. In one embodiment a linear bearing 128 is used to support load-sensed component 118 at least in one non-measurement direction.

In one embodiment, load sensor 120 is a force sensor measuring the force acting on the EMD and a torque sensor 182 is used to determine the torque acting on the EMD. In one embodiment a bearing 128 supports the load-sensed component 118 in all directions other than the force measurement direction. For example, the bearing is a linear slide allowing motion parallel to the direction of motion of stage drive mechanism 76.

Referring to FIG. 10B, one embodiment of FIG. 10A is shown in which first actuator 168 is located outside the load-sensed component 118 to reduce parasitic loads such as inertia loads applied to load sensor 120. Also, the torque acting on the EMD may be determined using a first torque sensor 182 between the first actuator 168 and the drive module base component 116 at least in one direction. Alternatively, torque sensor 182 may be located in the drive train between the first actuator 168 and the on-device adapter in the load-sensed component 118.

Figure 11:
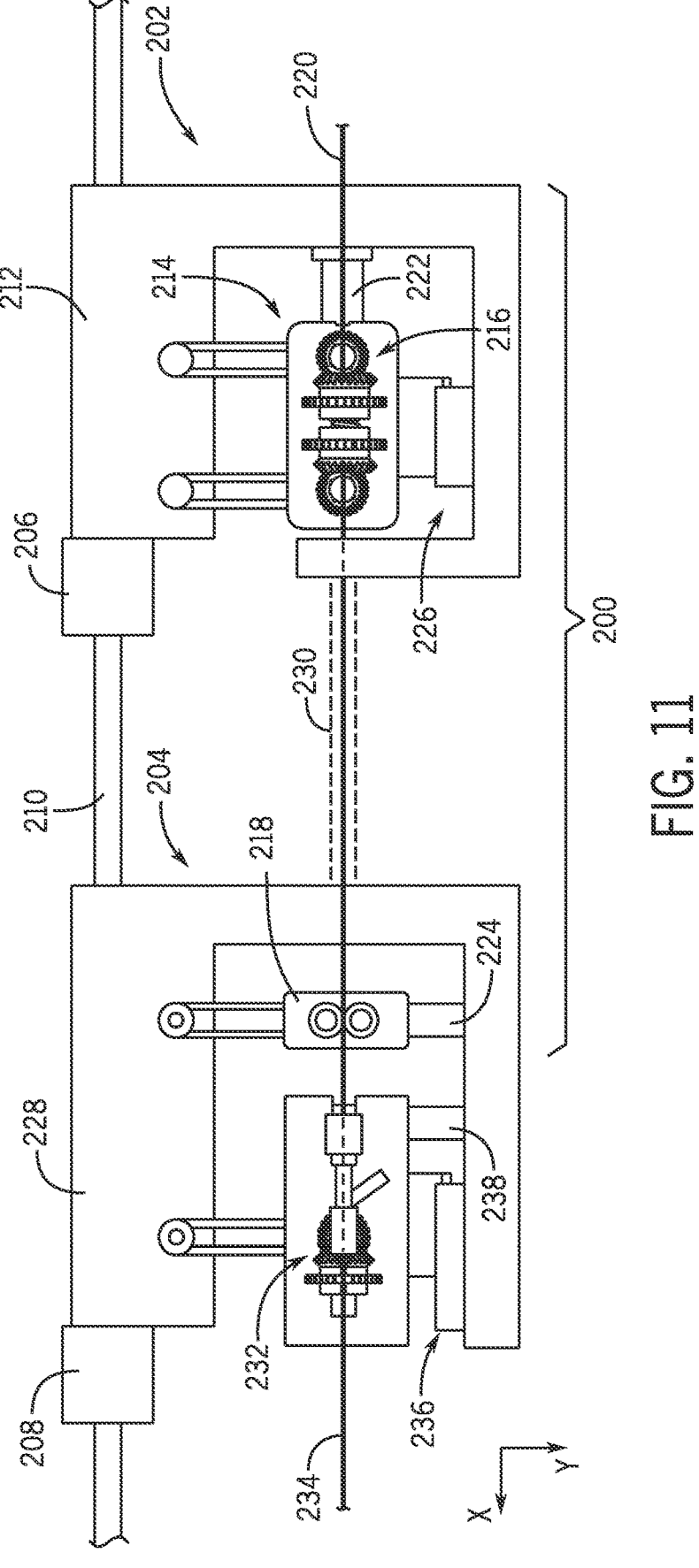
FIG. 11 is schematic top view of an embodiment of a load sensing system for measuring force and torque on an EMD in a robotic system with reset motion using tire drives distal to a first on-device adapter.

Referring to FIG. 11, a load-sensed drive system with reset motion 200 is shown which includes a first drive module 202, a first load sensor 222, a second drive module 204, and a second load sensor 224. First drive module 202 includes a first stage translation motor 206 and second drive module 204 includes a second stage translation motor 208. First stage translation motor 206 and second stage translation motor 208 operate independently and enable first drive module 202 and second drive module 204, respectively, to translate relative to a stage drive mechanism 210. In one embodiment stage drive mechanism 210 is a lead screw.

First drive module 202 includes a first drive module base component 212 and a cassette 214 housing a first on-device adapter 216 that releasably grips a first EMD 220 and may advance first EMD 220 (that is, translate EMD 220 in the distal longitudinal direction), retract first EMD 220 (that is, translate EMD 220 in the proximal longitudinal direction), rotate first EMD 220 clockwise, and rotate first EMD 220 counterclockwise. In one embodiment first on-device adapter 216 is a double bevel gear drive mechanism.

The operation of first on-device adapter 216 is described in U.S. Provisional Application No. 62/874,173 which was incorporated herein by reference above. See generally paragraphs [0317]-[0322] and Figures G2A-G2D of the '173 application.

In a pinched state, first on-device adapter 216 pinching first EMD 220 moves first EMD 220 a distance in one direction, and then in a reset state, first on-device adapter 216 releases first EMD 220 and moves to a reset position in a direction opposite the one direction. For example, first on-device adapter 216 pinches first EMD 220 and then moves first EMD 220 in a distal direction. In a reset state, first on-device adapter 216 unpinches first EMD 220 and then first on-device adapter 216 returns to a reset position, that is, first on-device adapter 216 moves in a proximal direction after unpinching EMD 220. In one embodiment, during the reset state EMD 220 is clamped by a second on-device adapter 218. In another embodiment the first EMD 220 stays in place during the reset state due to friction between the first EMD 220 and the second EMD 234 and/or the hemostasis valve on the second EMD 234. Once first on-device adapter 216 is moved to the reset position, first on-device adapter 216 repinches first EMD 220. Load-sensed drive system with reset motion 200 may repeat the sequence of pinched state and reset state.

A device support 230, between first on-device adapter 216 and second on-device adapter 218, prevents EMD 220 from buckling.

First on-device adapter 216 is a first load-sensed component. A first load sensor 222 detects the load acting on first on-device adapter 216 corresponding to the load applied to first EMD 220 at first on-device adapter 216. Second on-device adapter 218 is a second load-sensed component. A second load sensor 224 detects the load acting on second on-device adapter 218 corresponding to the load applied to first EMD 220 at the second on-device adapter 218. In one embodiment the load measured can be an axial force. In one embodiment the load measured can be a torque. In one embodiment the load measured can have one component of axial force and one component of torque.

In one embodiment, first on-device adapter 216 is supported by a first linear bearing 226 in transverse directions, which integrally connects first on-device adapter 216 and first drive module base component 212 in all directions other than load measurement direction(s). In load measurement direction(s), first on-device adapter 216 is supported solely by a first load sensor 222 which connects first on-device adapter 216 and first drive module base component 212 in load measurement direction(s). First load sensor 222 is oriented along the longitudinal direction of first EMD 220 and positioned between first on-device adapter 216 (first load-sensed component) and first drive module base component 212. First load sensor 222 measures the load acting on first on-device adapter 216 and thus the load acting on first EMD 220 when gripped by first on-device adapter 216.

Second load sensor 224 is positioned between second on-device adapter 218 and second drive module base component 228 of second drive module 204. Second load sensor 224 measures the load acting on second on-device adapter 218 and thus the load acting on first EMD 220 when pinched or fixed by second on-device adapter 218.

In one embodiment second on-device adapter 218 is a clamp that fixes the location of first EMD 220 relative to second on-device adapter 218 while first on-device adapter 216 is in reset state. In another embodiment second on-device adapter 218 is a drive that imparts linear movement to first EMD 220 relative to second on-device adapter 218. In one embodiment second on-device adapter 218 includes two other engagement surfaces (wheels or paddles) that impart movement to first EMD 220. In one embodiment second on-device adapter 218 can move the EMD 220 linearly and rotationally.

In one embodiment, no second on-device adapter 218 and second load sensor 224 is used, and first EMD 220 stays in place during the reset state due to friction between first EMD 220 and second EMD 234 and/or a hemostasis valve.

A processor (not shown) distinguishes pinched state from reset state using a state sensor in the drive mechanism and determines the actual load on first EMD 220. In one embodiment the processor determines actual load on first EMD 220 solely during pinched state while no load information is provided during the reset state. In one embodiment the processor determines actual load on first EMD 220 of first on-device adapter as a function of load data from first load sensor 222, load data from second load sensor 224, state of first on-device adapter 216, and state of second on-device adapter 218, where state refers to whether the on-device adapter is gripping or ungripping EMD 220, rotating clockwise, counterclockwise, or not rotating, etc.

A load feedback system indicates the load information to a user. In one embodiment, load feedback system indicates the actual load on first EMD 220 and state of first on-device adapter 216 during pinched state and indicates only the state of first on-device adapter 216 during reset state (e.g. when no second on-device adapter and/or no second load sensor is used). This will prevent the feedback system to indicate false load measurements sensed while EMD 220 is ungripped by first on-device adapter 216. In one embodiment feedback system indicates the actual load on first EMD 220 of first on-device adapter 216 and state of the first on-device adapter 216 during both pinched state and reset state.

Referring to FIG. 11, in one embodiment of a reset load sensing system 200 a first drive module 202 includes a first on-device adapter 216 operatively engaging the EMD 220 and a second drive module 204 having a second on-device adapter 218 releasably engaging the EMD 220, wherein a reset state includes moving the first on-device adapter 216 relative to the second drive module 204 between an extended position and a reset position. In this embodiment a first load sensor 222 is operatively connected to the first on-device adapter 216 and first drive module 202 and a second load sensor 224 is operatively connected to the second on-device adapter 218 and second drive module 204. A processor (not shown) receives a first signal from the first load sensor 222 and a second signal from the second load sensor 224 and determines the actual load on the EMD as a function of the first signal, second signal and the state of the first on-device adapter 216 and the state of the second on-device adapter 218. In one embodiment the first on-device adapter includes a collet. In one embodiment the second on-device adapter includes a clamp having a pair of rolling members.

In one embodiment the distance between the first on-device adapter 216 and the second on-device adapter 218 is greater in the reset position than in the extended position when the apparatus is advancing the EMD 220 and the distance between the first on-device adapter 216 and the second on-device adapter 218 is greater in the extended position than the reset position when the apparatus is retracting the EMD 220. In one embodiment the state of the first on-device adapter 216 includes a pinch state and an unpinched state, and the second on-device adapter 218 includes a grip state and an ungripped state.

In one embodiment a first drive module includes a first on-device adapter and a second drive module, where the first on-device adapter has a first state operatively engaging the EMD and a second state operatively disengaging the EMD and where the second on-device adapter has a third state engaging the EMD and a fourth state disengaging the EMD. A reset state includes moving the first on-device adapter relative to the second drive module between an extended position and a reset position. A second load sensor is operatively connected to the second on-device adapter and second drive module. A processor receives a first signal from the load sensor and a second signal from the second load sensor and determines the actual load on the EMD as a function of the first signal, second signal and whether the first on-device adapter is in first state or second state and whether the second on-device adapter is in the third state or a fourth state. In one embodiment, the first state of the first on-device adapter is a pinch state and the second state of the first on-device adapter is an unpinched state, and the third state of the second on-device adapter is a grip state, and the fourth state of the second on-device adapter is an ungripped state.

Referring to FIG. 11, the system includes a third on-device adapter 232 to grip and manipulate a second EMD 234 that is coaxial with first EMD 220. In one embodiment, third on-device adapter 232 is supported by a second linear bearing 236 in transverse directions, which integrally connects third on-device adapter 232 and second drive module base component 228 in all directions other than load measurement direction(s) for second EMD 234. In load measurement direction(s), third on-device adapter 232 is supported solely by a third load sensor 238 which connects third on-device adapter 232 and second drive module base component 228 in load measurement direction(s). A third load sensor 238 is positioned between third on-device adapter

232 and second drive module base component 228. Third load sensor 238 measures the load acting on third on-device adapter 232 and thus the load acting on second EMD 234 when gripped by third on-device adapter 232.

Figure 12A:
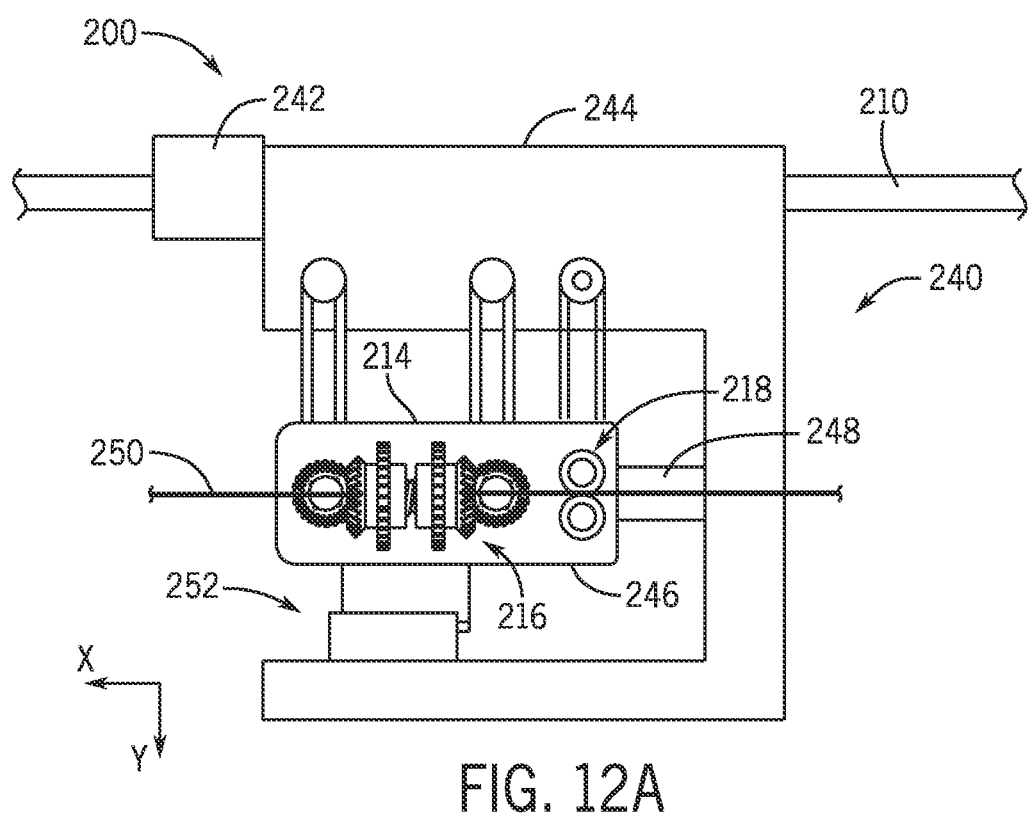
FIG. 12A is schematic top view of an embodiment of a load sensing system for measuring force and torque on an EMD in a robotic system with reset motion using tire drives proximal to a first on-device adapter.
Figure 12B:
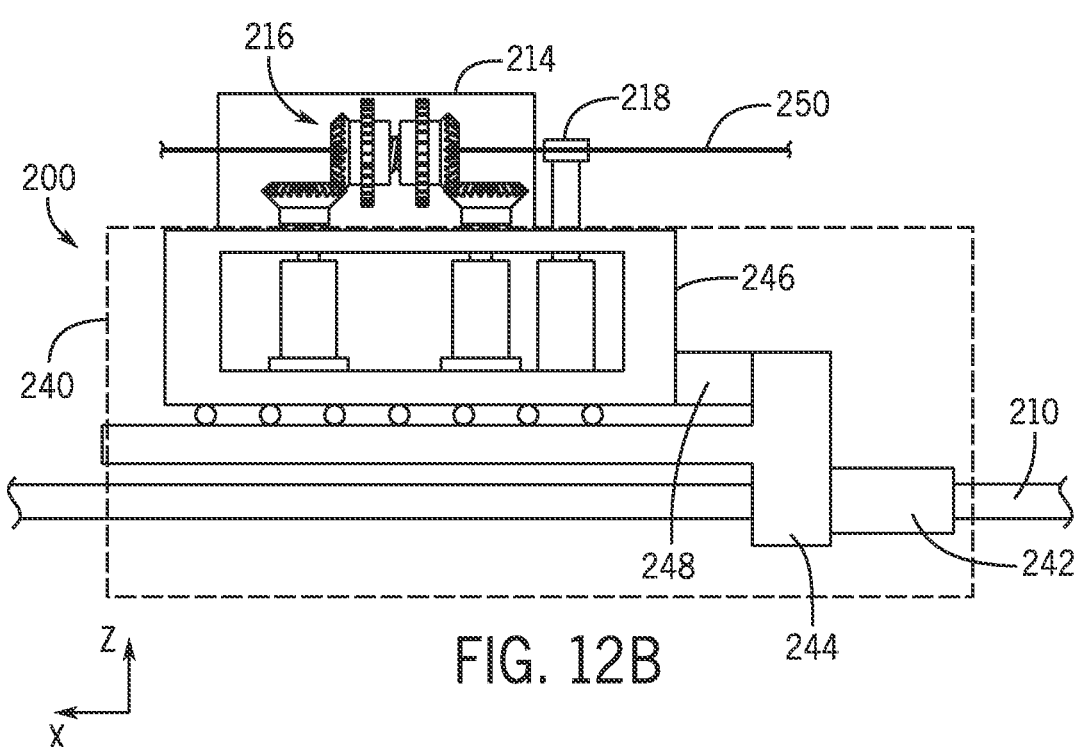
FIG. 12B is schematic side view of an example embodiment of the load sensing system of FIG. 12A.

Referring to FIGS. 12A and 12B, another embodiment of a load-sensed drive system with reset motion 200 load-sensed drive system with reset motion 200 includes a single drive module 240. Drive module 240 includes a stage translation motor 242 that enables drive module 240 to translate relative to a stage drive mechanism 210. In one embodiment stage drive mechanism 210 is a lead screw.

Drive module 240 includes a drive module base component 244 and a cassette 214 housing a first on-device adapter 216 that releasably grips an EMD 250 and may advance EMD 250 (that is, translate EMD 250 in the distal longitudinal direction), retract EMD 250 (that is, translate EMD 250 in the proximal longitudinal direction), rotate EMD 250 clockwise, and rotate EMD 250 counterclockwise. In one embodiment, the translational degree of freedom on EMD 250 is achieved by moving the drive module 240 along stage drive mechanism 210 while EMD 250 is gripped by first on-device adapter 216. In one embodiment first on-device adapter 216 is a double bevel gear drive mechanism 230.

The operation of first on-device adapter 216 is described in U.S. Provisional Application No. 62/874,173 which was incorporated herein by reference above. See generally paragraphs [0317]-[0322] and Figures G2A-G2D of the '173 application.

Drive module base component 244 also includes a second on-device adapter 218. In the embodiment of FIGS. 12A and 12B, second on-device adapter 218 is proximal of first on-device adapter 216.

In pinched state, first on-device adapter 216 pinching EMD 250 moves EMD 250 a distance in one direction and then first on-device adapter 216 releases EMD 250 and moves to a reset position in a direction opposite the one direction. For example, in pinched state, first on-device adapter 216 pinching EMD 250 moves EMD 250 in a distal direction. In one embodiment, the translational degree of freedom on EMD 250 is achieved by moving the drive module 240 along stage drive mechanism 210 while EMD 250 is pinched by first on-device adapter 216. In a reset state, first on-device adapter 216 unpinches EMD 250 and then first on-device adapter 216 returns to a reset position, that is, first on-device adapter 216 moves in a proximal direction after unpinching EMD 250. In one embodiment EMD 250 is clamped by a second on-device adapter during both pinched state and reset states. In one embodiment, second on-device adapter 218 is one or multiple pairs of tires that can move EMD 250 linearly by rotating about their axes. The two tires in each pair of tires rotate at the same rate but in opposite directions to move EMD 250 linearly in proximal or distal direction. In pinched state, second on-device adapter 218 does not move EMD 250 relative to second on-device adapter 218. In reset state EMD 250 is clamped by second on-device adapter 218 and second on-device adapter 218 moves EMD 250 relative to second on-device adapter 218 so that the absolute position of EMD 250 is maintained as drive module 240 moves along stage drive mechanism 210 to reset position. Once first on-device adapter 216 is moved to the reset position, first on-device adapter 216 repinches EMD 250. Load-sensed drive system with reset motion 200 may repeat the sequence of pinched state and reset state.

First on-device adapter 216 and second on-device adapter 218 are mounted on a load-sensed component 246. A load sensor 248 detects the load acting on load-sensed component 246. In one embodiment load sensor 248 is oriented along the longitudinal direction of EMD 250 and positioned between load-sensed component 246 and drive module base component 244. Load sensor 248 measures the load acting on EMD 250 both in pinched and reset states.

In one embodiment load-sensed component 246 is supported by a bearing 252 in one or multiple directions other than measurement direction(s).

Figure 13A:
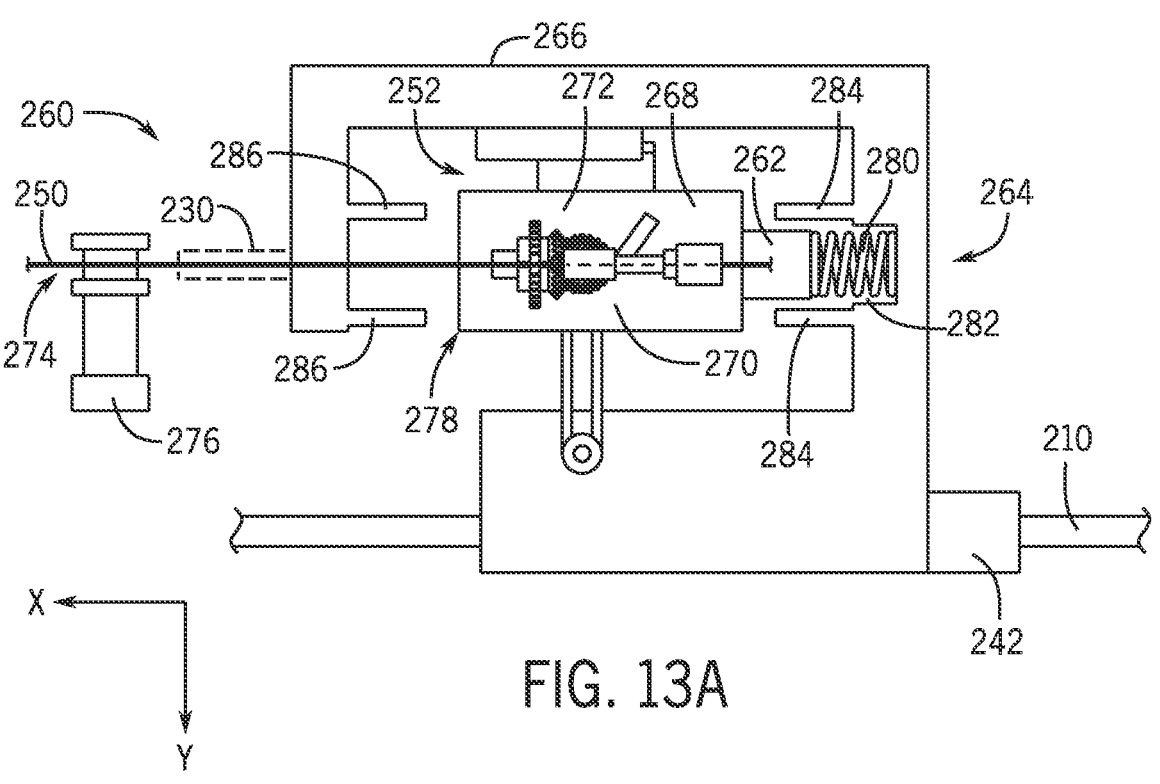
FIG. 13A is schematic top view of an embodiment of a load sensing system for measuring force and torque on an EMD in a robotic system with automated calibration and overload protection of a sensor shown in a neutral (no load) position.
Figure 13B:
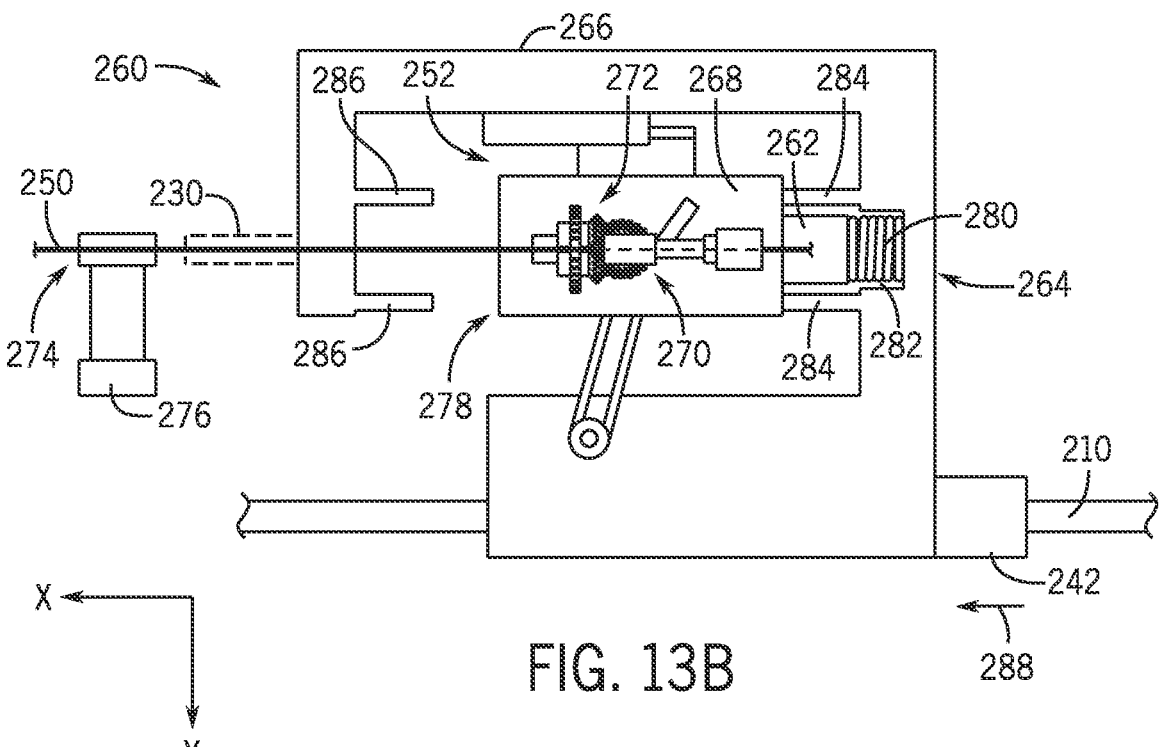
FIG. 13B is schematic top view of an embodiment of the load sensing system of FIG. 13A shown in a loaded position.

Referring to FIG. 13A and FIG. 13B, a load sensing system 260 with automated calibration of a load sensor 262 and overload protection of load sensor 262 includes a single drive module 264. Drive module 264 includes a stage translation motor 242 that enables drive module 264 to translate relative to a stage drive mechanism 210. In one embodiment stage drive mechanism 210 is a lead screw.

Drive module 264 includes a drive module base component 266 and a cassette 268 housing a first on-device adapter 270 that releasably grips an EMD 250 and may advance EMD 250 (that is, translate EMD 250 in the distal longitudinal direction), retract EMD 250 (that is, translate EMD 250 in the proximal longitudinal direction), rotate EMD 250 clockwise, and rotate EMD 250 counterclockwise. In one embodiment first on-device adapter 270 is a single bevel gear drive mechanism 272 (similar to that used in FIG. 9E).

The operation of first on-device adapter 270 is described in U.S. Provisional Application No. 62/874,173 which was incorporated herein by reference above. See generally paragraphs [0317]-[0322] and Figures G2A-G2D of the '173 application.

In one embodiment load sensing system 260 also includes a second on-device adapter 274. In the embodiment of FIGS. 13A and 13B, second on-device adapter 274 is a holding clamp located distal of first on-device adapter 270. Second on-device adapter 274 is mounted to a second on-device adapter base 276 that is fixed relative to linear member or rail 60 (see FIG. 3).

A device support 230, between first on-device adapter 270 and second on-device adapter 274, prevents EMD 250 from buckling.

First on-device adapter 270 is mounted on a load-sensed component 278. A load sensor 262 detects the load acting on load-sensed component 278. In one embodiment load sensor 262 is oriented along the longitudinal direction of EMD 250 and positioned longitudinally between load-sensed component 278 and an elastic component 280. Elastic component 280 is sandwiched between load sensor 262 and a pocket 282 in drive module base component 266. In one embodiment elastic component 280 is a mechanical helical spring with known spring stiffness. In one embodiment pocket 282 is a circular recess in drive module base component 266 into which seats a mechanical helical spring with known spring stiffness. In one embodiment elastic component 280 has a constant elastic stiffness that is known. In one embodiment elastic component 280 has a nonlinear elastic stiffness that is known, that is, its force vs. displacement characteristic is known.

Referring to FIG. 13A, load-sensed component 278 is supported solely by load sensor 262 and elastic component 280 in the load measurement direction. In one embodiment first on-device adapter 270 is supported in transverse directions (non-load-measurement directions) by a bearing 252, which integrally connects load-sensed component 278 and drive module base component 266.

Integrally connected to drive module base component 266 are mechanical stops 284 and mechanical stops 286 in proximal and distal longitudinal directions, respectively, of the load-sensed component 278. In one embodiment mechanical stops include a single mechanical stop. In one embodiment mechanical stops include more than one mechanical stop. Mechanical stops 284 are on the side of drive module base component 266 closest to load sensor 262 and are separated one from another a distance greater than the transverse dimension of load sensor 262 such that it can surround it. In one embodiment mechanical stops 284 and mechanical stops 286 are rod extensions oriented longitudinally from the drive module base component 266. In one embodiment mechanical stops 284 and mechanical stops 286 are flange extensions oriented longitudinally from the drive module base component 266. In one embodiment mechanical stops 284 and mechanical stops 286 and drive module base component 266 are made of the same material as one piece. In one embodiment mechanical stops 284 and mechanical stops 286 and drive module base component 266 are made of different materials and integrally connected to form one piece. The purpose of mechanical stops 284 is to protect load sensor 262 from being overloaded, that is, being exposed to forces beyond the operating range of the sensor or causing damage due to forces that exceed the upper limits of the sensor when a push force is applied to EMD 250 herein defined as "overload protection of the sensor". The purpose of mechanical stops 286 is to limit the range of longitudinal motion of load-sensed component 278 relative to drive module base component 266 when a pull force is applied to EMD 250.

Referring to FIG. 13A, load sensing system 260 is indicated in a neutral position of load-sensed component 278, that is, with no load applied to load-sensed component 278. In a neutral position there is no contact between load-sensed component 278 and mechanical stops 284. Referring to FIG. 13B, load sensing system 260 is indicated in a maximum loaded position of load-sensed component 278, that is, with maximum allowable push load applied to load sensor 262, load-sensed component 278 makes contact with mechanical stops 284 at the load sensor 262 side of drive module 264. In one embodiment a second sensor can be a contact detection sensor to detect contact between the load-sensed component 278 and the mechanical stops 284. Different type of sensors may be used as a contact detection sensor including but not limiting to distance sensors, load sensors, optical sensors, electronic circuit-based contact detection sensors. The motion of load-sensed component relative to mechanical stops 284 is proportional to load applied to EMD. Given the stiffness of elastic component 280, the gap between load-sensed component 278 and mechanical stops 284 in no load condition (i.e. when elastic component has its neutral length) is selected so that the gap is closed at maximum allowable load due to deflection of elastic component 280. Maximum allowable load is defined as the maximum load that is acceptable to be applied to load sensor 262.

The process for automated calibration of load sensor 262 and overload protection of load sensor 262 includes two steps as follows. Step 1 is to eliminate zero offset. This is done by measuring force from load sensor 262 when no load is applied to EMD 250; i.e. elastic component 280 has its neutral length. The load indicated by the load sensing system should be zero since no load is applied to EMD 250, therefore, if the indicated load is non-zero, the load measured by load sensor 262 is subtracted by that non-zero value. Step 2 is to correct the calibration factor or relation between actual force acting on EMD 250 and force measured by load sensor 262. From the neutral position, second on-device adapter 274, such as a holding clamp, clamps EMD 250 making it stationary. In one embodiment Step 2 is to correct for any error, if it exists, between the force measured by load sensor 262 and the actual force acting on EMD 250. Since EMD 250 is stationary, load-sensed component 278 is also stationary. Next, a force 288 is applied to EMD 250 by driving stage translation motor 242 and pushing load-sensed component 278 (which contains first on-device adapter 270) into elastic component 280. Reaction force of force 288, in turn, is applied to elastic component 280. Due to reaction force of force 288, elastic component 280 is deflected (that is, compressed). The amount of deflection increases with magnitude of force 288 until there is a hard contact between mechanical stops 284 at load sensor side and drive module base component 266. A processor (not shown) then compares the measured force from load sensor 262 with force 288, which is known since the stiffness of elastic component 280 is known and the deflection of load-sensed component 278 is known (i.e. the initial gap load-sensed component 278 and mechanical stops 284 is known) and applying Hookean theory, that is, elastic force equals elastic stiffness multiplied by deflection of elastic member. The processor can then calculate any necessary correction factor of measured data from load sensor 262 such that load sensor 262 is calibrated.

In one embodiment load sensing system 260 does not have a second actuator, and the second step of calibration is done manually by pushing load-sensed component 278 manually towards mechanical stops 284 until they make contact. In contact state, processor compares the measured force by load sensor 262 with known force 288 and calculates any necessary correction factor of measured data from load sensor 262 such that load sensor 262 is calibrated.

In one embodiment, the same method is used for rotational degree of freedom for calibration and overload protection of a torque sensor. In such system mechanical stops and torsional springs are used where mechanical stops limit the angular displacement of load-sensed component 278.

Referring to FIGS. 13A and 13B discussed herein above, an apparatus for calibrating a load sensor 262 is indicated in which a drive module 264 includes a drive module base component 266, a load-sensed component (not shown), a load sensor 262 and an elastic component 280 having a known stiffness. The elastic component 280 is intermediate the load sensor 262 and the drive module base component 266. A cassette 268 is removably secured to the drive module 264. The cassette 268 includes a housing and an isolated component movable within the housing and is configured to receive an elongated medical device (EMD) 250.

In one embodiment a mechanical stop 284 limits movement of the isolated component relative to one of the housing and the drive module base component 266 in the direction of the elastic component 280 limiting the maximum deflection of the elastic component 280 to a known distance between the mechanical stop 284 and the isolated component. In one embodiment a distance between the mechanical stop 284 and the load-sensed component is predetermined to limit a maximum load applied to the load sensor 262 such that the load sensor 262 is protected from being overloaded.

In one embodiment a second sensor detects contact between the load-sensed component and the mechanical stop 284. In one embodiment the second sensor is a motion sensor. In one embodiment a processor is used to determine and remove zero offset from a measurement from the load sensor 262, where zero-offset refers to the bias in the measured load indicating an apparent load when no load is applied. The process of sensor calibration corrects for the zero-offset such that when no load is applied the load sensing system indicates zero load. In one embodiment a processor is used to correct a calibration factor by comparing a measured load and a known load. In one embodiment calibration of the load sensor 262 is accomplished manually by pushing the load-sensed component towards the mechanical stop or stops 284 until it contacts the mechanical stop or stops 284. In one embodiment calibration of the load sensor 262 is accomplished automatically. In one embodiment calibration of the load sensor 262 is accomplished automatically by a mechanism that is used to clamp an EMD 250. In one embodiment calibration of the load sensor 262 is accomplished automatically by a mechanism that is used to clamp an EMD 250 where the EMD 250 is supported by a device support. In one embodiment calibration of the load sensor 262 is accomplished automatically with a locking mechanism fixing the load-sensed component in place independent of the drive module base component 266. In one embodiment calibration of the load sensor 262 is accomplished automatically and there is overload protection of the load sensor 262 and the load sensor 262 measures an axial force acting on the EMD 250. In one embodiment calibration of the load sensor 262 is accomplished automatically and there is overload protection of the load sensor 262 and the load sensor 262 measures a torque acting on EMD 250 about the EMD longitudinal axis. In one embodiment calibration of the load sensor 262 is accomplished automatically and there is overload protection of the load sensor 262 and the load sensor 262 measures an axial force acting on the EMD 250 and measures a torque acting on EMD 250 about the EMD longitudinal axis.

Figures 14A, 14B:
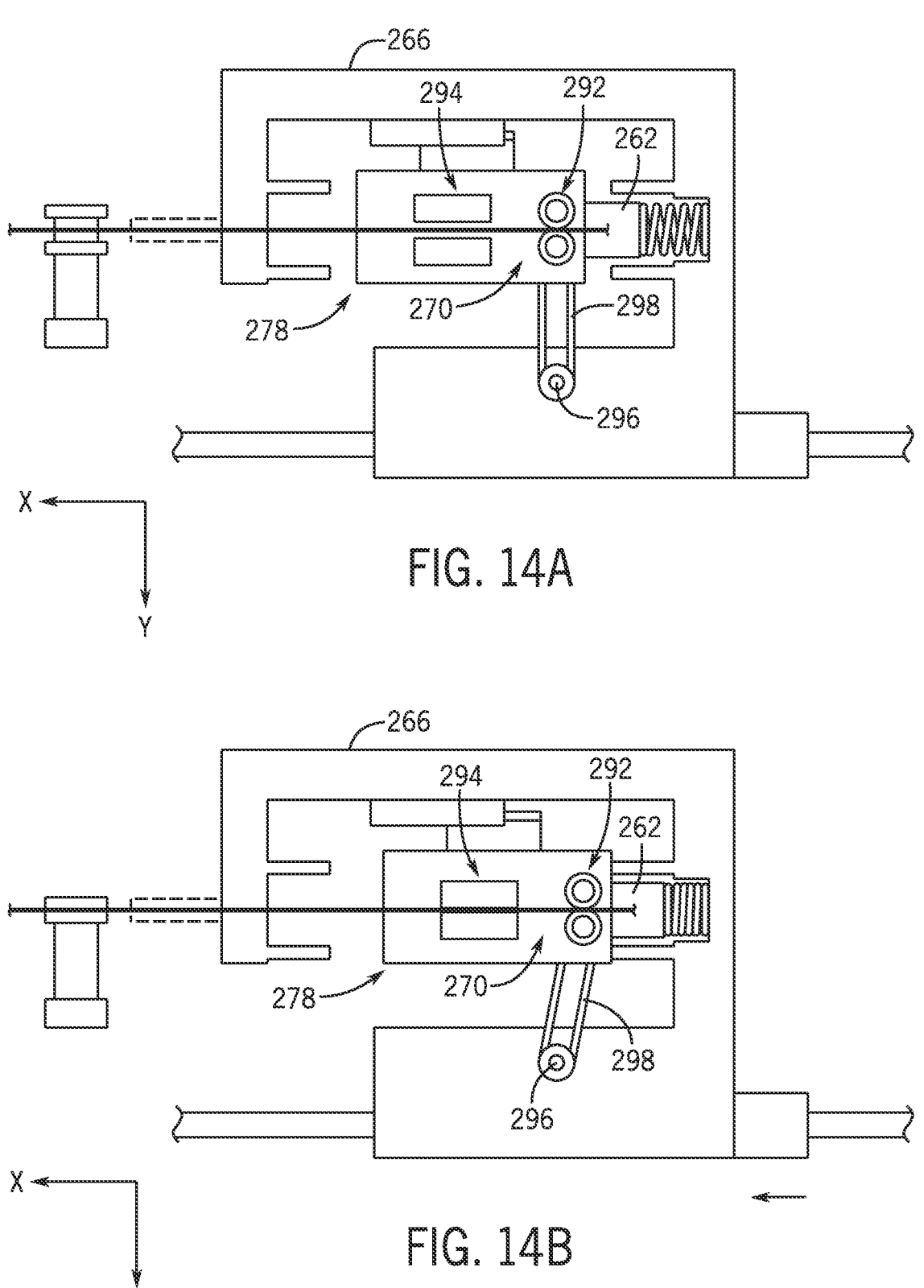
FIG. 14A is schematic top view of another embodiment of a load sensing system for measuring force and torque on an EMD in a robotic system with automated calibration and overload protection of a sensor shown in a neutral (no load) position.
FIG. 14B is schematic top view of an embodiment of the load sensing system of FIG. 14A shown in a loaded position.

Referring to FIG. 14A and FIG. 14B, components of the load sensing system are the same as components of the load sensing system of FIG. 13A and FIG. 13B except for an alternate embodiment of first-on-device adapter 270.

Referring to FIG. 14A and FIG. 14B, a load sensing system with automated calibration and overload protection of its load sensor includes a first on-device adapter 270 that is a tire drive mechanism 292 and a clamp 294. Tire drive mechanism 292 is driven by a drive actuator 296 mounted on drive module base component 266. Drive actuator 296 transfers power to tire drive mechanism 292 by a power train medium 298 that does not impart a significant load on the load-sensed component in the measurement direction (e.g. no force in X-axis direction). In one embodiment, power train medium 298 is a belt that wraps around and is driven by a pulley attached to drive actuator 296.

Referring to FIG. 14A, which is an alternate embodiment of FIG. 13A, the load sensing system is indicated in a neutral position of load-sensed component 278, that is, with no load applied to load-sensed component 278. Referring to FIG. 14B, which is an alternate embodiment of FIG. 13B, the load sensing system is indicated in maximum loaded position of load-sensed component 278, that is, with maximum allowable load applied to load sensor 262.

Referring to FIG. 14A and FIG. 14B, the process for automated calibration of load sensor 262 and overload protection of load sensor 262 is the same as described above for the load sensing system of FIG. 13A and FIG. 13B.

Figure 15A:
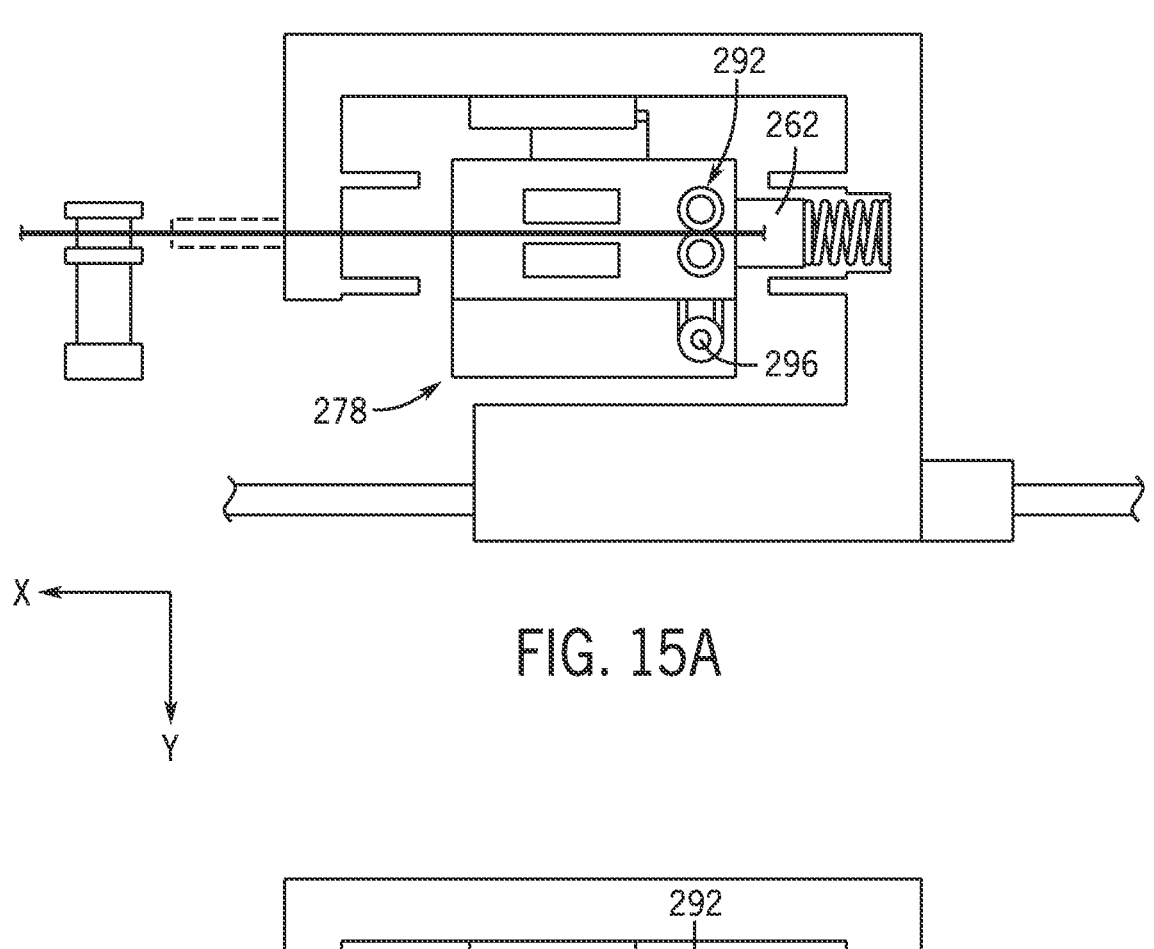
FIG. 15A is schematic top view of another embodiment of a load sensing system for measuring force and torque on an EMD in a robotic system with automated calibration and overload protection of a sensor shown in a neutral (no load) position where the drive actuator is located inside the load-sensed component.
Figure 15B:
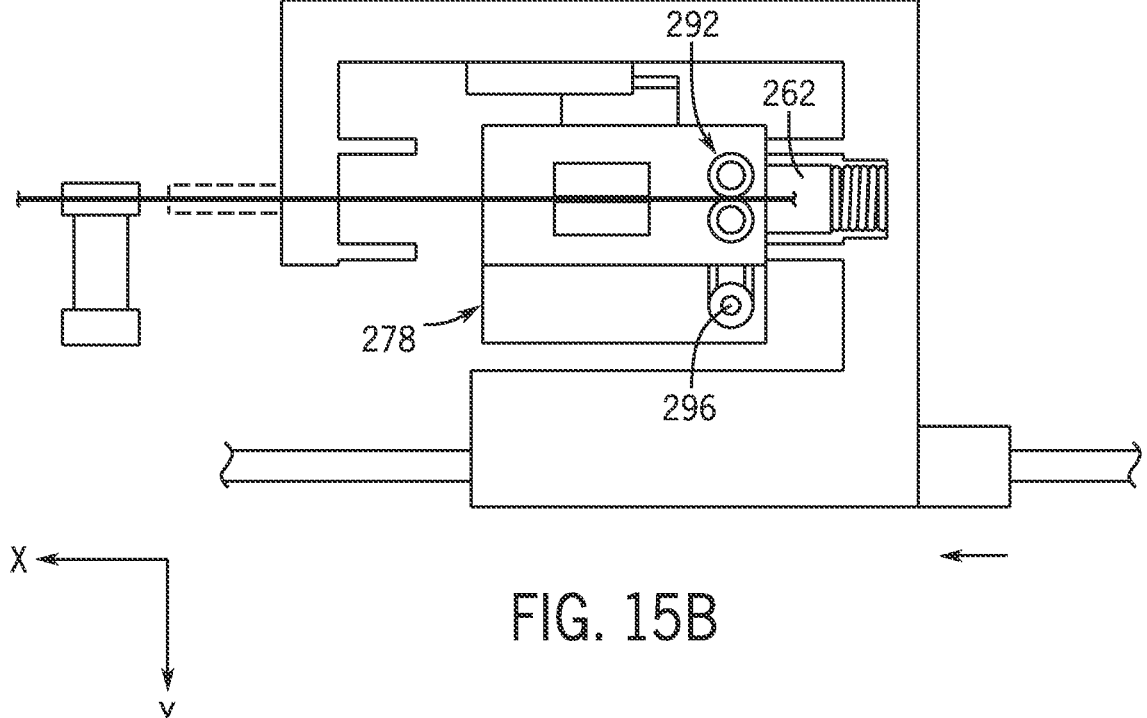
FIG. 15B is schematic top view of an embodiment of the load sensing system of FIG. 15A shown in a loaded position where the drive actuator is located inside the load-sensed component.

Referring to FIG. 15A and FIG. 15B, an alternate embodiment of a load sensing system with automated calibration and overload protection of its load sensor includes components that are the same as components of the load sensing system of FIG. 14A and FIG. 14B. In this alternate embodiment tire drive mechanism 292 is driven by a drive actuator 296 mounted to load-sensed component 278. In one embodiment drive actuator 296 is mounted inside load-sensed component 278.

Referring to FIG. 15A, which is an alternate embodiment of FIG. 14A, the load sensing system is indicated in a neutral position of load-sensed component 278. Referring to FIG. 15B, which is an alternate embodiment of FIG. 14B, the load sensing system is indicated in a maximum loaded position of load-sensed component 278.

Referring to FIG. 15A and FIG. 15B, the process for automated calibration of load sensor 262 and overload protection of load sensor 262 is the same as described above for the load sensing system of FIG. 13A and FIG. 13B.

Figures 16A, 16B:
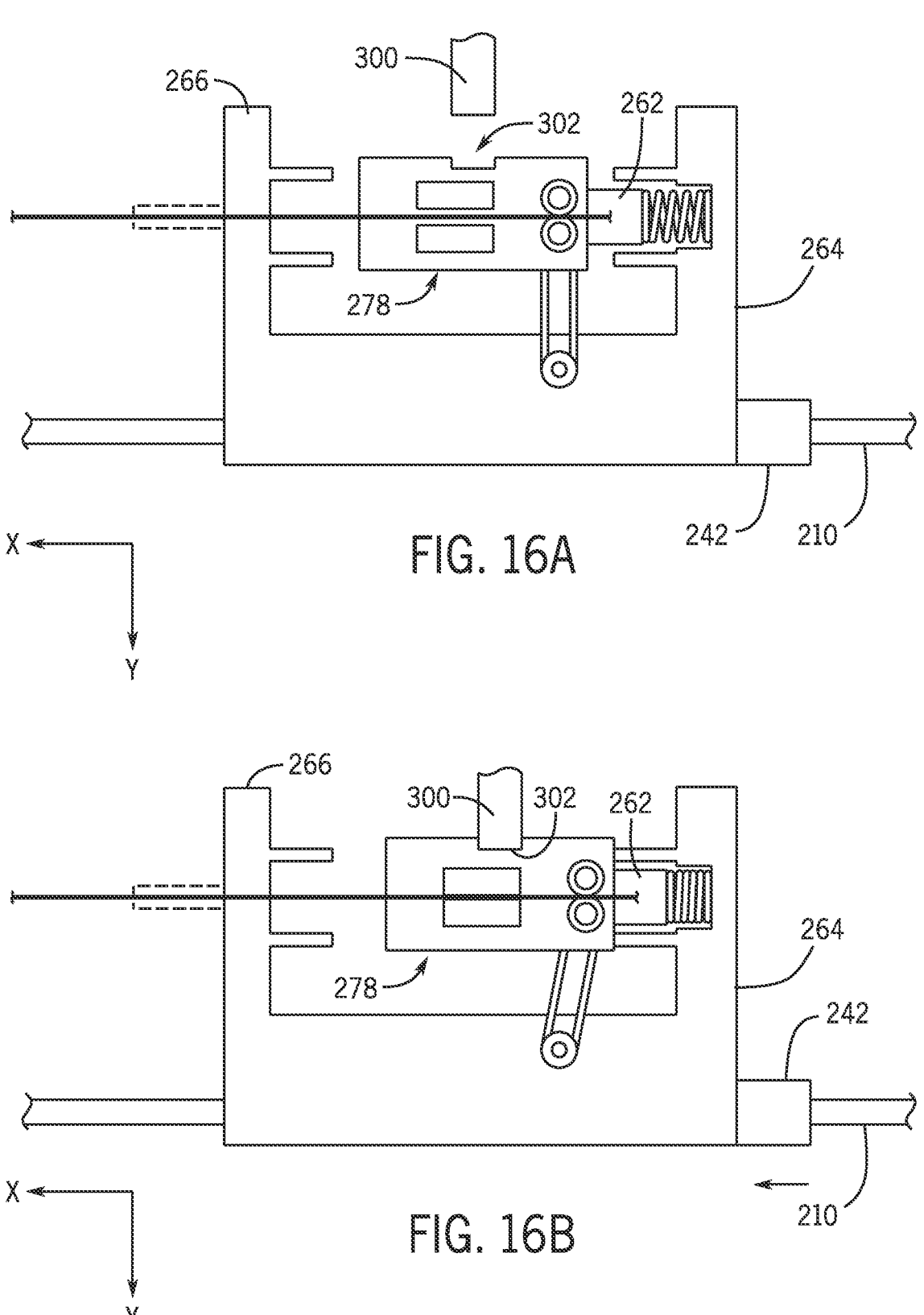
FIG. 16A is schematic top view of another embodiment of a load sensing system for measuring force and torque on an EMD in a robotic system with automated calibration and overload protection of a sensor shown in a neutral (no load) position.
FIG. 16B is schematic top view of another embodiment of a load sensing system for measuring force and torque on an EMD in a robotic system with automated calibration and overload protection of a sensor shown in a loaded position.

Referring to FIG. 16A and FIG. 16B, an alternate embodiment of a load sensing system with automated calibration and overload protection of its load sensor includes a locking member 300 that reversibly fixes the longitudinal location of load-sensed component 278 relative to stage drive mechanism 210 while stage translation motor 242 translates drive module 264 along stage drive mechanism 210. Longitudinal motion of load-sensed component 278 is prevented by seating locking member 300 into a pocket 302 in load-sensed component 278. In one embodiment locking member 300 is a locking pin. In one embodiment locking member 300 is a flange. In one embodiment locking member 300 is a protrusion or projection of a link. In one embodiment locking member 300 locks load-sensed component 278 by friction.

Locking member 300 is constrained to linear motion in the transverse direction (actuated and controlled by a system not shown). In one embodiment locking member 300 is constrained to linear motion by a linear bearing. In one embodiment locking member 300 is constrained to linear motion by guides. In one embodiment locking member 300 linear motion is accomplished by rotation of a screw.

Referring to FIG. 16A, which is an alternate embodiment of FIG. 14A, the load sensing system is indicated in a neutral position of load-sensed component 278. Load-sensed component 278 is supported by load sensor and an elastic component in the longitudinal direction and constrained in transverse directions by a linear bearing (not shown), which integrally connects load-sensed component 278 and drive module base component 266. Referring to FIG. 16B, which is an alternate embodiment of FIG. 14B, the load sensing system is indicated in a loaded position of load-sensed component 278.

Referring to FIG. 16A and FIG. 16B, the process for automated calibration of load sensor 262 and overload protection of load sensor 262 is similar to that described above for the load sensing system of FIG. 13A and FIG. 13B, where fixing the location of the load-sensed component 278 is achieved by seating locking member 300 into pocket 302 thereby preventing longitudinal motion of load-sensed component 278.

Figure 17:
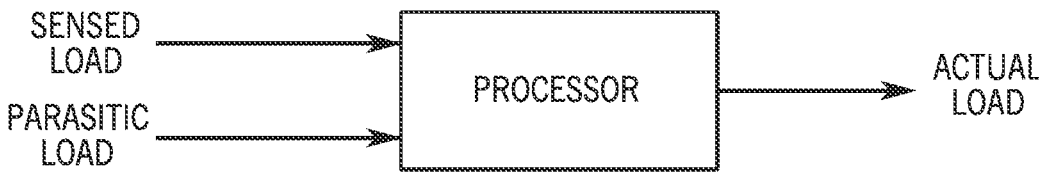
FIG. 17 is a block diagram of a processor with two inputs (sensed load and parasitic load) and one output (actual load).
Figure 18:
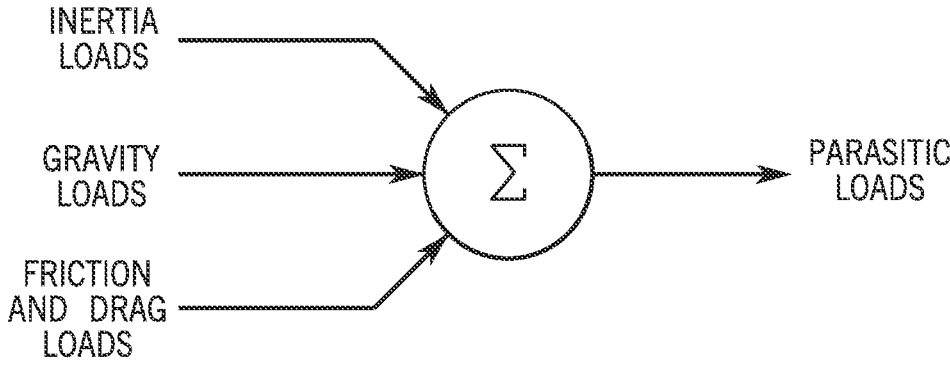
FIG. 18 is a block diagram summation symbol indicating loads that are combined to be parasitic loads.

Referring to FIGS. 17 and 18, a processor or processing unit corrects the load measurements for parasitic loads corrupting the measurement of the actual load acting on the EMD, where the parasitic loads may include but are not limited to frictional loads, inertia loads, drag loads, and gravity loads.

Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. The present disclosure described is manifestly intended to be as broad as possible. For example, unless specifically otherwise noted, the definitions reciting a single particular element also encompass a plurality of such particular elements.

What is claimed is:

1. An apparatus comprising:
a collet having a first portion having a first collet coupler connected thereto and a second portion having a second collet coupler connected thereto;
an elongated medical device (EMD) being removably located within a pathway defined by the collet;
a drive module including a first actuator operatively coupled to the first collet coupler to operatively pinch and unpinch the EMD in the pathway and to rotate the EMD and a second actuator operatively engaging the second collet coupler;
a first load sensor to determine a first collet coupler torque acting on the first collet coupler; and
a processor determining an EMD torque acting on the EMD as a function of a first signal from the first load sensor.

2. The apparatus of claim 1, wherein the second actuator operatively engages and disengages the second collet coupler, respectively to prevent and allow rotation of the second collet coupler.

3. The apparatus of claim 1, wherein the second collet coupler operatively pinches and unpinches the EMD in the pathway to rotate the EMD; and
further including a second load sensor to determine a second collet coupler torque acting on the second collet coupler;
wherein the processor determines the EMD torque acting on the EMD as a function of the first signal from the first load sensor and a second signal from the second load sensor.

4. The apparatus of claim 3, wherein the processor determines a net collet torque applied to the collet for pinch and/or unpinching the EMD.

5. The apparatus of claim 4, wherein the EMD torque is related to a pinch force on the EMD.

6. The apparatus of claim 5, wherein the first load sensor is positioned between the first actuator and the first collet coupler and the second load sensor is positioned between the second actuator and second collet coupler.

7. The apparatus of claim 5, wherein the first load sensor is positioned between the first actuator and a housing of the drive module.

8. The apparatus of claim 5, wherein the second load sensor is positioned between the second actuator and a housing of the drive module.

9. An apparatus for calibrating a load sensor comprising:
a drive module including a drive module base component,
a load-sensed component,
a load sensor and
an elastic component having a known stiffness, the elastic component being intermediate the load sensor and the drive module base component;
a cassette removably secured to the drive module, the cassette including a housing and an isolated component movable within the housing;
the cassette configured to receive an elongated medical device (EMD); and
a mechanical stop limiting a movement of the isolated component relative to one of the housing and the drive module base component in a direction of the elastic component limiting a maximum deflection of the elastic component to a known distance between the mechanical stop and the isolated component.

10. The apparatus of claim 9, wherein a distance between the mechanical stop and the load-sensed component is predetermined to limit a maximum load applied to the load sensor such that the load sensor is protected from being overloaded.

11. The apparatus of claim 9, wherein a second sensor detects contact between the load-sensed component and the mechanical stop.

12. The apparatus of claim 9, wherein a processor is used to determine and remove zero offset from a measurement from the load sensor.

13. The apparatus of claim 9, wherein a processor is used to correct a calibration factor by comparing a measured load and a known load.

14. The apparatus of claim 13, wherein load sensor calibration is accomplished manually by pushing the load-sensed component towards the mechanical stop until the load-sensed component contacts the mechanical stop.

15. The apparatus of claim 13, wherein a mechanism is used to clamp the EMD and load the sensor calibration is accomplished automatically.

16. The apparatus of claim 15, wherein the EMD is supported by a device support.

17. The apparatus of claim 13, wherein a locking member fixes the load-sensed component in place independent of the drive module base component for automated calibration.

18. The apparatus of claim 13, wherein an overload protection of the load sensor and automated calibration of the load sensor measures an axial force on the EMD.

19. The apparatus of claim 13, wherein an overload protection of the load sensor and automated calibration of the load sensor measures a torque about the EMD longitudinal axis.

20. The apparatus of claim 13, wherein an overload protection of the load sensor and automated calibration of the load sensor measures an axial force and a torque acting on the EMD.

21. An apparatus comprising:
a first drive module including a first on-device adapter operatively engaging an elongated medical device (EMD) to manipulate the EMD, wherein the first drive module includes a first load sensor to measure a load applied by the first drive module to the EMD;
a second drive module having a second on-device adapter releasably engaging the EMD, wherein a reset state includes moving the first on-device adapter relative to the second drive module between an extended position and a reset position;
a second load sensor operatively connected to the second on-device adapter and the second drive module; and
a processor receiving a first signal from the first load sensor and a second signal from the second load sensor and determines an actual load on the EMD as a function of the first signal,
second signal and a state of the first on-device adapter and a state of the second on-device adapter.

22. The apparatus of claim 21, wherein the first on-device adapter includes a collet.

23. The apparatus of claim 22, wherein the second on-device adapter includes a clamp having a pair of rolling members.

24. An apparatus for calibrating a load sensor comprising:
a drive module; and
a cassette removably secured to the drive module,
wherein the drive module includes a drive module base component, a load-sensed component, a load sensor and an elastic component having a known stiffness,
wherein the load-sensed component is configured to be movable relative to the drive module base component,
wherein the load sensor is intermediate the load-sensed component and the elastic component and configured to sense a load acting on the load-sensed component,
wherein the elastic component is intermediate the load sensor and the drive module base component, and
wherein the cassette includes a housing and an isolated component movable within the housing and coupled to the load-sensed component, the isolated component configured to receive an elongated medical device (EMD).

\* \* \* \* \*